US010946020B2

(12) United States Patent
Purow et al.

(10) Patent No.: US 10,946,020 B2
(45) Date of Patent: Mar. 16, 2021

(54) COMPOSITIONS AND METHODS FOR TREATING CANCER

(71) Applicant: University of Virginia Patent Foundation, Charlottesville, VA (US)

(72) Inventors: Benjamin Purow, Charlottesville, VA (US); Desiree Floyd, Gordonsville, VA (US); Inan Olmez, Charlottesville, VA (US); Thurl E. Harris, Jr., Covesville, VA (US); Salome Boroda, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/091,000

(22) PCT Filed: Apr. 6, 2017

(86) PCT No.: PCT/US2017/026401
§ 371 (c)(1),
(2) Date: Oct. 3, 2018

(87) PCT Pub. No.: WO2017/177037
PCT Pub. Date: Oct. 12, 2017

(65) Prior Publication Data
US 2019/0060317 A1    Feb. 28, 2019

Related U.S. Application Data

(60) Provisional application No. 62/319,248, filed on Apr. 6, 2016.

(51) Int. Cl.
*A61K 31/519*    (2006.01)
*A61K 31/4706*    (2006.01)
*A61K 31/495*    (2006.01)
*A61K 45/06*    (2006.01)
*A61P 35/00*    (2006.01)

(52) U.S. Cl.
CPC ........ *A61K 31/519* (2013.01); *A61K 31/4706* (2013.01); *A61K 31/495* (2013.01); *A61K 45/06* (2013.01); *A61P 35/00* (2018.01); *A61K 2300/00* (2013.01)

(58) Field of Classification Search
CPC .... A61K 31/519; A61K 45/06; A61K 31/495; A61K 31/4706; A61K 2300/00; A61P 35/00
See application file for complete search history.

(56) References Cited

U.S. PATENT DOCUMENTS

| 4,160,452 | A | 7/1979 | Theeuwes |
| 4,256,108 | A | 3/1981 | Theeuwes |
| 4,265,874 | A | 5/1981 | Bonsen et al. |
| 8,367,737 | B2 | 2/2013 | Qu et al. |
| 2012/0129810 | A1 | 5/2012 | Amaravadi et al. |

FOREIGN PATENT DOCUMENTS

| WO | WO 00/16750 A1 | 3/2000 |
| WO | WO 00/57858 A1 | 10/2000 |
| WO | WO 2014018563 | * 1/2014 |

OTHER PUBLICATIONS

Floyd, "ATPS-22 Ritanserin and Temozolomide Synergize Against Human Glioblastoma In Vitro and in Established Tumors In Vivo", Neuro Oncol. Nov. 2015; 17(Suppl 5): v22-v23.*
Tso, "Primary Glioblastomas Express Mesenchymal Stem-Like Properties", Mol Cancer Res 2006;4:607-619.*
Klok et al., "Cholesteryl-(L-Lactic Acid)ñ Building Blocks for Self-Assembling Biomaterials," Macromolecules, vol. 35, Iss. 3, pp. 746-759 (2002).
Lee et al., "The synergistic effect of combination temozolomide and chloroquine treatment is dependent on autophagy formation and p53 status in glioma cells," Cancer Lett., vol. 360, No. 2, pp. 195-204 (2015).
Leysen et al., "Receptor-binding properties in vitro and in vivo of ritanserin: A very potent and long acting serotonin-S2 antagonist," Mol Pharmacol., vol. 27, No. 6, pp. 600-611 (1985).
Portoghese et al., "Opioid Agonist and Antogonist Bivalent Ligands as Receptor Probes," Life Sci. vol. 31 pp. 1283-1286 (1982).
Portoghese et al., "Opioid Agonist and Antagonist Bivalent Ligands. The Relationship between Spacer Length and Selectivity at Multiple Opioid Receptors," J. Med. Chem., vol. 29, No. 10, pp. 1855-1861 (1986).
Tamiz et al., "Pharmacological and Behavioral Analysis of the Effects of Some Bivalent Ligand-Based Monoamine Reuptakes Inhibitors," J. Med. Chem., vol. 44, pp. 1615-1622 (2001).
Wittlinger et al., "Time and dose-dependent activation of p53 serine 15 phosphorylation among cell lines with different radiation sensitivity," Int J Radiat Biol., vol. 83, No. 4, pp. 245-257 (2007).
Ampie et al., "Heatshock protein vaccines against Glioblastoma: From bench to bedside," J Neurooncol, vol. 123, No. 3, pp. 441-448 (Jul. 2015).
Bhat et al., "Mesenchymal Differentiation Mediated by NF-KB Promotes Radiation Resistance in Glioblastoma," Cancer Cell, vol. 24, No. 3, pp. 331-346 (2013).
Bullock et al., "Manipulation of Avidity to Improve Effectiveness of Adoptively Transferred CD8(+) T Cells for Melanoma Immunotherapy in Human MHC Class I-Transgenic Mice," J Immunol., vol. 167, No. 10, pp. 5824-5831 (2001).

(Continued)

*Primary Examiner* — Sahar Javanmard
(74) *Attorney, Agent, or Firm* — Jenkins, Wilson, Taylor & Hunt, P.A.

(57) ABSTRACT

Ritanserin is shown to be an inhibitor of diacylglycerol kinase alpha (DGKα) and to be cytotoxic to glioblastoma and melanoma cells. Ritanserin treatment also provides chemo- and radiosensitization in cancer cells, prolonged survival in mouse models of glioblastoma, decreased melanoma tumor burden in mice, and shows synergistic cytotoxic effects with temozolomide and chloroquine, both singly and in combination. DGKα inhibition with ritanserin shows particular toxicity to the treatment-resistant mesenchymal subtype in glioblastoma and other cancers.

12 Claims, 27 Drawing Sheets
Specification includes a Sequence Listing.

(56) References Cited

OTHER PUBLICATIONS

Chianale et al., "Diacylglycerol Kinase-α Mediates Hepatocyte Growth Factor-induced Epithelial Cell Scatter by Regulating Rac Activation and Membrane Ruffling," Molecular Biology of the Cell, vol. 18, No. 12, pp. 4859-4871 (Dec. 2007).
Chou, "Drug combination studies and their synergy quantification using the Chou-Talalay method," Cancer Research, vol. 70, No. 2, pp. 440-446 (2010).
De Chaffoy de Courcelles et al., "R 59 022, a Diacylglycerol Kinase Inhibitor: Its effect on Diacylglycerol and Thrombin-induced C Kinase Activation in the Intact Platelet," J Biol Chem., vol. 60, No. 29, pp. 15762-15770 (1985).
Domingo-Musibay et al., "What next for newly diagnosed glioblastoma?" Future Oncology, vol. 11, No. 24, pp. 3273-3283 (2015).
Domingues et al., "Diacylglycerol Kinase α is a Critical Signalling Node and Novel Therapeutic Target in Glioblastoma and Other Cancers," Cancer Discovery, vol. 3, No. 7, pp. 782-797 (Jul. 2013).
Hori et al., "Chloroquine potentiates temozolomide cytotoxicity by inhibiting mitochondrial autophagy in glioma cells," J Neurooncol., vol. 122, No. 1, pp. 11-20 (2015).
Hussey et al., "Synthesis of a β-Estradiol-Biotin Chimera that Potently Heterodimerizes Estrogen Receptor and Streptavidin Proteins in a Yeast Three-Hybrid System," J. Am. Chem. Soc., vol. 125, No. 13, pp. 3692-3693 (2003).
International Preliminary Report on Patentability corresponding to International Application No. PCT/US2017/026401 dated Oct. 9, 2018.
International Search Report and Written Opinion of the International Searching Authority corresponding to International Application No. PCT/US2017/026401 dated Jul. 17, 2017.
Kefas et al., "A miR-297/hypoxia/DGK-α axis regulating glioblastoma survival," Neuro-Oncology, vol. 15, No. 12, pp. 1652-1663 (2013).
Kim et al., "Wnt activation is implicated in glioblastoma radioresistance," Lab Invest., vol. 92, No. 3, pp. 466-473 (2012).
Kimura et al., "Chloroquine in Cancer Therapy: A Double-Edged Sword of Autophagy," Cancer Research, vol. 73, No. 1, pp. 3-7 (2013).
Loughery et al., "Critical role for p53-serine 15 phosphorylation in stimulating transactivation at p53-responsive promoters," Nucleic Acids Research, vol. 42, No. 12, pp. 7666-7680 (2014).
Mao et al., "Mesenchymal glioma stem cells are maintained by activated glycolytic metabolism involving aldehyde dehydrogenase 1A3," Proc Natl Acad Sci, vol. 110, No. 21, pp. 8644-8649 (2013).
Olenchock et al., "Disruption of diacylglycerol metabolism impairs the induction of T cell anergy," Nat Immunol., vol. 7, No. 11, pp. 1174-1181 (2006).
Olin et al., "Superior Efficacy of Tumor Cell Vaccines Grown in Physiologic Oxygen," Clinical Cancer Res., vol. 16, No. 19, pp. 4800-4808 (2010).
Ostrom et al., "CBTRUS Statistical Report: Primary Brain and Central Nervous System Tumors Diagnosed in the United States in 2008-2012," Neuro-Oncol., vol. 17, Suppl 4, pp. iv1-iv62 (2015).
Paar et al., "Bivalent Ligands with Rigid Double-Stranded DNA Spacers Reveal Structural Constraints on Signaling by FcεRl1," J. Immunol., vol. 169, pp. 856-864 (2002).
Phillips et al., "Molecular subclasses of high-grade glioma predict prognosis, delineate a pattern of disease progression, and resemble stages in neurogenesis," Cancer Cell, vol. 9, No. 3, pp. 157-173 (2006).
Purow, "Molecular Pathways: Targeting Diacylglycerol Kinase Alpha in Cancer," Clinical Cancer Research, vol. 21, No. 22, pp. 5008-5012 (Nov. 2015).
Roller et al., "Synthetic Lethal Screening with Small-Molecule Inhibitors Provides a Pathway to Rational Combination Therapies for Melanoma," Mol Cancer Ther., vol. 11, No. 11, pp. 2505-2515 (2012).
Verhaak et al., "Integrated Genomic Analysis Identifies Clinically Relevant Subtypes of Glioblastoma Characterized by Abnormalities in PDGFRA, IDH1, EGFR, and NF1," Cancer Cell, vol. 17, No. 1, pp. 98-110 (2010).
Zha et al., "T cell anergy is reversed by active Ras and is regulated by diacylglycerol kinase-α," Nat Immunol., vol. 7, No. 11, pp. 1166-1173 (2006).
Nobe et al., "Effect of diacylglycerol kinase inhibitor, R59022 on cytosolic free calcium level and force development in guinea pig taenia coli.," Res Commun Chem Pathol Pharmacol., vol. 81, No. 3, pp. 331-343 (1993). [abstract only].
Olmez et al., "Targeting the mesenchymal subtype in glioblastoma and other cancers via inhibition of diacylglycerol kinase alpha," Neuro-Oncology, pp. 1-11 (2017).
Sato et al., "Evaluations of the Selectivities of the Diacylglycerol Kinase Inhibitors R59022 and R59949 Among Diacylglycerol Kinase Isozymes Using a New Non-Radioactive Assay Method," Pharmacology, vol. 92, No. 1-2, pp. 99-107 (2013).
Stepinski et al., "Use of hydrophilic diamines for bridging of two opioid peptide pharmacophores," Internat. J. of Peptide & Protein Res. vol. 38, pp. 588-592 (1991).
Timmerman et al., "Deuterated ritanserin analysis by gas chromatography/mass spectrometry: a sensitive technique to study human ritanserin pharmacokinetics," Biomed Environ Mass Spectrom, vol. 18, No. 7, pp. 498-502 (1989).

\* cited by examiner

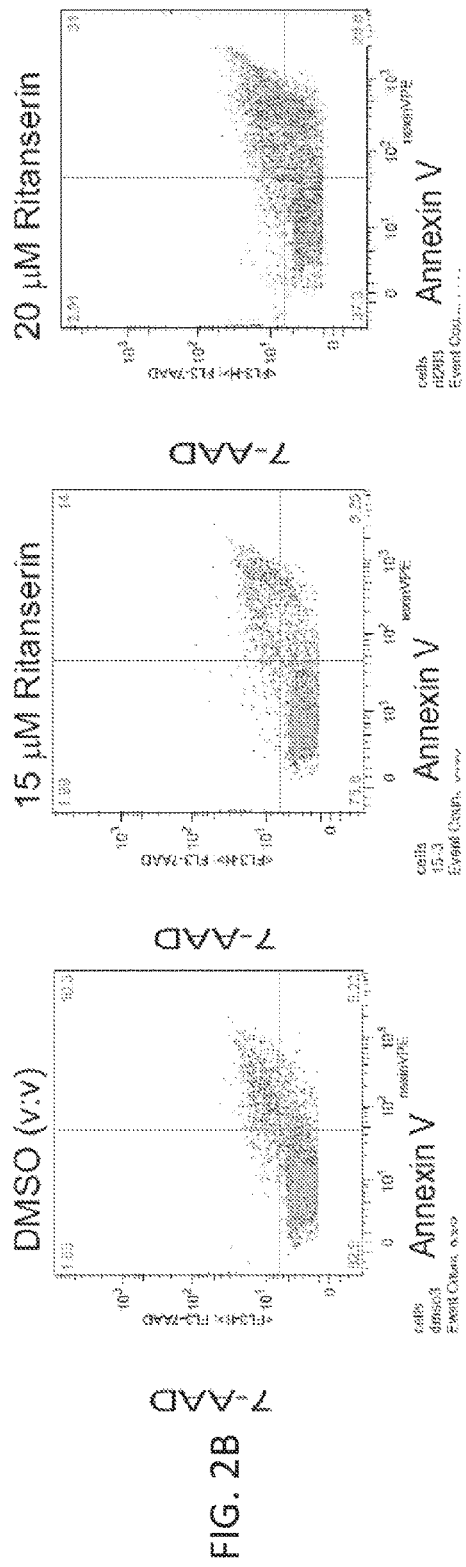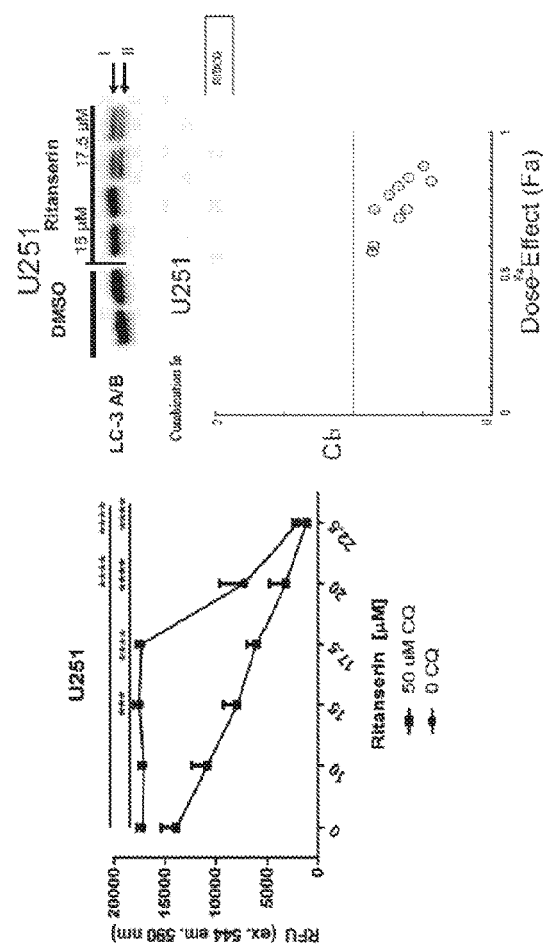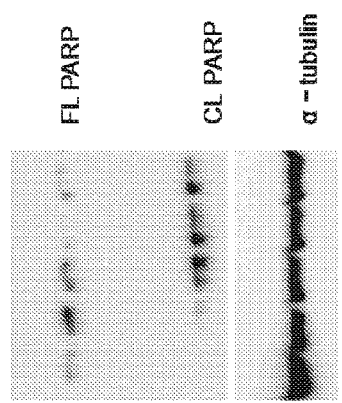
FIG. 2B
FIG. 2C
FIG. 2D

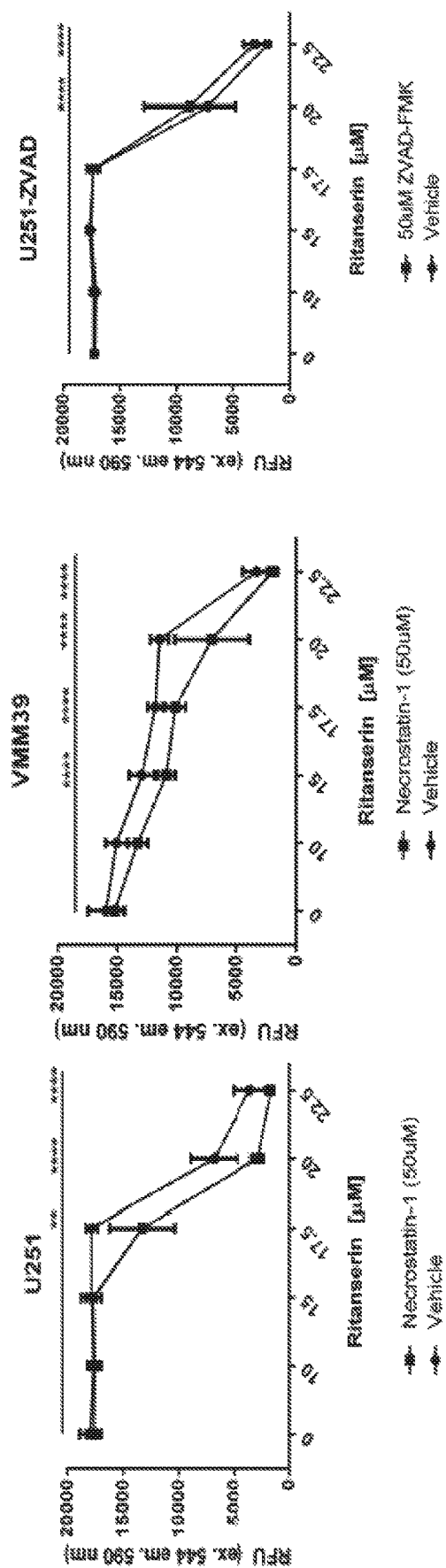
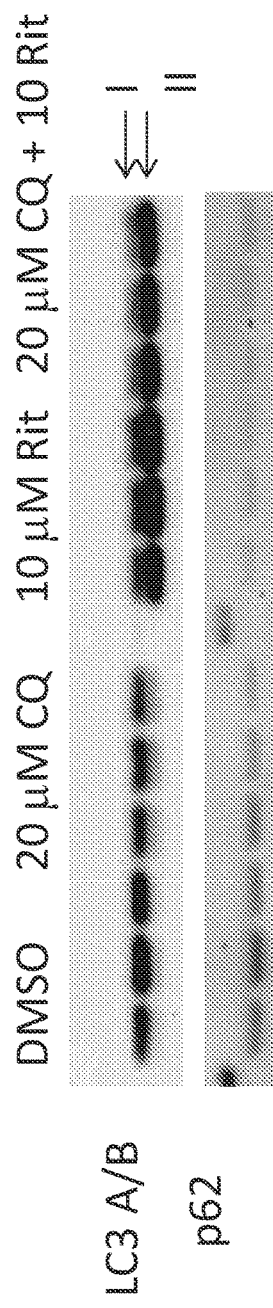
FIG. 2G
FIG. 2H

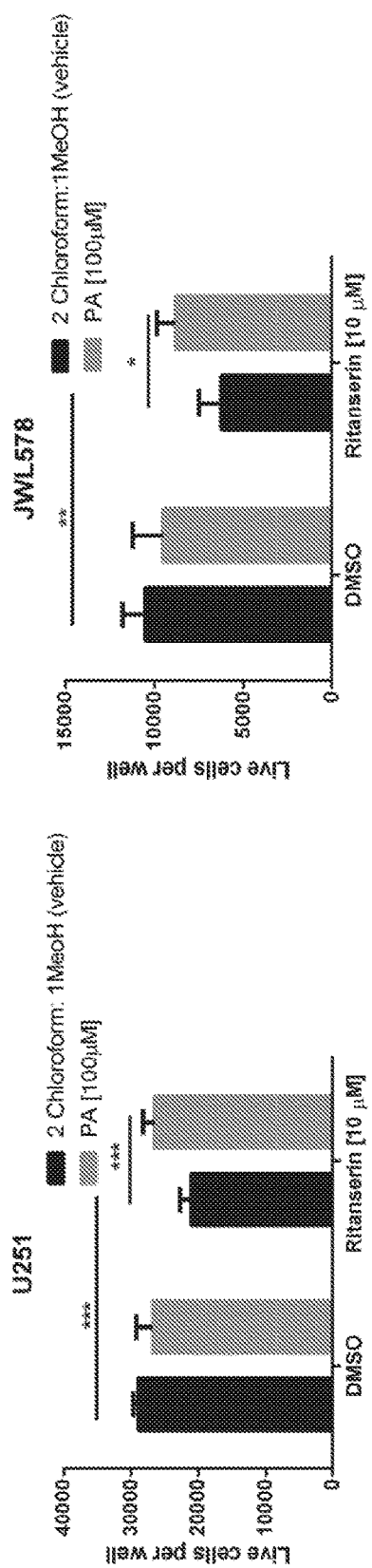
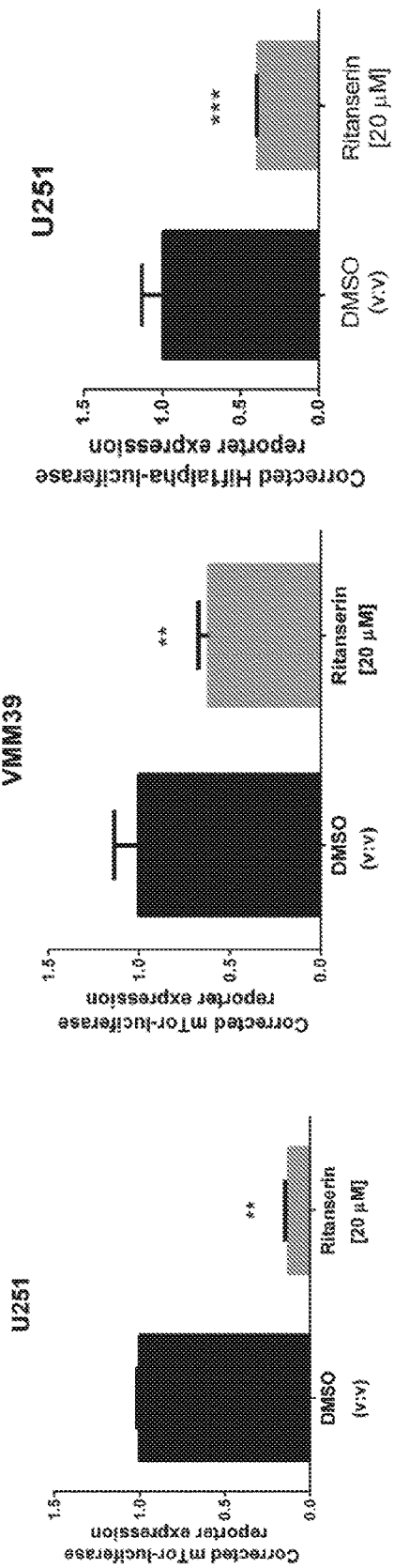
FIG. 3A
FIG. 3B

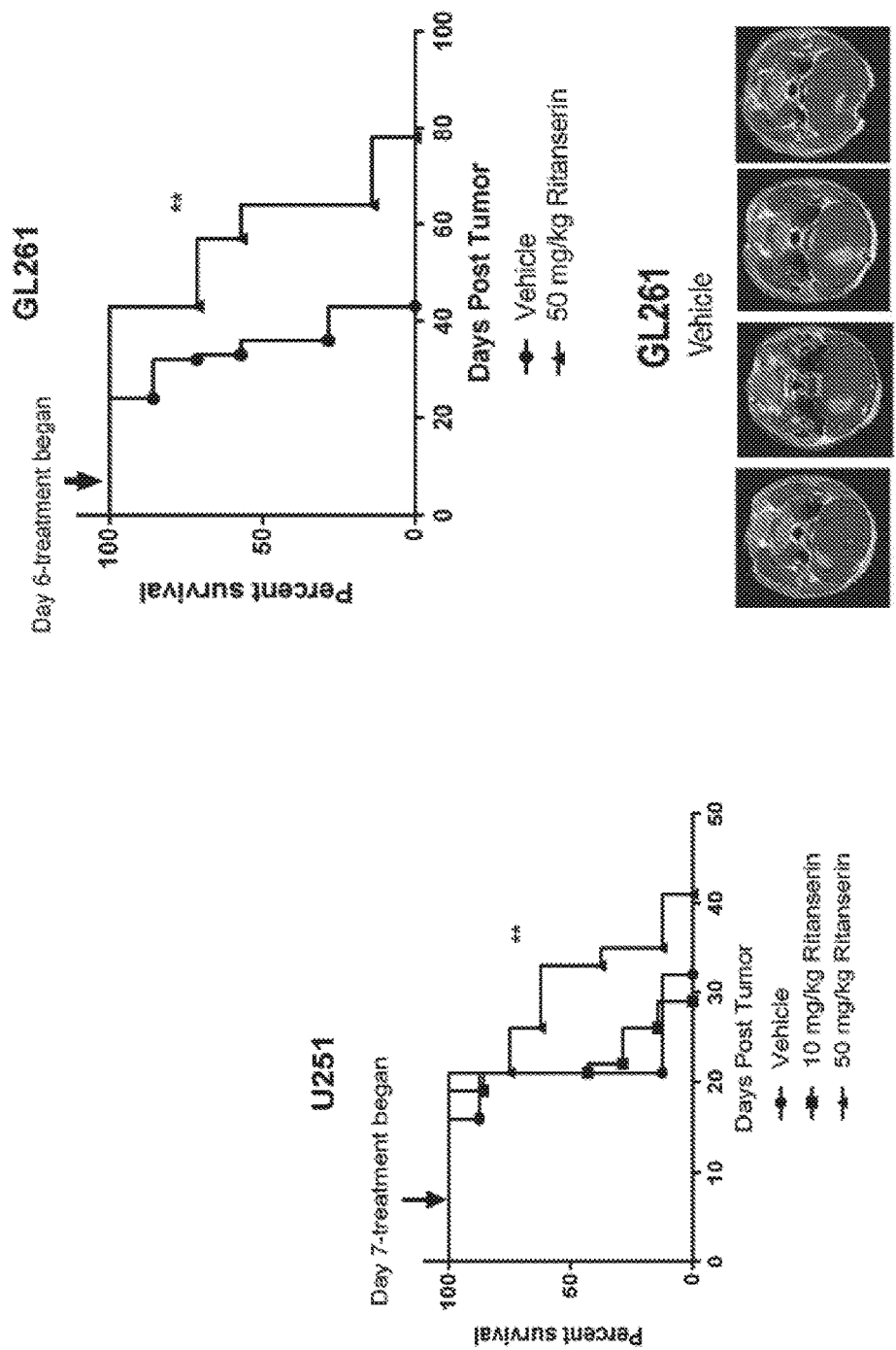
FIG. 5B
FIG. 5A

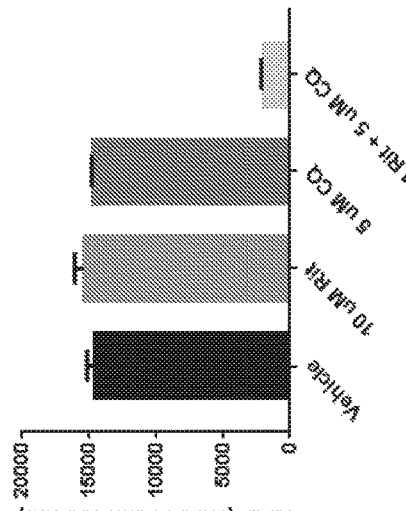
FIG. 7E
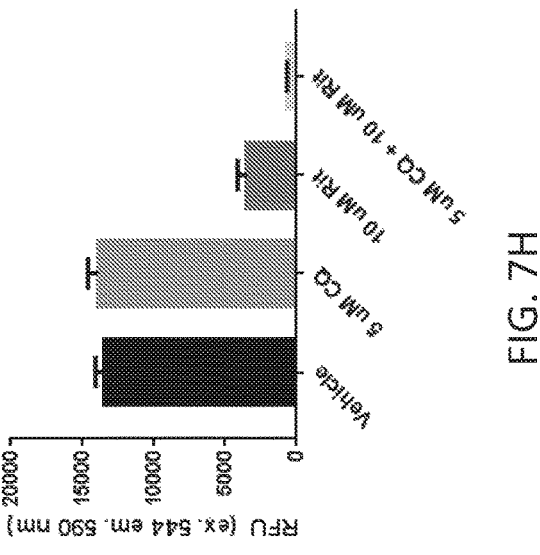
FIG. 7F
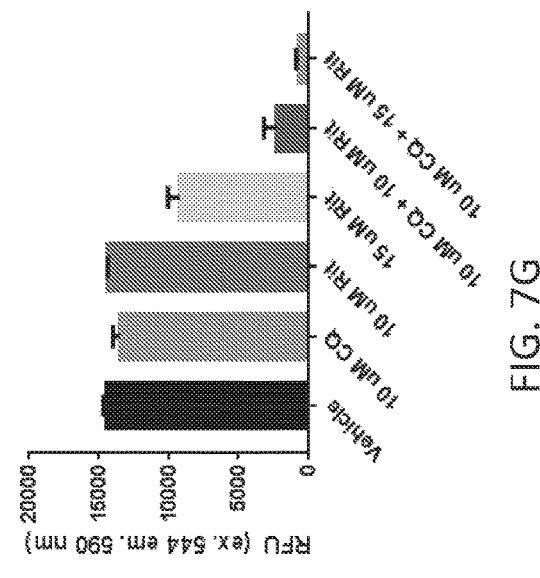
FIG. 7G
FIG. 7H

COMPOSITIONS AND METHODS FOR TREATING CANCER

CROSS REFERENCE TO RELATED APPLICATIONS

This application is a national phase application of PCT International Patent Application PCT/US2017/026401, filed Apr. 6, 2017, which claims the benefit of U.S. Provisional Patent Application Ser. No. 62/319,248, filed Apr. 6, 2016, each of which is incorporated herein by reference in its entirety.

GRANT STATEMENT

This invention was made with government support under Grant Nos. CA 180699 and CA 189524 awarded by the National Institutes of Health. The government has certain rights in the invention.

TECHNICAL FIELD

The presently disclosed subject matter provides compositions comprising ritanserin or analog thereof for treating cancers, such as glioblastomas and melanomas, and for inhibiting diacylglycerol kinase alpha. Also provided are methods of treating cancer using ritanserin or analog thereof, alone or in combination with other agents.

ABBREVIATIONS

° C.=degrees Celsius
%=percentage
μg=microgram
μl=microliter
μM=micromolar
CI=combination index
CQ=chloroquine
DAG=diacylglycerol
DGKα=Diacylglycerol Kinase alpha
DMSO=dimethylsulfoxide
em.=emission
g=grams
GBM=glioblastoma multiforme
$IC_{50}$=50% inhibitory concentration
kg=kilogram
min=minute
mg=milligram
ml=milliliter
mm=millimeter
mM=millimolar
MRI=magnetic resonance imaging
N=normal
nm=nanometer
PA=phosphatidic acid
RFU=relative fluorescence units
TMZ=temozolomide
v=volume

BACKGROUND

Glioblastoma multiforme (GBM) is an incurable Grade 4 tumor of the central nervous system, comprising nearly half of malignant adult primary brain tumors. See Ostrom et al., 2015. Recent clinical trials with electric fields have improved average survival times when added to the standard regimen of surgery, radiation, and temozolomide (TMZ), but median survival is still under two years. See Domingo-Musibay et al., 2015.

Diacylglycerol Kinase alpha (DGKα), a highly conserved enzyme that catalyzes the conversion of diacylglycerol (DAG) to phosphatidic acid (PA), has recently been shown to be a cancer therapeutic target upstream of mTOR, HIF-1α, and cAMP signaling. See Dominguez et al., 2013; and Kefas et al., 2013. More particularly, GBM and melanoma cells have been found to be sensitive to DGKα knockdown and to inhibition with the DGKα inhibitors R59022 and R59949. See Dominguez et al., 2013. DGKα inhibition has also been shown to prevent T cell anergy, indicating that it can be a cancer immunotherapy target. See Olenchock et al., 2006; and Zha et al., 2006.

R59022 was first described several decades ago (see de Chaffoy de Dourcelles et al., 1985.), but only recently shown to be cytotoxic to cancer. R59022 has not been studied in humans, and animal models have been mostly ex vivo. See Nobe et al., 1993. In recent mouse models, R59022 delayed subcutaneous melanoma progression, but had limited efficacy in orthotopic glioblastoma, perhaps due to limited blood-brain barrier penetrance and rapid clearance from the serum. See Dominguez et al., 2013.

Accordingly, there is an ongoing need for additional compositions and methods useful for treating diseases and disorders involving DGKα and its signaling pathways, such as cancer. In particular, there is an ongoing need for additional pharmaceutically active agents and methods for treating GBM and other cancers. For example, there is a need for additional agents that can inhibit DGKα and that can cross the blood-brain barrier. There is also a need for DGKα inhibitors that can increase the efficacy of other treatments for GBM and other cancers.

SUMMARY

In some embodiments, the presently disclosed subject matter provides a method for treating a cancer in a subject in need thereof, wherein the method comprises administering to the subject a therapeutically effective amount of ritanserin or analog thereof. In some embodiments, the cancer is a melanoma or a glioblastoma. In some embodiments, the cancer is a mesenchymal cancer. In some embodiments, the cancer is a mesenchymal glioblastoma.

In some embodiments, the method further comprises administering at least one second treatment to the subject. In some embodiments, the at least one second treatment is selected from the group comprising a surgical resection of a tumor, radiotherapy, immunotherapy, alternating electric field therapy, or chemotherapy. In some embodiments, the method comprises administering to the subject at least one second treatment selected from the group comprising temozolomide (TMZ), chloroquine, bevacizumab, imatinib, radiation, or an immunotherapeutic agent.

In some embodiments, the method comprises administering to the subject at least two second treatments, wherein the at least two second treatments have synergistic activity with each other. In some embodiments, the at least two second treatments are TMZ and chloroquine.

In some embodiments, the ritanserin is administered orally to the subject. In some embodiments, the subject is human.

In some embodiments, the presently disclosed subject matter provides a composition comprising ritanserin, or analog thereof; and at least one of temozolomide (TMZ), chloroquine, bevacizumab, imatinib, or an immunotherapeutic agent. In some embodiments, the composition comprises ritanserin, TMZ, and chloroquine.

In some embodiments, the composition further comprises a pharmaceutically acceptable excipient. In some embodiments, the pharmaceutically acceptable excipient is selected from the group comprising granulating agents, binding agents, lubricating agents, disintegrating agents, sweetening agents, glidants, anti-adherents, anti-static agents, surfactants, anti-oxidants, gums, coloring agents, flavouring agents, coating agents, plasticizers, preservatives, suspending agents, emulsifying agents, spheronization agents or combinations thereof. In some embodiments, the composition is formulated for oral administration.

In some embodiments, the presently disclosed subject matter provides a method of inhibiting diacylglycerol kinase alpha (DGKα) in a biological sample, wherein the method comprises contacting the sample with ritanserin or analog thereof. In some embodiments, the biological sample is selected from the group comprising a cell, a tissue, an organ or a subject.

In some embodiments, the presently disclosed subject matter provides a method of inducing chemo- or radiosensitivity in a subject undergoing or scheduled to undergo treatment with a chemotherapeutic agent or radiation to treat a disease or disorder treatable thereby, the method comprising administering ritanserin or analog thereof to the subject. In some embodiments, administering the ritanserin is performed prior to and/or concurrently with the administration of a chemotherapeutic agent. In some embodiments, administering the ritanserin is performed prior to and/or concurrently with the administration of radiation.

In some embodiments, the disease or disorder is a cancer. In some embodiments, the cancer is a mesenchymal cancer. In some embodiments, the cancer is a melanoma or a glioblastoma.

Accordingly, it is an object of the presently disclosed subject matter to provide compositions and methods for treating cancer and/or inhibiting DGKα.

An object of the presently disclosed subject matter having been stated hereinabove, and which is achieved in whole or in part by the presently disclosed subject matter, other objects will become evident as the description proceeds hereinbelow.

BRIEF DESCRIPTION OF THE DRAWINGS

FIG. 2B is a series of plots of Annexin V positive U251 human glioblastoma cells after treatment with vehicle (dimethylsulfoxide, DMSO) (left), with 15 micromolar (μM) ritanserin (middle), or with 20 μM ritanserin (right). The plots represent gating on live cells and 10,000 events were counted in three replicates per treatment.

FIG. 2C is (left) a plot of relative fluorescence units (RFU) of U251 human glioblastoma cells treated with 0 to 22.5 micromolar (μM) ritanserin alone (circles) or a combination of 0 to 22.5 μM ritanserin and 50 μM chloroquine (CQ) (squares). Cells were treated for three days and an alamarBlue assays was performed. Error bars represent standard deviation. P values shown were generated from one-way analysis of variance (ANOVA) with Tukey's post-test for multiple comparisons ($p<0.05$, *, $p<0.01$, , $p<0.001$, *, $p<0.0001$, ****). In the upper right is a radiograph of an immunoblot of lysates of ritanserin-treated U251 cells. The lysates were made after 24 hours of treatment and immunoblotted for autophagy indicator LC3 A/B II. In the bottom right is a combination index generated by the Chou-Talalay method for determining synergy based on data for the combination of ritanserin and CQ.

FIG. 2D is a radiograph of an immunoblot of U251 human glioblastoma cells treated only with vehicle (dimethylsulfoxide, DMSO) or with 15 μM ritanserin and assayed for poly ADP Ribose Polymerase (PARP) cleavage.

FIG. 2G is a series of graphs showing the cytotoxic effects of ritanserin (0 to 22.5 micromolar (μM) ritanserin) on necrostatin-1 pretreated U251 human glioblastoma cells (left), necrostatin-1 pretreated VMM39 human melanoma cells (center) and on ZVAD-FMK pre-treated U251 human glioblastoma cells (right). Cell survival data is provided as relative fluorescence units (RFU) measured with alamarBlue reagent. Pretreatment with necrostatin-1 was performed with 50 μM necrostatin-1. Pretreatment with ZVAD-FMK was performed with 50 μM ZVAD-FMK. Error bars represent standard deviation. P values shown were generated from one-way analysis of variance (ANOVA) with Tukey's post-test for multiple comparisons (p<0.05, *, p<0.01, , p<0.001, *, p<0.0001, ****).

FIG. 2H are radiographs of immunoblots of lysates of U251 cells treated with 20 micromolar (μM) chloroquine (CQ), 10 μM ritanserin (Rit), or a combination of 20 μM CQ and 10 μM ritanserin. The lysates were made after 48 hours of treatment and immunoblotted for autophagy indicator LC3 A/B II and p62.

FIG. 3A is a pair of graphs showing the effects of phosphatidic acid (PA) on ritanserin cytotoxicity in U251 human glioblastoma cells (left) and JWL578 human glioblastoma stem cells (right). U251 and JWL cells were incubated with 10 micromolar (μM) ritanserin or dimethylsulfoxide (DMSO) and either vehicle (2:1 chloroform:methanol; volume:volume; black bars) or 100 μM PA (grey bars). Live cells were collected and counted 48 hours later. Student's T-test or one-way analysis of variance (ANOVA) with Tukey's post-test was used for analysis (p<0.01, , p<0.001, *).

FIG. 3B is a series of graphs showing mechanistic target of rapamycin (mTOR) promoter reporter activity in U251 human glioblastoma cells (left) and VMM39 human melanoma cells (center) or hypoxia-inducible factor 1 alpha (HIF-1α) binding activity in U251 human glioblastoma cells (right) measured in response to 20 micromolar (μM) ritanserin (grey bars) or dimethylsulfoxide (DMSO) in a dual luciferase assay. Student's T-test or one-way analysis of variance (ANOVA) with Tukey's post-test was used for analysis (p<0.01, , p<0.001, *).

FIG. 5A is a graph showing the survival curves of athymic nu/nu mice implanted intracranially with U251 human glioblastoma cells and treated with 10 milligrams per kilogram (mg/kg) ritanserin (squares) or 50 mg/kg ritanserin (triangles). For comparison, the survival curve of mice implanted with U251 human glioblastoma cells and treated with vehicle (corn oil) is also shown (circles). Daily treatment with ritanserin or corn oil was started seven days after implantation of the glioblastoma cells. Seven mice were used per group. Kaplan-Meier analysis was used for survival curve generation (p<0.01,**).

FIG. 5B is (top) a graph showing the survival curves of wild type C57BL/6 mice implanted intracranially with GL261 murine glioma cells and treated daily after six days with 50 milligrams per kilogram (mg/kg) ritanserin (triangles) or vehicle (corn oil) (circles); and (bottom) magnetic resonance imaging (MRI) images of the mice performed three weeks after implantation of the glioma cells. Seven mice were used per group. Kaplan-Meier analysis was used for survival curve generation (p<0.01,**).

FIG. 7E is a graph showing the synergistic cytotoxic effects of chloroquine (CQ) and ritanserin (Rit) on VMM49 human melanoma cells. Cells were treated with 10 micromolar (μM) CQ and/or 15 μM Rit and then cell survival was analyzed 72-96 hours later via alamarBlue assay. For comparison, data (provided in relative fluorescence units (RFU)) is also provided for cells treated with vehicle.

FIG. 7F is a graph showing the synergistic cytotoxic effects of chloroquine (CQ) and ritanserin (Rit) on B16 mouse melanoma cells. Cells were treated with 5 micromolar (μM) CQ and/or 10 μM Rit and then cell survival was analyzed 72-96 hours later via alamarBlue assay. For comparison, data (provided in relative fluorescence units (RFU)) is also provided for cells treated with vehicle.

FIG. 7G is a graph showing the synergistic cytotoxic effects of chloroquine (CQ) and ritanserin (Rit) on G528 human glioblastoma stem cells. Cells were treated with 10 micromolar (μM) CQ and/or 10 μM or 15 μM Rit and then cell survival was analyzed 72-96 hours later via alamarBlue assay. For comparison, data (provided in relative fluorescence units (RFU)) is also provided for cells treated with vehicle.

FIG. 7H is a graph showing the synergistic cytotoxic effects of chloroquine (CQ) and ritanserin (Rit) on G34 human glioblastoma stem cells. Cells were treated with 5 micromolar (μM) CQ and/or 10 μM and then cell survival was analyzed 72-96 hours later via alamarBlue assay. For comparison, data (provided in relative fluorescence units (RFU)) is also provided for cells treated with vehicle.

DETAILED DESCRIPTION

Figure 1A:
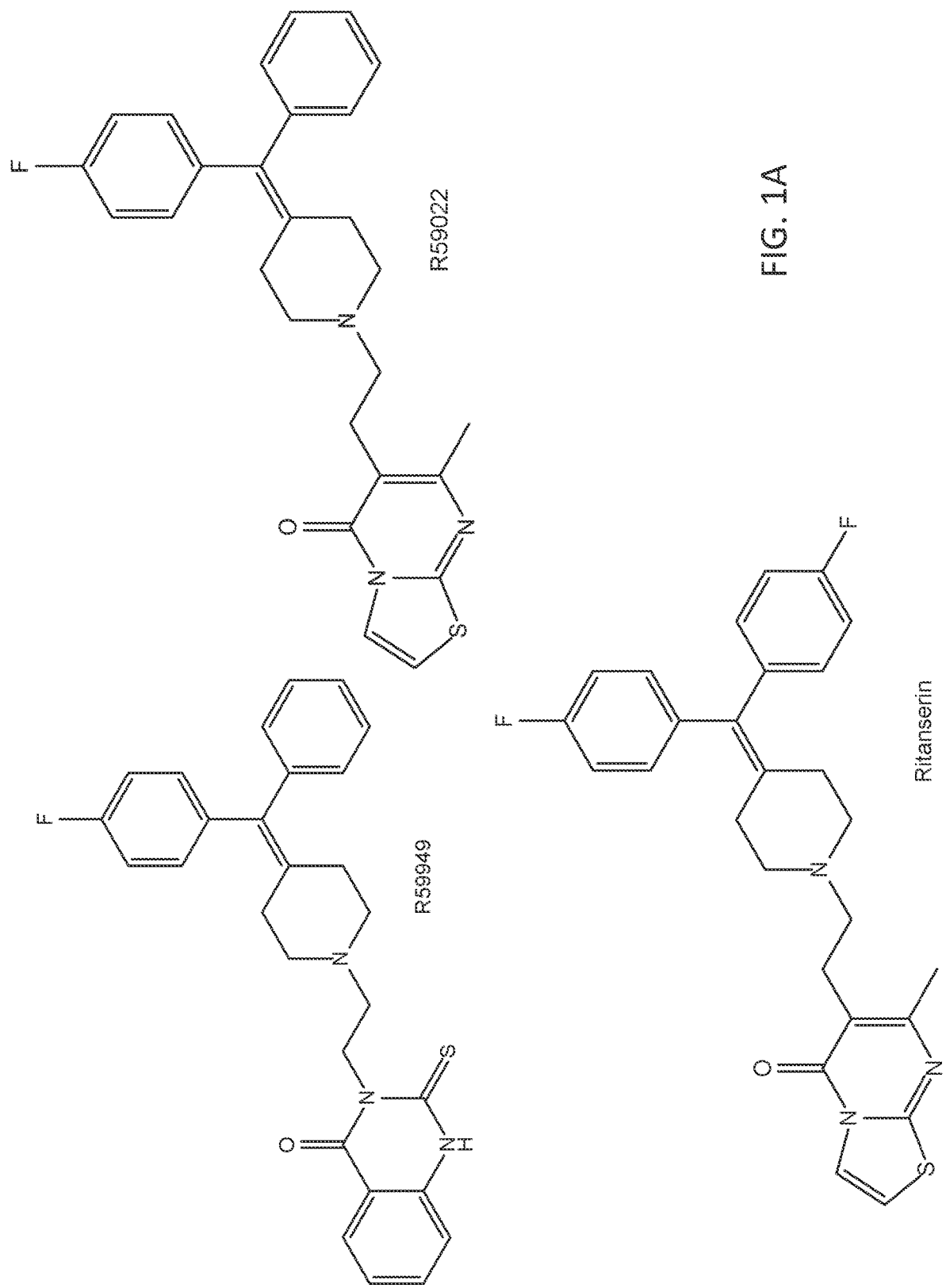
FIG. 1A is a schematic drawing of the chemical structures of R59949, R59022, and ritanserin.

The presently disclosed subject matter will now be described more fully. The presently disclosed subject matter can, however, be embodied in different forms and should not be construed as limited to the embodiments set forth herein below and in the accompanying Examples. Rather, these embodiments are provided so that this disclosure will be thorough and complete, and will fully convey the scope of the embodiments to those skilled in the art.

All references listed herein, including but not limited to all patents, patent applications and publications thereof, and scientific journal articles, are incorporated herein by reference in their entireties to the extent that they supplement, explain, provide a background for, or teach methodology, techniques, and/or compositions employed herein.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long-standing patent law convention, the terms "a", "an", and "the" refer to "one or more" when used in this application, including the claims.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" can mean at least a second or more.

The term "comprising," which is synonymous with "including," "containing," or "characterized by," is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

Unless otherwise indicated, all numbers expressing quantities of temperature, time, concentration, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value is meant to encompass variations of in one example ±20% or ±10%, in another example ±5%, in another example ±1%, and in still another example ±0.1% from the specified amount, as such variations are appropriate to perform the disclosed methods.

Numerical ranges recited herein by endpoints include all numbers and fractions subsumed within that range (e.g. 1 to 5 includes, but is not limited to, 1, 1.5, 2, 2.75, 3, 3.90, 4, and 5).

A "compound," as used herein, refers to any type of chemical or biochemical substance or agent that is commonly considered a drug, or a candidate for use as a drug, as well as combinations and mixtures of the above.

The term "active compound" as used herein refers to ritanserin and derivatives or analogs thereof, particularly those that have the ability to inhibit DGKα and/or that are cytotoxic. Active compounds also include therapeutically active compounds that can be used in combination with ritanserin or derivatives or analogs thereof to treat a disease or disorder, such as cancer. In particular, active compounds include other anti-cancer therapeutic agents known in the art and compounds that, as described herein, act synergistically with ritanserin or with a derivative or analog thereof.

As used herein, the term "derivative" refers to a chemical compound that can be produced from another compound of similar structure in one or more chemical or biochemical steps, e.g., via the replacement of a H by an alkyl, aryl, aralkyl, acyl or amino group.

As used herein, an "analog" of a chemical compound is a compound that, by way of example, resembles another in structure but is not necessarily an isomer (e.g., 5-fluorouracil is an analog of thymine).

The term "treatment" as used herein refers to any treatment that has a beneficial effect in treatment of a disease or disorder. Thus, a treatment can include a therapeutically effective and/or biologically active compound (e.g., an active compound as described above and/or chemotherapy), a composition comprising one or more active compounds or other drugs, a therapeutic biomolecule (e.g., an antibody, protein, DNA or RNA) administered to treat a disease or symptom thereof, surgery, radiation treatment, immunotherapy, alternating electric field therapy, etc.

"Co-administer" can include simultaneous and/or sequential administration of two or more treatments.

The term "effective amount" can refer to an amount sufficient to produce a selected effect, such as alleviating symptoms of a disease or disorder or of inhibiting an enzyme.

The term "therapeutically effective amount" refers to an amount (e.g., target plasma concentration or unit dosage) of an active compound or other treatment (e.g., radiation) sufficient to produce a beneficial effect to a subject being treated with the compound or other treatment, such as alleviating symptoms of a disease or disorder. For example, a therapeutically effective amount can be the amount of the compound that produces a reduction in tumor size, reduces or prevents cancer cell metastasis, increases subject survival, and/or the amount that reduces a symptom of the cancer. Thus, in the treatment of GBM, a therapeutically effective amount can be the amount necessary to reduce headaches, seizures, aphasia, cognitive disorders, nausea or other symptoms.

In the context of administering active compounds in the form of a combination, such as multiple compounds, the effective amount of each compound, when administered in combination with another compound(s), can be different from when that compound is administered alone. Thus, the effective amount of a combination of compounds can refer collectively to the combination as a whole, although the actual amounts of each compound can vary.

The term "more effective" means that the selected effect is alleviated to a greater extent by one treatment relative to the second treatment to which it is being compared.

The term "inhibit," as used herein, refers to the ability of a compound or any agent to reduce or impede a described function, level, activity, synthesis, release, binding, etc., based on the context in which the term "inhibit" is used. In some embodiments, "inhibit" refers to the reduction of the catalytic activity of an enzyme. In some embodiments, inhibition is by at least 10%, 25%, 50%, or at least 75%. The term "inhibit" is used interchangeably with "reduce" and "block."

As used herein, "treating" a disease or disorder refers to reducing the number of diseased (e.g., cancer) cells in a subject, curtailing the spread of the diseased cells in the subject (e.g., preventing metastasis of a cancer), reducing the severity and/or frequency of one or more effects or symptoms of the disease in a subject, increasing the survival of a subject being treated for the disease or disorder, and/or providing any other beneficial effect to the subject. Thus, treatment is typically administered to a subject who exhibits signs of pathology for the purpose of diminishing or eliminating those signs.

As used herein, the term "synergize" and variations thereof (e.g., "synergistic") refer to the ability of one treatment to increase the biological effect (e.g., the cytotoxic effect) of a second treatment. Synergistic activity, thus, includes but is not limited to an increased biological effect (e.g., more potent or longer lasting) using the two treatments (e.g., two drugs) together that is not observed when the treatments are used separately; a more effective biological effect, e.g., elimination of multiple symptoms of a disease; or a reduction in the amount of treatment (e.g., a reduction in the dosage of a drug) necessary for administration to achieve the biological effect observed with a single treatment. Synergistic activity can refer to an interaction or cooperation between at least two treatments (e.g., two therapeutic compounds or a therapeutic compound and another therapeutic treatment, such as radiotherapy or surgery) that enhance or magnifies one or more biological effect. Thus, in some embodiments, the synergistic activity produces a combined biological effect greater than the sum of their separate biological effects. In some embodiments, synergy refers to a combination of two or more treatments (e.g., two or more individual active compounds) that has a combination index (CI) that is less than 1.

The terms "biological sample" or "sample" refer to a sample from a subject, including, but not limited to, normal tissue samples, disease tissue samples, biopsies, blood, saliva, feces, semen, tears, and urine. A sample can also be any other source of material obtained from a subject which contains cells, cell components, tissues, and/or a fluid of interest.

The term "cancer" as used herein refers to diseases caused by uncontrolled cell division and the ability of cells to metastasize, or to establish new growth in additional sites. The terms "malignant," "malignancy," "neoplasm," "tumor," "cancer," and variations thereof refer to cancerous cells or groups of cancerous cells.

Particular types of cancer include, but are not limited to, skin cancers (e.g., melanomas), connective tissue cancers (e.g., sarcomas), adipose cancers, breast cancers, head and neck cancers, lung cancers (e.g., mesothelioma), stomach cancers, pancreatic cancers, ovarian cancers, cervical cancers, uterine cancers, anogenital cancers (e.g., testicular cancer), kidney cancers, bladder cancers, colon cancers, prostate cancers, central nervous system (CNS) cancers (e.g., glioblastomas and gliomas), retinal cancer, blood, neuroblastomas, multiple myeloma, and lymphoid cancers (e.g., Hodgkin's and non-Hodgkin's lymphomas).

The terms "anticancer drug," "chemotherapeutic," and "anticancer prodrug" refer to drugs (i.e., chemical compounds) or prodrugs known to, or suspected of being able to treat a cancer (i.e., to kill cancer cells, prohibit proliferation of cancer cells, or treat a symptom related to cancer). In some embodiments, the term "chemotherapeutic" as used herein refers to a natural or non-natural (i.e., synthetic) small molecule that is used to treat cancer and/or that has cytotoxic ability. Such more traditional or conventional chemotherapeutic agents can be described by mechanism of action or by chemical compound class, and can include, but are not limited to, alkylating agents (e.g., melphalan, temozolomide), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib, imatinib, etc.), nucleotide analogs or precursors thereof (e.g., methotrexate), peptide antibiotics (e.g., bleomycin), platinum based agents (e.g., cisplatin or oxaliplatin), retinoids (e.g., tretinoin), and vinka alkaloids (e.g., vinblastine). In some embodiments, the chemotherapeutic agent is an antibody (e.g., a human, chimeric, or humanized antibody) or fragment thereof.

The term "cytotoxic" as used herein refers to the ability of a compound or agent to be toxic to cells, particularly cancer cells. Cytotoxicity can relate to causing an increase in cell necrosis, the ability to cause cells to stop growing and/or dividing, and/or the ability to induce apoptosis in cells. Cytotoxicity can be observed and/or measured by a variety of assays known in the art, including, but not limited to, colorometric assays for measuring cell metabolic activity, e.g., using 3-(4,5-dimethylthiaxol-2-yl)-2,5-diphenyltetrazolium bromide (MTT), water-soluble tetrazolium (WST) salts, MTS, XTT, or the like; sulforhodamine B assays; clonogenic assays; ATP-based assays (e.g., luciferase assays); and electric cell-substrate impedance sensing (ECIS).

The term "immunotherapeutic agent" as used herein refers to an agent that modulates (i.e., activates or suppresses) the immune response. In some embodiments, the immunotherapeutic agent stimulates the immune response. In some embodiments, the immunotherapeutic agent is an immunosuppressant. Immunotherapeutic agents, include, for example, immunomodulators, such as interleukins, cytokines (e.g. interferons), chemokines, and immunomodulatory imide drugs.

The term "pharmaceutical composition" as used herein refers to a composition comprising at least one active compound, whereby the composition is amenable for administration to a subject, e.g., to provide an efficacious outcome in the subject (e.g., a human or other mammal). Those of ordinary skill in the art will understand and appreciate the techniques appropriate for determining whether an active ingredient has a desired efficacious outcome based upon the needs of the artisan.

As used herein, the term "pharmaceutically acceptable carrier" includes, by way of example and not limitation, any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, and which is not deleterious to the subject to which the composition is to be administered.

The term "concurrently" when used in the context of the administration of two or more different active compounds and/or other treatments can refer to the simultaneous administration of the two or more active compounds or other treatments (e.g., the administration of a single composition comprising two or more active compounds, the administration of multiple compositions, each comprising an active compound, at roughly the same time (e.g., within about 24 hours or less, about 12 hours or less, about 6 hours or less, about 4, hours or less, about 2 hours or less, or about 30 minutes or less), the administration of a composition comprising one or more active compounds while a subject is undergoing a surgery, etc. However, "concurrently" can also be used to refer to the administration of two different active compounds and/or other treatments at different times, but while at least one of the treatments is ongoing (e.g., wherein the subject is being treated with a course of multiple doses of one active compound or with radiation over multiple days or weeks and the administration of a second active compound or other treatment is performed at some time during the course of the first treatment regimen.

Thus, as used herein, "prior to" in the context of the administration of multiple active compounds or other treatments can refer to a situation where a subject has already received a full course of one active agent or completed another treatment, e.g., a surgery, before a second treatment is initiated.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. In some embodiments, the alkyl group is "lower alkyl." "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. In some embodiments, the alkyl is "higher alkyl." "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic moiety that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, carbonyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "heteroaryl" refers to aryl groups wherein at least one atom of the backbone of the aromatic ring or rings is an atom other than carbon. Thus, heteroaryl groups have one or more non-carbon atoms selected from the group including, but not limited to, nitrogen, oxygen, and sulfur.

As used herein, the term "acyl" refers to an organic carboxylic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The terms "heterocycle" or "heterocyclic" refer to cycloalkyl groups (i.e., non-aromatic, cyclic groups as described hereinabove) wherein one or more of the backbone carbon atoms of a cyclic ring is replaced by a heteroatom (e.g., nitrogen, sulfur, or oxygen). Examples of heterocycles include, but are not limited to, tetrahydrofuran, tetrahydropyran, morpholine, dioxane, piperidine, piperazine, and pyrrolidine.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

"Alkoxyl" or "alkoxy" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

The term "amino" refers to the —NR'R" group, wherein R' and R" are each independently selected from the group including H and substituted and unsubstituted alkyl, cycloalkyl, heterocycle, aralkyl, aryl, and heteroaryl. In some embodiments, the amino group is —NH$_2$.

The term "carbonyl" refers to the —(C=O)— or a double bonded oxygen substituent attached to a carbon atom of a previously named parent group.

The term "carboxyl" refers to the —COOH group.

The terms "halo", "halide", or "halogen" as used herein refer to fluoro, chloro, bromo, and iodo groups.

The terms "hydroxyl" and "hydroxy" refer to the —OH group.

The term "oxo" refers to a compound described previously herein wherein a carbon atom is replaced by an oxygen atom.

The term "cyano" refers to the —CN group.
The term "nitro" refers to the —NO$_2$ group.

II. General Considerations

Glioblastoma (also referred to as glioblastoma multiforme (GBM)) is a common cancer originating in the brain. It tends to present with symptoms such as headache, seizures, aphasia (difficulty with speech), cognitive deficits, personality changes, and occasionally nausea/vomiting.

A number of factors render glioblastoma one of the most aggressive and treatment-resistant cancers. It is highly infiltrative throughout the brain, making it hard to surgically remove safely and completely due to the critical nature of many brain structures. It is also relatively resistant to standard therapies, such as radiation and chemotherapy. Further, many agents cannot reach glioblastoma cells adequately due to the blood-brain barrier. A small sub-population of stem cell-like cells identified within glioblastoma can also be a component to this treatment resistance.

Existing therapies provide modest improvements in overall patient survival. Standard therapy begins with maximal safe surgical resection of the tumor, followed three to four weeks later by the initiation of a six-week course of weekday radiation treatments and daily temozolomide (TMZ) chemotherapy dosing. This is followed by pulsed TMZ treatment (5 days on, 23 days off), until magnetic resonance imaging (MRI) or clinical deterioration indicates progression of the cancer. A 2005 report indicated that the addition of this TMZ regimen to radiation treatment increase median survival of patients with glioblastoma from about 12 months to 14.6 months. It also increased two-year survival from 10.4% to 26.4%. Other therapies, frequently used at times of glioblastoma progression, include bevacizumab and chemotherapies such as lomustine and carboplatin. However, none of these have been proven to improve overall survival.

Glioblastoma, like most cancers, is driven by a diverse set of genetic (and possibly epigenetic) lesions. Unfortunately, single targeted therapies have thus far proven ineffective for patients with the genetically complex and adaptable glioblastoma. One potential answer lies in treatment with a cocktail of inhibitors. However, such treatment can lead to increases in toxicity well ahead of increases in efficacy. A potentially superior alternative lies in targeting signaling hubs that in one stroke provide the crippling of multiple critical pathways in glioblastoma. For instance, the inhibition of diacylglycerol kinase alpha (DGKα), a lipid kinase that converts diacylglycerol to phosphatidic acid, has been shown to act as a signaling hub and a promising new target in the treatment of glioblastoma. See Dominguez et al. 2013. Two small-molecule inhibitors of DGKα, R59949 and R59022, have been shown to have activity against glioblastoma and other cancers in vitro and in vivo. See Dominguez et al. 2013.

The presently disclosed subject matter is based in part on the finding that ritanserin can also inhibit DGKα. Ritanserin has the molecular formula: $C_{27}H_{25}F_2N_3OS$. The IUPAC name for ritanserin is: 6-[2-[4-[bis(4-fluorophenyl)methylidene]piperidin-1-yl]ethyl]-7-methyl-[1,3]thiazolo[3,2-a]py-rimidin-5-one. Thus, ritanserin can be classified structurally as a derivative of a fused pyrimidine, more particularly of a thiazolopyrimidine. The chemical structure of ritanserin includes a 5H-[1,3]thiazolo[3,2-a]pyrimidin-5-one core that is substituted at position 7 by a methyl group and at position 6 by a 2-{4-[bis(4-fluorophenyl)methylidene]piperidin-1-yl}ethyl group.

As a potent and long-acting serotonin (5-hydroxytryptamine, 5-HT) antagonist of the subtype 5-HT2 (Ki=0.39 nM), ritanserin has had substantial clinical trial experience. It has been used in the treatment of a variety of disorders including anxiety, depression and schizophrenia. For instance, it has been shown to be safe and effective in human trials for the treatment of schizophrenia and other disorders, such as alcohol addiction, and as a sleep aid. It has little sedative action. In previous studies for use as a serotonin receptor inhibitor, ritanserin has also been shown to be orally bioavailable, to have a 40 hour half-life (see Timmerman et al., 1989), and to reach the brain in meaningful concentrations. See Leysen et al., 1985.

Figure 1B:
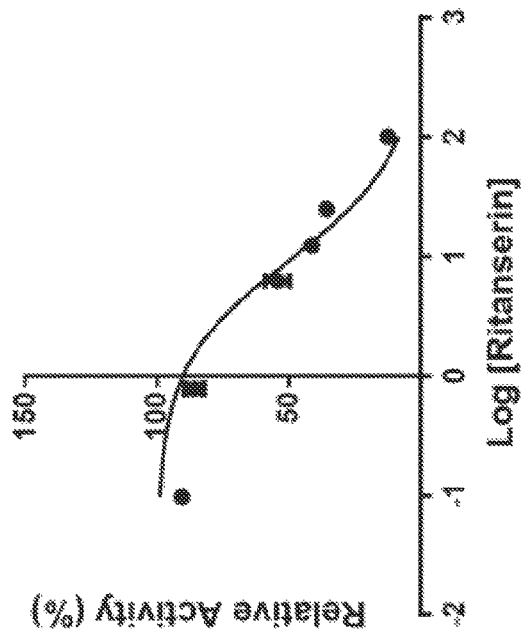
FIG. 1B is a graph showing the drug dose-dependent Diacylglycerol Kinase alpha (DGKα) activity curve with R59022. The 50 percent inhibitory concentration ($IC_{50}$) is 20 micromolar (μM), as shown by a logarithmic scale with the highest concentration of drug being 100 μM.
Figure 1C:
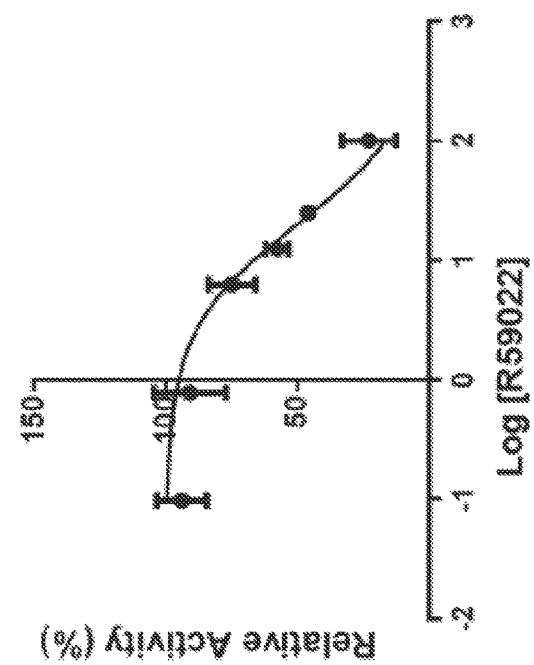
FIG. 1C is a graph showing the drug dose-dependent Diacylglycerol Kinase alpha (DGKα) activity curve with ritanserin. The 50 percent inhibitory concentration ($IC_{50}$) is 9.0 micromolar (μM), as shown by a logarithmic scale with the highest concentration of drug being 100 μM.
Figure 1D:
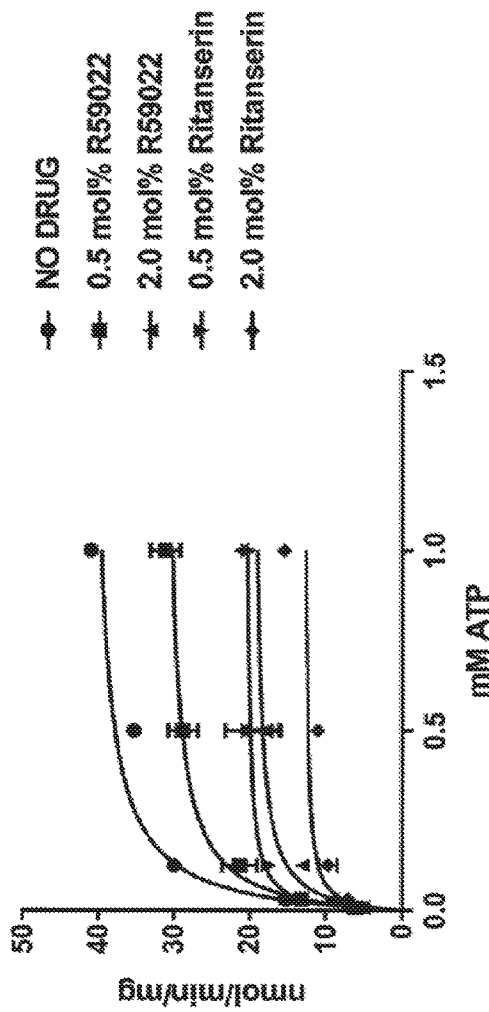
FIG. 1D is a graph showing the conversion of diacylglycerol (DAG) to phosphatidic acid (PA) by purified Diacylglycerol Kinase alpha (DGKα) as measured by mass spectrometry with increasing adenosine triphosphate (ATP) concentration, in the presence of two concentrations of R59022 (0.5 mole (mol) % R59022, squares; or 2.0 mol % R59022, upward-pointing triangles) or ritanserin (0.5 mol % Ritanserin, downward-pointing triangles; or 2.0 mol % Ritanserin, diamonds) or in the absence of drug (NO DRUG, circles).

The structure of ritanserin is shown in FIG. 1A, alongside those of R59949 and R59022, for comparison. The structure of ritanserin differs from that of R59022 by the inclusion of a second aryl fluoride substituent. As described further hereinbelow, the presently disclosed subject matter provides data showing that ritanserin has the ability to inhibit the enzymatic activity of purified DGKα and is a more potent inhibitor than the established DGKα inhibitor R59022. See FIGS. 1B-1D. Thus, ritanserin offers the possibility of accelerating the application of DGKα inhibition in the clinic.

III. Methods of Inhibiting DGKα and Treating Cancer

The presently disclosed subject matter is based in part on the finding that ritanserin can inhibit DGKα and has activity against cancer in vitro and in vivo. As described further hereinbelow, ritanserin has greater activity than the previously known DGKα inhibitor R59022. As also described further below, ritanserin exhibits additional unexpected properties, including the ability to increase the chemosensitivity and radiosensitivity of cancer cells, to synergize with other drugs, and to enhance the synergy of drugs known to synergize with one another.

For example, as described in the Examples below, it is disclosed herein that ritanserin inhibits DGKα activity in biochemical assays. Like R59022, it is strongly cytotoxic against glioblastoma and melanoma in vitro. In addition, ritanserin toxicity in GBM cells is largely rescued by administering the DGKα product phosphatidic acid (PA), indicating ritanserin action through DGKα inhibition. Further, ritanserin can be preferentially cytotoxic against mesenchymal GBM cells, a particularly treatment-resistant subset of GBM. Ritanserin increases survival and decreases tumor volume in mouse models of glioblastoma and melanoma. The presently disclosed subject matter also identifies new protein targets of DGKα inhibition and shows that ritanserin synergizes with other drugs, such as temozolomide and chloroquine, in vitro.

Accordingly, in some embodiments, the presently disclosed subject matter provides compositions and methods for treating cancer, particularly glioblastoma and melanoma. In some embodiments, the presently disclosed subject matter provides compositions and methods to treat glioblastoma, e.g., by regulating the DGKα pathway, a cancer therapeutic target. In some embodiments, the presently disclosed subject matter provides a compound, composition, or method for inhibiting DGKα.

In some embodiments, a composition comprising a therapeutically effective amount of ritanserin is administered to a subject in need thereof. Ritanserin can be understood to be the compound of the structure displayed at the bottom of FIG. 1A. In some embodiments, a therapeutically effective amount of a ritanserin analog can be used in place of the ritanserin in the presently disclosed methods and compositions. In some embodiments, the ritanserin analog can be a molecule of the structure shown at the bottom of FIG. 1A, but including one or more modifications selected from: replacement of one or more of the fluoride (F) atoms with another electronegative group, changes in the length and saturation of the ethylene linker between the piperidine group and the pyrimidinone, the addition of a substituent to the piperidine group, exchange of the pyrimidinone group with another heterocycle, replacement of the methyl substituent with another group, and replacement of the carbonyl with another group, e.g., C=NH, etc. Thus, in some embodiments, a composition comprising a therapeutically effective amount of ritanserin or a ritanserin analog is administered to the subject, wherein the ritanserin or ritanserin analog is a compound of the formula:

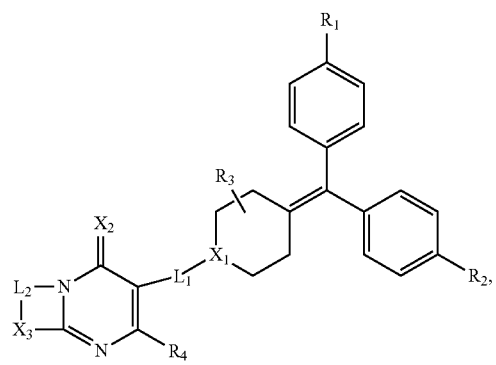

wherein:
each of $R_1$ and $R_2$ is independently selected from the group consisting of alkyl, substituted alkyl, —$CF_3$, alkoxy, hydroxyl, amino, and halo;

$R_3$ is hydrogen, hydroxyl, or alkoxy;
$R_4$ is hydrogen or alkyl;
$X_1$ is N or CH;
$X_2$ is O, $CH_2$, or NH;
$X_3$ is —S—, —$CH_2$—, or —$CR_5$=$CR_6$—;
$L_1$ is alkylene, optionally $C_1$-$C_5$ alkylene; and
$L_2$ is —$CH_2CH_2$—, $CH_2CH_2CH_2$—, or $CR_7$=$CR_8$—, wherein each $R_5$, $R_6$, $R_7$, and $R_8$ is independently H, halo, amino, alkyl or substituted alkyl.

In some embodiments, the subject is a subject who has been diagnosed with a cancer. In some embodiments, the cancer is glioblastoma, melanoma, lung cancer, or pancreatic cancer. In some embodiments, the cancer is a glioblastoma or a melanoma. In some embodiments, the subject has been newly diagnosed with the cancer (i.e., the cancer is the first occurrence of the cancer). In some embodiments, the cancer is a reoccurrence of a previously diagnosed cancer. In some embodiments, the subject is a mammal. In some embodiments, the subject is a human. In some embodiments, the ritanserin is administered orally.

In some embodiments, ritanserin or a ritanserin analog is administered in combination with at least one additional compound or treatment (i.e., with at least one "second treatment."). The additional compound can be a compound known in the art for the treatment of cancer (e.g., in the treatment of glioblastoma or melanoma) or a compound known in the art for the treatment of another disease or disorder. In some embodiments, the additional compound can be an immunotherapeutic agent. In some embodiments, the additional compound is selected from temozolomide (TMZ) or derivatives thereof, e.g., the perillyl alcohol conjugate of TMZ (TMZ-POH, also known as NEO212), chloroquine, imatinib, or bevacizumab (tradename Avastin). In some embodiments, the additional compounds are temozolomide and chloroquine. In some embodiments, the additional treatment is radiation treatment, surgery, or alternating electric field therapy. The additional compound or treatment can be administered at the same time as the composition comprising ritanserin or a ritanserin analog (i.e., concurrently) and/or at another time (i.e., prior to and/or after administration of the composition comprising ritanserin or a ritanserin analog).

In some embodiments, ritanserin or a ritanserin analog inhibits DGKα activity. In some embodiments, ritanserin or a ritanserin analog is cytotoxic to cancer cells. In some embodiments, treatment with ritanserin or a ritanserin analog increases chemosensitivity of cancer cells to other cytotoxic agents. In some embodiments, ritanserin or ritanserin analog treatment of cells increases radiosensitivity.

In some embodiments, the effects of treatment with ritanserin or a ritanserin analog and one or more additional compounds or treatments are synergistic. In some embodiments, ritanserin or a ritanserin analog synergizes with temozolomide. In some embodiments, ritanserin or a ritanserin analog synergizes with chloroquine. In some embodiments, ritanserin or a ritanserin analog potentiates chloroquine synergy with temozolomide. In some embodiments, ritanserin or a ritanserin analog synergizes with imatinib. In some embodiments, ritanserin or a ritanserin analog synergizes with radiation.

In some embodiments, mesenchymal cells are more sensitive to ritanserin or a ritanserin analog than are non-mesenchymal cells. In some embodiments, ritanserin or a ritanserin analog is more effective against proneural cells converted to a mesenchymal phenotype.

It is disclosed herein that treatment of cancer with ritanserin or a ritanserin analog increases median survival time.

In some embodiments, the cancer is a mesenchymal cancer. In some embodiments, the mesenchymal cancer is a glioblastoma.

It is disclosed herein that ritanserin inhibits or suppresses, inter alia, DGKα activity, RhoA, GGTase I, NF-ΚB, p53, and HSP60. Ritanserin is therefore useful for treating diseases and disorders where these activities are associated with the disease or disorder.

In some embodiments, treatment with ritanserin or a ritanserin analog inhibits tumor growth. In some embodiments, the combination of ritanserin or a ritanserin analog and another compound or treatment inhibits the development of chemoresistance and/or radioresistance. In some embodiments, the combination of ritanserin or a ritanserin analog and another compound or treatment inhibits a shift in phenotype (or subtype) of a cancer cell or cells.

In some embodiments, treatment with ritanserin or a ritanserin analog is at a dosage ranging from about 1.0 mg/kg body weight to about 500 mg/kg body weight. In some embodiments, the range is from about 10 mg/kg/body weight to about 250 mg/kg body weight. In some embodiments, the range is from about 25 mg/kg body weight to about 150 mg/kg body weight. In some embodiments, the dosage is 50 mg/kg body weight.

One of ordinary skill in the art will appreciate that the dosage of ritanserin, a ritanserin analog, or other active compound(s) being administered will depend on the condition being treated, the particular compound, and other clinical factors such as age, sex, weight, and health of the subject being treated, the route of administration of the compound(s), and the type of composition being administered (tablet, gel cap, capsule, solution, suspension, inhaler, aerosol, elixir, lozenge, injection, patch, ointment, cream, etc.). It is to be understood that the presently disclosed subject matter has application for both human and veterinary use.

The presently disclosed subject matter further encompasses biologically active analogs, homologs, derivatives, and modifications of the compounds of the presently disclosed subject matter. Methods for the preparation of such compounds are known in the art.

III. Compositions and Routes of Administration

The presently disclosed subject matter provides, in some embodiments, compositions comprising ritanserin or a ritanserin analog. In some embodiments, such compositions can be provided in the form of pharmaceutical formulations suitable for administration to a subject in need of treatment for a disease or disorder.

In some embodiments, the presently disclosed subject matter provides compositions comprising multiple active compounds (i.e., multiple medications). In some embodiments, combinations of multiple active compounds can be used in a single combined formulation, or used singly (e.g., provided in multiple separate formulations), within specific dosing ranges to treat cancer. In some embodiments, two or more medications are administered. In some embodiments, three or more medications are administered.

When active compounds of the presently disclosed subject matter are to be administered at the same time, they can be administered in a formulation containing more than one compound.

In some embodiments, the presently disclosed subject matter provides a composition comprising ritanserin or a ritanserin analog and at least one additional pharmaceutically active compound. In some embodiments, the additional pharmaceutically active compound is an anti-cancer agent.

Thus, in some embodiments, the presently disclosed subject matter provides a composition comprising ritanserin or a ritanserin analog and at least one additional pharmaceutically active compound (e.g., an anti-cancer agent), wherein the ritanserin or ritanserin analog is a compound of the formula:

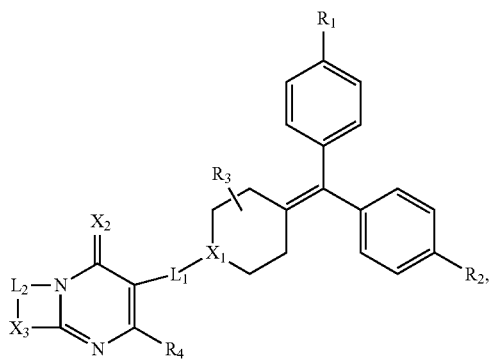

wherein:
each of $R_1$ and $R_2$ is independently selected from the group consisting of alkyl, substituted alkyl, —$CF_3$, alkoxy, hydroxyl, amino, and halo;
$R_3$ is hydrogen, hydroxyl, or alkoxy;
$R_4$ is hydrogen or alkyl;
$X_1$ is N or CH;
$X_2$ is O, $CH_2$, or NH;
$X_3$ is —S—, —$CH_2$—, or —$CR_5$=$CR_6$—;
$L_1$ is alkylene, optionally $C_1$-$C_5$ alkylene; and
$L_2$ is —$CH_2CH_2$—, $CH_2CH_2CH_2$—, or $CR_7$=$CR_8$—, wherein each $R_5$, $R_6$, $R_7$, and $R_8$ is independently H, halo, amino, alkyl or substituted alkyl. In some embodiments, the at least one additional anti-cancer agent is known in the art in the treatment of GBM and/or melanoma. In some embodiments, the presently disclosed subject matter provides a composition comprising ritanserin or a ritanserin analog and a second active compound that provides synergistic effect with ritanserin or a ritanserin analog in the treatment of cancer. In some embodiments, the composition comprises ritanserin or a ritanserin analog and at least one of temozolomide, chloroquine, bevacizumab, imatinib, and an immunotherapeutic agent. In some embodiments, the composition comprises ritanserin or a ritanserin analog, and either temozolomide or chloroquine. In some embodiments, the composition comprises ritanserin or a ritanserin analog, temozlomide, and chloroquine.

In some embodiments, the presently disclosed subject matter provides a composition comprising ritanserin and at least one additional anti-cancer agent.

In some embodiments, the at least one additional anti-cancer agent is known in the art in the treatment of GBM and/or melanoma. In some embodiments, the presently disclosed subject matter provides a composition comprising ritanserin and a second active compound that provides synergistic effect with ritanserin in the treatment of cancer. In some embodiments, the composition comprises ritanserin and at least one of temozolomide, chloroquine, bevacizumab, imatinib, and an immunotherapeutic agent. In some embodiments, the composition comprises ritanserin and either temozolomide or chloroquine. In some embodiments, the composition comprises ritanserin, temozlomide, and chloroquine.

In some embodiments, the presently disclosed composition also comprises a pharmaceutically acceptable carrier and/or excipient. Pharmaceutically acceptable excipients can be selected from the group including, but not limited to, granulating agents, binding agents, lubricating agents, disintegrating agents, sweetening agents, glidants, anti-adherents, anti-static agents, surfactants, anti-oxidants, gums, coloring agents, flavouring agents, coating agents, plasticizers, preservatives, suspending agents, emulsifying agents, spheronization agents and combinations thereof.

Based on the unexpected discoveries described herein, one of ordinary skill in the art can appreciate that the compounds disclosed herein as useful for combination drug therapy and/or as having synergistic effects can in some instances be used singly instead of as part of a combination. Additionally, based on the present disclosure, one of ordinary skill in the art will also appreciate that the active compounds described herein as useful for combination drug therapy can in some instances be used in any combination. Until the present discovery of useful combination therapies as disclosed herein, one or ordinary skill in the art would not have had such an appreciation.

In some embodiments, at least one of the active compounds being administered is administered at least once a day. In some embodiments, it is administered at least twice a day. In some embodiments, it is administered up to five times a day. In some embodiments, it is administered up to five times a week. In some embodiments, it is administered at least once a week. In some embodiments, it is administered at least once a month.

In some embodiments, at least two or at least three different active compounds are administered to the subject. It will be appreciated by one of ordinary skill in the art that the multiple active compounds, preferably three or more active compounds, being administered do not necessarily have to be administered at the same time or in equal doses. In some embodiments, the active compounds being administered as part of the drug combination therapy are separately administered. In some embodiments, a first active compound is administered before a second or third active compound is administered. In some embodiments, a first active compound and a second active compound are administered nearly simultaneously, while a third active compound is administered at a different time. In some embodiments, the first active compound is administered subsequent to administration of a second active compound or third active compound.

The presently disclosed subject matter further provides pharmaceutical compositions comprising active compounds as described herein. The pharmaceutical composition can comprise one or more active compounds, and biologically active analogs, homologs, derivatives, modifications, and pharmaceutically acceptable salts thereof, and a pharmaceutically acceptable carrier. In some embodiments, the active compounds are administered as a pharmaceutical composition.

The route of administration can vary depending on the type of compound being administered. In one aspect, the active compounds are administered via routes such as oral, topical, rectal, intramuscular, intramucosal, intranasal, inhalation, ophthalmic, and intravenous.

The presently disclosed subject matter further provides for administration of an active compound or compounds as a controlled-release formulation.

The combinations of drugs can be administered in formulations that contain all drugs being used, or the drugs can be administered separately. In some cases, it is anticipated that multiple doses/times of administration will be useful. Additionally, for some treatment regimens, at least two active compounds will be used. In some embodiments, at least three compounds will be administered. The presently disclosed subject matter further provides for varying the length of time of treatment.

In some embodiments, the results of treating a subject with a combination of two or more active compounds are additive compared with the effects of using any of the compounds alone. This does not mean that if three or more active compounds are administered that the results will be additive as to the combination of all drugs, just two or more. In some embodiments, the effects seen when using two or more active compounds are greater than when using any of the compounds alone.

In some embodiments, the results of treating a subject with a combination of two or more active compounds as described herein are synergistic compared with the effects of using the compounds alone, at least with regard to two compounds.

Additional compounds can be used to treat subjects according to the presently disclosed subject matter. In addition to the combination treatment of at least two drugs, or at least three drugs, described above, the presently disclosed subject matter further provides for the administration of at least one additional active compound or treatment to treat diseases and disorders. Thus, in some embodiments, four, five, six, seven or more compounds and treatments can be used in combination to treat a subject.

The presently disclosed subject matter provides for multiple methods for delivering the active compounds. The compounds can be provided, for example, as pharmaceutical compositions in multiple formats as well, including, but not limited to, tablets, capsules, pills, lozenges, syrups, ointments, creams, elixirs, suppositories, suspensions, inhalants, injections (including depot preparations), and liquids.

In some embodiments, a first active compound and a second active compound are administered nearly simultaneously. In some embodiments, a first active compound is administered prior to the second compound. In some embodiments, the first active compound is administered subsequent to the second compound. If three or more active compounds are administered, one of ordinary skill in the art will appreciate that the three or more active compounds can be administered simultaneously or in varying order.

In some embodiments disclosed herein, an individual is given a pharmaceutical composition comprising a combination of two or more active compounds.

In some of these embodiments, each compound is a separate chemical entity. However, in some embodiments, the at least two compounds can be joined together by a chemical linkage, such as a covalent bond, so that the at least two different active compounds form separate parts of the same molecule. In some embodiments, the chemical linkage is selected such that after entry into the body, the linkage is broken, such as by enzymatic action, acid hydrolysis, base hydrolysis, or the like, and the two separate active compounds are then formed.

Data from previous structure-activity relationship (SAR) studies within the art can be used as a guide to determine which compounds to use and the optimal position or positions on the molecules to attach the tether such that potency and selectivity of the active compounds can remain high. The tether or linker moiety can be chosen from among those of demonstrated utility for linking bioactive molecules together. Disclosed herein are representative compounds that can be attached together in different combinations to form heterobivalent therapeutic molecules.

Examples of linkers reported in the scientific literature include methylene ($CH_2$), linkers (see Hussey et al, 2003; and Tamiz et al., 2001), oligo ethyleneoxy $O(-CH_2CH_2O-)_n$ units used to link naltrexamine to other opioids, glycine oligomers of the formula $-NH-(COCH_2NH)_nCOCH_2CH_2CO-(NHCH_2CO)_nNH-$ used to link opioid antagonists and agonists together (see Portoghese et al., 1982; and Portoghese et al., 1986), hydrophilic diamines used to link opioid peptides together (see Stepinski et al., 1991), rigid double stranded DNA spacers (Paar et al., 2002) and the biodegradable linker poly(L-lactic acid). See Klok et al., 2002. The attachment of the tether to a compound can result in the compound achieving a favorable binding orientation. The linker itself can be biodegradable or cannot be biodegradable. The linker can take the form of a prodrug and be tunable for optimal release kinetics of the linked drugs. The linker can be either conformationally flexible throughout its entire length or else a segment of the tether can be designed to be conformationally restricted. See Portoghese et al., 1986.

The routes of administration, dosage amounts, and dosage forms described herein can be utilized for the administration of active compounds or pharmaceutically acceptable salts thereof for the treatment of cancer. Suitable forms of the compounds for use in biologically active compositions and methods of the presently disclosed subject matter include its pharmaceutically acceptable salts, polymorphs, solvates, hydrates, and prodrugs.

Administration of an effective amount of at least two active compounds, or pharmaceutically acceptable salts thereof, whether alone or in combination with a further therapeutic agent or treatment, to a subject can detectably treat cancer in the subject. In exemplary embodiments, administration of at least two active compounds, or pharmaceutically acceptable salts thereof, whether alone or in combination with additional therapeutic agents or treatments, can yield a reduction in tumor volume by at least about 10%, 20%, 30%, 50% or greater, up to about 75-90%, or about 95% or greater.

The present compositions can optionally comprise a suitable amount of a pharmaceutically acceptable vehicle so as to provide the form for proper administration to the patient.

Included within the scope of the presently disclosed subject matter are various individual anomers, diastereomers and enantiomers as well as mixtures thereof. In addition, the active compounds described herein also include any pharmaceutically acceptable salts, for example: alkali metal salts, such as sodium and potassium; ammonium salts; monoalkylammonium salts; dialkylammonium salts; trialkylammonium salts; tetraalkylammonium salts; and tromethamine salts. Hydrates and other solvates of the compounds are included within the scope of the presently disclosed subject matter.

In some embodiments, a composition of the presently disclosed subject matter can comprise one compound. In some embodiments, a composition of the presently disclosed subject matter can comprise more than one compound. In some embodiments, additional drugs or compounds useful for treating other disorders can be part of the composition. In some embodiments, a composition comprising only one compound can be administered at the same time as another composition comprising at least one other compound. In some embodiments, the different compositions can be administered at different times from one another. When a composition comprises only one compound, an additional composition comprising at least one additional compound can also be used.

The pharmaceutical compositions useful for practicing the presently disclosed subject matter can be, for example, administered to deliver a dose of between 1 ng/kg/day and 100 mg/kg/day.

Pharmaceutical compositions that are useful in the methods of the presently disclosed subject matter can be administered, for example, systemically in oral solid formulations, or as ophthalmic, suppository, aerosol, topical or other similar formulations. In addition to the appropriate compounds, such pharmaceutical compositions can contain pharmaceutically-acceptable carriers and other ingredients known to enhance and facilitate drug administration. Other possible formulations, such as nanoparticles, liposomes, resealed erythrocytes, and immunologically based systems can also be used to administer an appropriate compound, or an analog, modification, or derivative thereof according to the methods of the presently disclosed subject matter.

As used herein, "prodrug" refers to an agent that is converted into the parent drug in vivo. Prodrugs are often useful because, in some situations, they can be easier to administer than the parent drug. They can, for instance, be bioavailable by oral administration whereas the parent is not. The prodrug can also have improved solubility in pharmaceutical compositions over the parent drug, or can demonstrate increased palatability or be easier to formulate. An example, without limitation, of a prodrug would be a prodrug of an alcohol or carboxylic acid active parent compound which is administered as an ester (the "prodrug") to facilitate transmittal across a cell membrane where water solubility is detrimental to mobility but which then is metabolically hydrolyzed to the carboxylic acid or alcohol, i.e., the active entity/parent compound, once inside the cell where water-solubility is beneficial. A further example of a prodrug might be a short peptide (polyaminoacid) bonded to a carboxylic acid group of a parent compound where the peptide is metabolized to provide the active moiety.

The presently disclosed subject matter encompasses the preparation and use of pharmaceutical compositions comprising a compound useful for treatment of the diseases disclosed herein as an active ingredient. Such a pharmaceutical composition can consist of the active ingredient alone, in a form suitable for administration to a subject, or the pharmaceutical composition can comprise the active ingredient and one or more pharmaceutically acceptable carriers, one or more additional ingredients, or some combination of these. The active ingredient can be present in the pharmaceutical composition in the form of a physiologically acceptable ester or salt, such as in combination with a physiologically acceptable cation or anion, as is well known in the art.

The formulations of the pharmaceutical compositions described herein can be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the presently disclosed subject matter is contemplated include, but are not limited to, humans and other primates, mammals including commercially relevant mammals or mammals kept as pets, such as cattle, pigs, horses, sheep, cats, and dogs, and birds including commercially relevant birds and birds kept as pets, such as chickens, ducks, geese, parrots, and turkeys.

One type of administration encompassed by the methods of the presently disclosed subject matter is parenteral administration, which includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, and intrasternal injection, and kidney dialytic infusion techniques Pharmaceutical compositions that are useful in the methods of the presently disclosed subject matter can be prepared, packaged, or sold in formulations suitable for oral, rectal, vaginal, parenteral, topical, pulmonary, intranasal, inhalation, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the presently disclosed subject matter can be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject, or a convenient fraction of such a dosage such as, for example, one-half or one-third of such a dosage.

The relative amounts of the active ingredient, the pharmaceutically acceptable carrier, and any additional ingredients in a pharmaceutical composition of the presently disclosed subject matter will vary, depending upon the identity, size, and condition of the subject treated and further depending upon the route by which the composition is to be administered. By way of example, the composition cam comprise between 0.1% and 100% (w/w) active ingredient.

In addition to the active ingredient, a pharmaceutical composition of the presently disclosed subject matter can further comprise one or more additional pharmaceutically active agents. Particularly contemplated additional agents include anti-cancer agents, anti-emetics, scavengers (e.g., cyanide and cyanate scavengers), pain relievers, and immunotherapeutic agents.

Controlled- or sustained-release formulations of a pharmaceutical composition of the presently disclosed subject matter can be made using conventional technology.

A formulation of a pharmaceutical composition of the presently disclosed subject matter suitable for oral administration can be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets can be non-coated or can be coated using known methods to achieve delayed disintegration in the gastrointestinal tract of a subject, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin.

Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Lactulose can also be used as a freely erodible filler and is useful when the compounds of the presently disclosed subject matter are prepared in capsule form.

Liquid formulations of a pharmaceutical composition which are suitable for oral administration can be prepared, packaged, and sold either in liquid form or in the form of a dry product intended for reconstitution with water or another suitable vehicle prior to use.

Liquid suspensions can be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions can further comprise one or more additional ingredients including, but not limited to, suspending agents, dispersing or wetting agents, emulsifying agents, demulcents, preservatives, buffers, salts, flavorings, coloring agents, and sweetening agents. Oily suspensions can further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

In some embodiments, a preparation in the form of a syrup or elixir or for administration in the form of drops can comprise active ingredients together with a sweetener, which is preferably calorie-free, and which can further include methylparaben or propylparaben as antiseptics, a flavoring and a suitable color.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical compositions can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation can be prepared using known methods. Such formulations can be administered directly to a subject, used, for example, to form tablets, to fill capsules, or to prepare an aqueous or oily suspension or solution by addition of an aqueous or oily vehicle thereto. Each of these formulations can further comprise one or more of a dispersing or wetting agent, a suspending agent, and a preservative. Additional excipients, such as fillers and sweetening, flavoring, or coloring agents, can also be included in these formulations.

A pharmaceutical composition of the presently disclosed subject matter can also be prepared, packaged, or sold in the form of oil in water emulsion or a water-in-oil emulsion. The oily phase can be a vegetable oil such as olive or *arachis* oil, a mineral oil such as liquid paraffin, or a combination of these. Such compositions can further comprise one or more emulsifying agents including naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions can also contain additional ingredients including, for example, sweetening or flavoring agents.

A pharmaceutical composition of the presently disclosed subject matter can be prepared, packaged, or sold in a formulation suitable for rectal administration. Such a composition can be in the form of, for example, a suppository, a retention enema preparation, and a solution for rectal or colonic irrigation.

Suppository formulations can be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations can further comprise various additional ingredients including, but not limited to, antioxidants and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, and intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations can further comprise one or more additional ingredients including, but not limited to, suspending, stabilizing, or dispersing agents. In some embodiments of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation can comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil in water or water in oil emulsions such as creams, ointments or pastes, and solutions or suspensions. Topically-administrable formulations can, for example, comprise from about 1% to about 10% (w/w) active ingredient, although the concentration of the active ingredient can be as high as the solubility limit of the active ingredient in the solvent. Formulations for topical administration can further comprise one or more of the additional ingredients described herein.

A pharmaceutical composition of the presently disclosed subject matter can be prepared, packaged, or sold in a formulation suitable for pulmonary administration via the buccal cavity. Such a formulation can comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally, the propellant can constitute about 50% to about 99.9% (w/w) of the composition, and the active ingredient can constitute about 0.1% to about 20% (w/w) of the composition. The propellant can further comprise additional ingredients such as a liquid non-ionic or solid anionic surfactant or a solid diluent (preferably having a particle size of the same order as particles comprising the active ingredient).

Pharmaceutical compositions of the presently disclosed subject matter formulated for pulmonary delivery can also provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the presently disclosed subject matter.

Another formulation suitable for intranasal administration is a coarse powder comprising the active ingredient and having an average particle from about 0.2 to about 500 micrometers. Such a formulation is administered in the manner in which snuff is taken, i.e., by rapid inhalation through the nasal passage from a container of the powder held close to the nares.

Formulations suitable for nasal administration can, for example, comprise from about as little as about 0.1% (w/w) and as much as about 100% (w/w) of the active ingredient, and can further comprise one or more of the additional ingredients described herein.

A pharmaceutical composition of the presently disclosed subject matter can be prepared, packaged, or sold in a formulation suitable for buccal administration. Such formulations can, for example, be in the form of tablets or lozenges made using conventional methods, and can, for example, comprise about 0.1% to about 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

A pharmaceutical composition of the presently disclosed subject matter can be prepared, packaged, or sold in a formulation suitable for ophthalmic administration. Such formulations can, for example, be in the form of eye drops including, for example, a 0.1% to 1.0% (w/w) solution or suspension of the active ingredient in an aqueous or oily liquid carrier. Such drops can further comprise buffering agents, salts, or one or more other of the additional ingredients described herein. Other ophthalmically-administrable formulations which are useful include those which comprise the active ingredient in microcrystalline form or in a liposomal preparation.

A pharmaceutical composition of the presently disclosed subject matter can be prepared, packaged, or sold in a formulation suitable for intramucosal administration. The presently disclosed subject matter provides for intramucosal administration of compounds to allow passage or absorption of the compounds across mucosa. Such type of administration is useful for absorption orally (gingival, sublingual, buccal, etc.), rectally, vaginally, pulmonary, nasally, etc.

In some aspects, sublingual administration has an advantage for active ingredients which in some cases, when given orally, are subject to a substantial first pass metabolism and enzymatic degradation through the liver, resulting in rapid metabolization and a loss of therapeutic activity related to the activity of the liver enzymes that convert the molecule into inactive metabolites, or the activity of which is decreased because of this bioconversion.

In some cases, a sublingual route of administration is capable of producing a rapid onset of action due to the considerable permeability and vascularization of the buccal mucosa. Moreover, sublingual administration can also allow the administration of active ingredients which are not normally absorbed at the level of the stomach mucosa or digestive mucosa after oral administration, or alternatively which are partially or completely degraded in acidic medium after ingestion of, for example, a tablet.

Sublingual tablet preparation techniques known from the prior art are usually prepared by direct compression of a mixture of powders comprising the active ingredient and excipients for compression, such as diluents, binders, disintegrating agents and adjuvants. In an alternative method of preparation, the active ingredient and the compression excipients can be dry- or wet-granulated beforehand. In some embodiments, the active ingredient is distributed throughout the mass of the tablet. WO 00/16750 describes a tablet for sublingual use that disintegrates rapidly and comprises an ordered mixture in which the active ingredient is in the form of microparticles which adhere to the surface of water-soluble particles that are substantially greater in size, constituting a support for the active microparticles, the composition also comprising a mucoadhesive agent. WO 00/57858 describes a tablet for sublingual use, comprising an active ingredient combined with an effervescent system intended to promote absorption, and also a pH-modifier.

The compounds of the presently disclosed subject matter can be prepared in a formulation or pharmaceutical composition appropriate for administration that allows or enhances absorption across mucosa. Mucosal absorption enhancers include, but are not limited to, a bile salt, fatty acid, surfactant, or alcohol. In specific embodiments, the permeation enhancer can be sodium cholate, sodium dodecyl sulphate, sodium deoxycholate, taurodeoxycholate, sodium glycocholate, dimethylsulfoxide or ethanol. In some embodiments, a compound of the presently disclosed subject matter can be formulated with a mucosal penetration enhancer to facilitate delivery of the compound. The formulation can also be prepared with pH optimized for solubility, drug stability, and absorption through mucosa such as nasal mucosa, oral mucosa, vaginal mucosa, respiratory, and intestinal mucosa.

To further enhance mucosal delivery of pharmaceutical agents within the presently disclosed subject matter, formulations comprising the active agent can also contain a hydrophilic low molecular weight compound as a base or excipient. Such hydrophilic low molecular weight compounds provide a passage medium through which a water-soluble active agent, such as a physiologically active peptide or protein, can diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10000 and preferably not more than 3000. Exemplary hydrophilic low molecular weight compounds include polyol compounds, such as oligo-, di- and monosaccharides such as sucrose, mannitol, lactose, L-arabinose, D-erythrose, D-ribose, D-xylose, D-mannose, D-galactose, lactulose, cellobiose, gentibiose, glycerin, and polyethylene glycol. Other examples of hydrophilic low molecular weight compounds useful as carriers within the presently disclosed subject matter include N-methylpyrrolidone, and alcohols (e.g., oligovinyl alcohol, ethanol, ethylene glycol, propylene glycol, etc.). These hydrophilic low molecular weight compounds can be used alone or in combination with one another or with other active or inactive components of the intranasal formulation.

When a controlled-release pharmaceutical preparation of the presently disclosed subject matter further contains a hydrophilic base, many options are available for inclusion. Hydrophilic polymers such as a polyethylene glycol and polyvinyl pyrrolidone, sugar alcohols such as D-sorbitol and xylitol, saccharides such as sucrose, maltose, lactulose, D-fructose, dextran, and glucose, surfactants such as polyoxyethylene-hydrogenated castor oil, polyoxyethylene polyoxypropylene glycol, and polyoxyethylene sorbitan higher fatty acid esters, salts such as sodium chloride and magnesium chloride, organic acids such as citric acid and tartaric acid, amino acids such as glycine, beta-alanine, and lysine hydrochloride, and aminosaccharides such as meglumine are given as examples of the hydrophilic base. Polyethylene glycol, sucrose, and polyvinyl pyrrolidone are preferred and polyethylene glycol are further preferred. One or a combination of two or more hydrophilic bases can be used in the presently disclosed subject matter.

The presently disclosed subject matter contemplates pulmonary, nasal, or oral administration through an inhaler. In some embodiments, delivery from an inhaler can be a metered dose.

An inhaler is a device for patient self-administration of at least one active compound as described herein comprising a spray inhaler (e.g., a nasal, oral, or pulmonary spray inhaler) containing an aerosol spray formulation of at least one active compound and a pharmaceutically acceptable dispersant. In some embodiments, the device is metered to disperse an amount of the aerosol formulation by forming a spray that contains a dose of at least one active compound effective to treat a disease or disorder encompassed by the presently disclosed subject matter. The dispersant can be a surfactant, such as, but not limited to, polyoxyethylene fatty acid esters, polyoxyethylene fatty acid alcohols, and polyoxyethylene sorbitan fatty acid esters. Phospholipid-based surfactants also can be used.

In some embodiments, the aerosol formulation is provided as a dry powder aerosol formulation in which an active compound of the presently disclosed subject matter is present as a finely divided powder. The dry powder formulation can further comprise a bulking agent, such as, but not limited to, lactose, sorbitol, sucrose, and mannitol.

In some embodiments, the aerosol formulation is a liquid aerosol formulation further comprising a pharmaceutically acceptable diluent, such as, but not limited to, sterile water, saline, buffered saline and dextrose solution.

In some embodiments, the aerosol formulation further comprises at least one additional active compound as described herein in a concentration such that the metered amount of the aerosol formulation dispersed by the device contains a dose of the additional active compound in a metered amount that is effective to ameliorate the symptoms of disease or disorder disclosed herein when used in combination with at least a first or second active compound.

Compounds of the presently disclosed subject matter can be prepared in a formulation or pharmaceutical composition appropriate for nasal administration. In some embodiments, the compounds can be formulated with a mucosal penetration enhancer to facilitate delivery of the drug. The formulation can also be prepared with pH optimized for solubility, drug stability, absorption through nasal mucosa, and other considerations.

Capsules, blisters, and cartridges for use in an inhaler or insufflator cam be formulated to contain a powder mix of the pharmaceutical compositions provided herein; a suitable powder base, such as lactose or starch; and a performance modifier, such as 1-leucine, mannitol, or magnesium stearate. The lactose can be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration can further comprise a suitable flavor, such as menthol and levomenthol, or sweeteners, such as saccharin or saccharin sodium.

For administration by inhalation, the compounds for use according to the methods of the presently disclosed subject matter are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of e.g., gelatin for use in an inhaler or insufflator can be formulated containing a powder mix of the drugs and a suitable powder base such as lactose or starch.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which can be included in the pharmaceutical compositions of the presently disclosed subject matter are known in the art and described, for example in Genaro, ed., 1985, Remington's Pharmaceutical Sciences, Mack Publishing Co., Easton, Pa., which is incorporated herein by reference.

Typically, dosages of the active compounds of the presently disclosed subject matter which can be administered to an animal, preferably a human, range in amount from about 1.0 µg to about 100 g per kilogram of body weight of the animal. The precise dosage administered will vary depending upon any number of factors, including but not limited to, the type of animal and type of disease state being treated, the age of the animal and the route of administration. Preferably, the dosage of the active compound will vary from about 1 mg to about 10 g per kilogram of body weight of the animal. More preferably, the dosage will vary from about 10 mg to about 1 g per kilogram of body weight of the animal.

The active compounds can be administered to a subject as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

The presently disclosed subject matter also includes a kit comprising the active compound(s) and an instructional material that describes administration of the compound(s). In some embodiments, this kit comprises a (preferably sterile) solvent suitable for dissolving or suspending the composition or compositions of the presently disclosed subject matter prior to administering the composition(s) to the mammal.

As used herein, an "instructional material" includes a publication, a recording, a diagram, or any other medium of expression that can be used to communicate the usefulness of the active compounds in the kit for effecting alleviation of the various diseases or disorders recited herein. Optionally, or alternately, the instructional material can describe one or more methods of alleviating the diseases or disorders. The instructional material of the kit of the presently disclosed subject matter can, for example, be affixed to a container that contains an active compound or compounds or be shipped together with a container that contains the compound or compounds. Alternatively, the instructional material can be shipped separately from the container with the intention that the instructional material and the compound(s) be used cooperatively by the recipient.

One of ordinary skill in the art can determine the dose and term of treatment to be used.

When two or more compounds are to be administered, they can be administered in the same pharmaceutical composition or in separate pharmaceutical compositions. When administered in separate pharmaceutical compositions, they can be administered simultaneously or one can be administered first. The amount of time between administration of the different compounds can vary and can be determined by one of ordinary skill in the art. For example, the two compounds could be administered up to 10 minutes apart, up to 30 minutes apart, up to 1 hour apart, etc. In some embodiments, one or more of the compounds can be administered more than once. In some embodiments, a compound is administered at least twice. In some embodiments, a compound is administered at least five times. In some embodiments, the method is useful for low dose treatment. In some embodiments, the method is useful for short-term treatment.

One of ordinary skill in the art can determine the best route of administration of a pharmaceutical composition of the presently disclosed subject matter. For example, administration can be direct, enteral, or parenteral. Enteral includes, for example, oral and rectal administration. Parenteral includes, for example, intravenous administration. In some embodiments, administration is oral administration.

The presently disclosed subject matter further encompasses the use of therapeutically active homologs, analogs, and derivatives of the useful compounds of the presently disclosed subject matter.

The presently disclosed subject matter further provides for the use of a unit dose.

In some embodiments, at least one active compound of the presently disclosed subject matter can be administered in conjunction with another therapeutic agent. Additional therapeutic agents include, for example, antibiotics, anti-diarrheals, steroids, anti-inflammatories, other antimicrobials, and inducers of chemokines. In some embodiments, more than one therapeutic agent can be administered in conjunction with a therapeutic compound of the presently disclosed subject matter.

The presently disclosed subject matter further provides kits comprising active compounds, an applicator, and an instructional material for the use thereof.

EXAMPLES

The following Examples provide further illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Materials and Methods for the Examples

Purification of DGKα:

To obtain purified protein, 293T cells were cultured in DMEM containing 5% fetal calf serum and 1% penicillin/streptomycin (GIBCO™, Thermo Fisher Scientific, Waltham, Mass., United States of America). The cells were transiently transfected with 40 μg of pcDNA3-FLAG-DGKα plasmid/plate. The transfection was done using lipofectamine 2000 at a 2:1 ratio of DNA:lipofectamine. The cells were harvested and homogenized in lysis buffer (10 mM $Na_2HPO_4$, pH 7.4, 50 mM β-glucopyranose, 50 mM NaF, 1 mM EDTA, 1 mM EGTA, 0.02% Triton X-100, phenylmethylsulfonyl fluoride, leupeptine, and pepstatin). The cell homogenate was centrifuged at 16,000×g at 4° C. for 10 minutes. The supernatant was immunoprecipitated with anti-FLAG (M2) beads for 2 hours at 4° C. The beads were packed onto a screening column and washed five times with the lysis buffer. The protein was eluted with five successive 200 μl fractions of 0.5 mg/ml of FLAG peptide (LifeTein, LLC, Somerset, N.J., United States of America). The elution fractions containing DGKα were combined and dialyzed three times against 10 mM $Na_2HPO_4$ (pH 7.4), and 50 mM β-glucopyranose, 50 mM NaF, 1 mM EDTA, and 1 mM EGTA. The purified DGKs were quantified with UV absorbance and by comparing DGKα bands with bovine serum albumin standards on Coomassie-blue stained SDS-PAGE gels.

Preparation of Liposomes:

Lipids (phosphatidylcholine (PC), diacylglycerol (DAG), and phosphatidylserine PS)) were co-dissolved in chloroform, dried in vacuo to form a thin film and hydrated to a final concentration of 19 mM in 50 mM Tris-HCl, 100 mM NaCl (pH 8). The lipids were subjected to five freeze-thaw cycles and were extruded through a 100 nm diameter polycarbonate filter 11 times. The diameter of the liposomes was verified using a DynaPro® Dynamic Light Scattering instrument from Wyatt Technologies (Santa Barbara, Calif., United States of America). The final lipid composition of the liposomes was 5 mol % DAG, 20 mol % PS, and 75 mol % PC.

Kinase Assays:

The enzyme activity was assayed using a final reaction volume of 50 μl containing: 4.75 mM lipids and kinase buffer (100 mM NaCl, 50 mM Tris-HCl, 5 mM $MgCl_2$, 1 mM $CaCl_2$, 1 mM DTT). Reactions were initiated by the addition of 5 μl of 5 mM [γ-$^{32}$P]ATP and were allowed to proceed for 15 minutes at 25° C., then terminated with 250 μl MeOH 0.1N HCl, and then 500 μl of $CHCl_3$. The organic phase was washed twice with 1 M $MgCl_2$, and 250 μl of the organic phase was used to measure the extent of $^{32}$P incorporation into PA using an LS6500 Multi-Purpose Scintillation Counter (Beckman Coulter, Brea, Calif., United States of America). R59022 and ritanserin were dissolved to 20 mM in DMSO (0.5% (v/v), serially diluted in kinase buffer and 0.1% BSA (Sigma, St. Louis, Mo., United States of America) and added to the reaction mixtures.

Cell Lines:

U251 MG human glioblastoma, VMM39 human melanoma, GL261 mouse glioma, B16 mouse melanoma, and JWL578 human glioblastoma stem cell line were gifts from Howard Fine (Cornell University, Ithaca, N.Y., United States of America), Daniel Gioeli (University of Virginia, Charlottesville, Va., United States of America), Michael Olin (University of Minnesota, Minneapolis, Minn., United States of America), Vic Engelhard (University of Virginia, Charlottesville, Va., United States of America), and Jeongwu Lee (Cleveland Clinic, Cleveland, Ohio, United States of America), respectively. All cell lines are previously described and were maintained in appropriate serum-containing or serum-free medium. See Dominguez et al., 2013; Bullock et al., 2001; Kim et al., 2012; Olin et al., 2010; and Roller et al., 2012. U251MG, VMM39, GL261 and B16 were tested for authenticity by ATCC in January 2016, and JWL578 was tested for human species origin in November 2014 and March 2015 by IDEXX Laboratories (Westbrook, Me., United States of America).

Pharmacological Reagents:

Ritanserin was obtained from Tocris Bioscience (Bristol, United Kingdom) or Sigma (St. Louis, Mo., United States of America). For in vitro experiments, ritanserin was dissolved in DMSO at 10 mM stock solution and maintained at −70° C. For in vivo experiments, ritanserin was dissolved in corn oil at 10 mg/ml and administered via oral gavage. Phosphatidic acid (Avanti Polar Lipids, Alabaster, Ala., United States of America) was suspended in 2 chloroform: 1 methanol at a stock concentration of 5 mM and maintained at −70° C. until use. Temozolomide (Merck & Co., Kenilworth, N.J., United States of America) and chloroquine (Sigma, St. Louis, Mo., United States of America) were dissolved in dH20 to 10 mM stock solution.

Figure 6A:
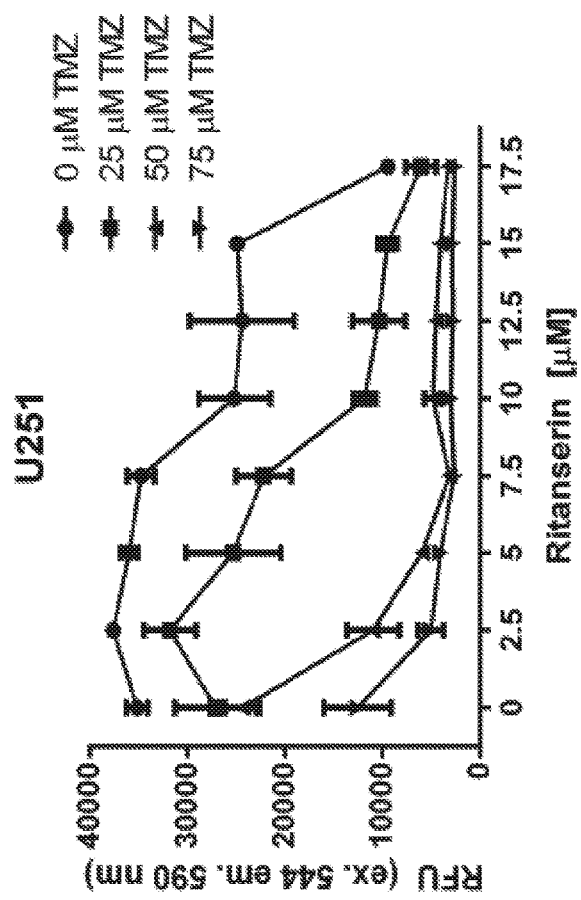
FIG. 6A is a graph of cell survival (as measured by relative fluorescence units (RFU)) in U251 human glioblastoma cells treated with a combination 0 to 17.5 micromolar (μM) ritanserin and 0 μM temozolomide (TMZ) (circles), 25 μM TMZ (squares), 50 μM TMZ (upward-pointing triangles) or 75 μM TMZ (downward-pointing triangles). Fluorescence data was taken from an alamarBlue assay performed after 4 days of incubation of the cells with the ritanserin and TMZ combinations.
Figure 6B:
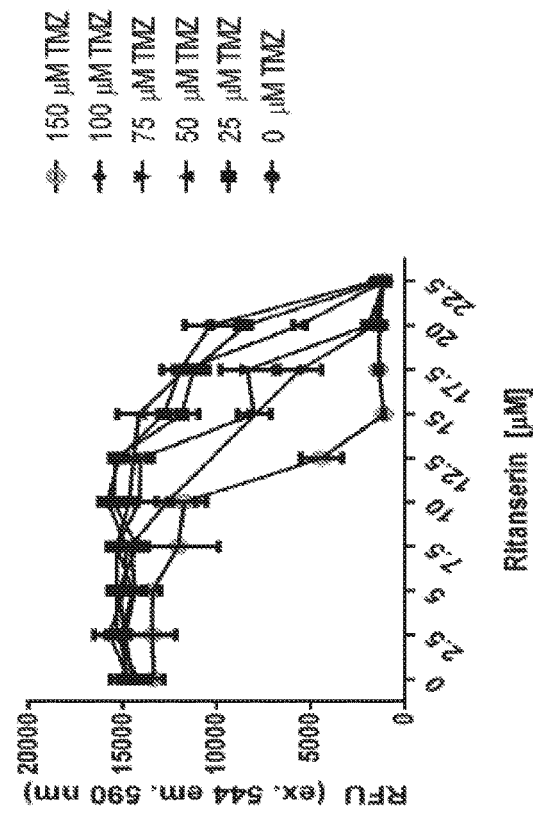
FIG. 6B is a graph of cell survival (as measured by relative fluorescence units (RFU)) in VMM39 human melanoma cells treated with a combination 0 to 22.5 micromolar (μM) ritanserin and 0 μM temozolomide (TMZ) (circles), 25 μM TMZ (squares), 50 μM TMZ (upward-pointing triangles), 75 μM TMZ (downward-pointing triangles), 100 μM TMZ (diamonds) or 150 μM TMZ (open squares). Fluorescence data was taken from an alamarBlue assay performed after 4 days of incubation of the cells with the ritanserin and TMZ combinations.
Figure 6C:
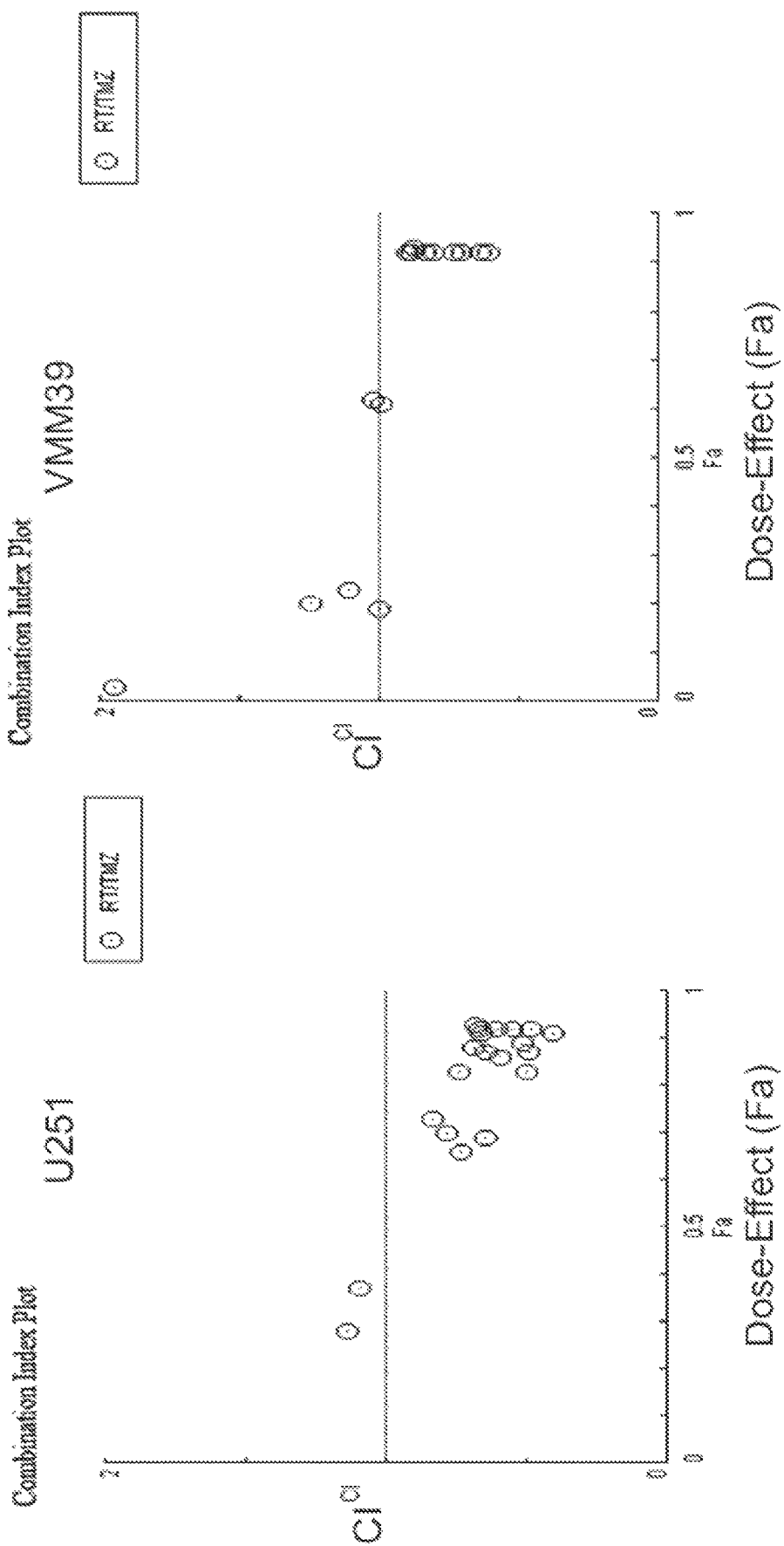
FIG. 6C is a pair of combination index plots prepared using the Chou-Talalay method for determining synergy from the data described for FIG. 6A (left) and FIG. 6B (right).
Figure 6D:
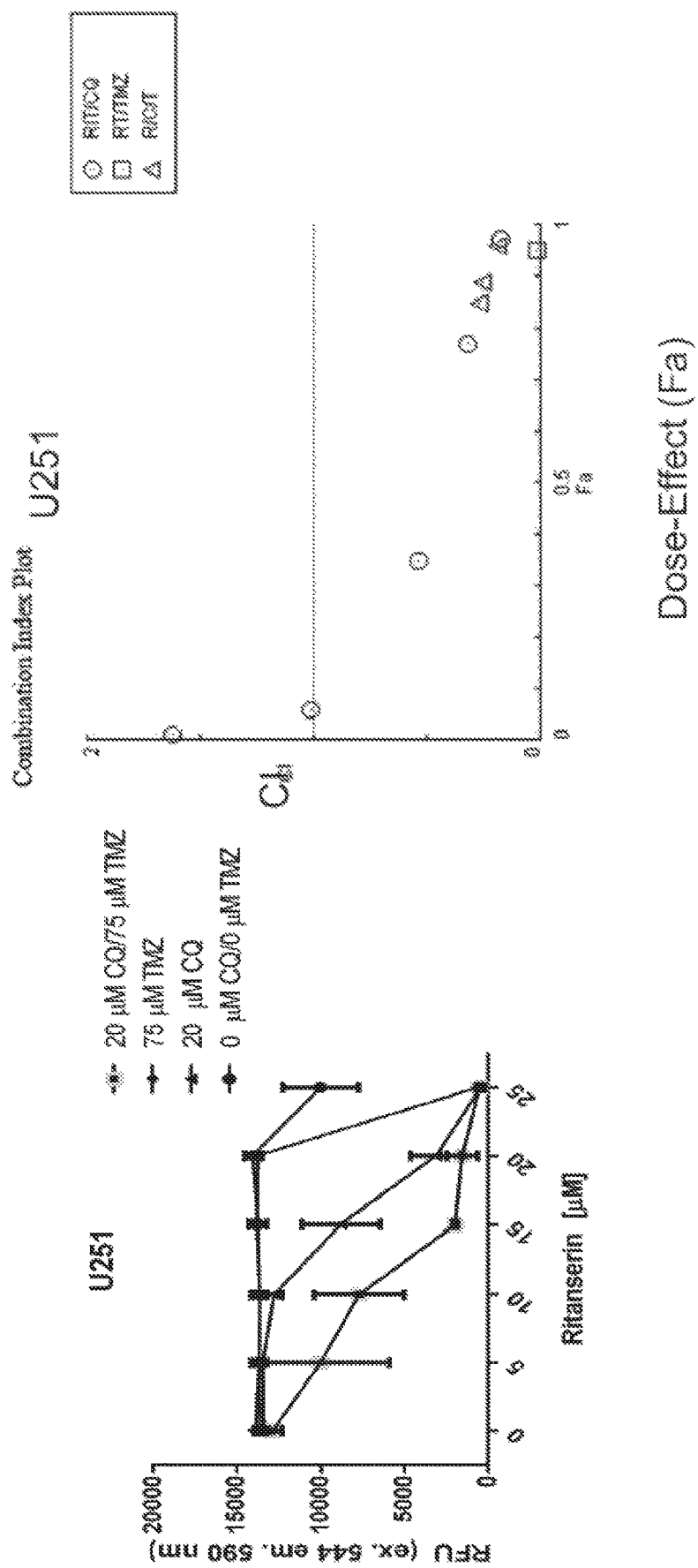
FIG. 6D is (left) a graph of cell survival (as measured by relative fluorescence units (RFU)) in U251 human melanoma cells treated with 0 to 25 micromolar (μM) ritanserin and a mixture of 20 μM chloroquine (CQ) and 75 μM temozolomide (TMZ) (squares), 75 μM TMZ (diamonds), 20 μM CQ (triangles) or ritanserin alone (i.e., 0 μM CQ and 0 μM TMZ) (circles); and (right) a combination index plot of synergy for the combination of ritanserin, CQ and TMZ prepared using the Chou-Talalay method. Fluorescence data was collected using alamarBlue assay after 4 days of treatment.

Cell Viability Assays:

In all cases, cells were collected as previously described (see Dominguez et al., 2013; and Kefas et al., 2013) two to four days post-treatment with ritanserin or vehicle (v:v DMSO). For cell counts, attached cells were collected and counted on a hemocytometer using TrypanBlue exclusion. For cell death assays, cells were stained with Annexin V-PE and 7-AAD according to the manufacturer's protocol (BD Pharmingen, Beckton Dickinson and Company, Franklin Lakes, N.J., United States of America). Single dye controls were used for compensation. Positive cell staining was measured using a FACSCALIBUR™ flow cytometer (Beckton Dickinson and Company, Franklin Lakes, N.J., United States of America) and analyzed with FlowJo software. To assess cell viability, alamarBlue cell health indicator (ThermoFisher Scientific, Waltham, Mass., United States of America) was added to cells and the fluorescent product measured after 3 to 4 hours in most cases, or after 24 hours in FIG. 6D (excitation 544 nm; emission 590 nm). Experiments were repeated several times per cell type.

Immunoblotting and Proteomics:

Immunoblotting was performed as previously described. See Dominguez et al., 2013; and Kefas et al., 2013. Antibodies were obtained from Cell Signaling Technology (Danvers, Mass., United States of America). Cells were lysed 24-72 hours post-treatment in 1× lysis buffer. The Human Phospho-Kinase Array kit (R&D Systems, Minneapolis, Minn., United States of America) was used to identify ritanserin targets. Immunoblots were performed with multiple replicates.

Luciferase Reporter Assays:

mTOR promoter reporter-RLuc or HIF-1α binding site-FLuc plasmids were transfected into serum-starved U251 and VMM39 one day after cell plating at 60-80% confluency using Fugene HD at 3:1 (Promega Corporation, Fitchburg, Wis., United States of America). Cells were fed several hours post-transfection and ritanserin was added. Cells were lysed after 36-48 hours and assayed with the Dual-Luciferase Reporter assay system kit (Promega Corporation, Fitchburg, Wis., United States of America) and Promega GloMax® 20/20 luminometer (Promega Corporation, Fitchburg, Wis., United States of America). Results were double-normalized using control empty vectors pRL and pGL3.

siRNA Transfection:

Lipofectamine® RNAiMAX transfection reagent (ThermoFisher Scientific, Waltham, Mass., United States of America) was utilized for siRNA transfection according to the producer's instructions with final siRNA concentration of 10 nanamoles per liter (nmol/L). DGKA siRNAs were as follows: a) custom DGKA siRNA: 5'GGAUUGACCCU-GUUCCUAA-3' (SEQ ID NO: 1); b) Dharmacon SMARTpool ON-TARGETplus (Dharmacon, Lafayette, Colo., United States of America). The data using the custom DGKA siRNA was generated with double transfection of glioblastoma stem cells three days apart.

Orthotopic Tumor Xenografts, Syngeneic Brain Tumor Mouse Models, and Subcutaneous Tumors:

Intracranial surgical implantation of tumor was as previously described. See Kefas et al., 2013. In brief, 400,000 U251 human glioblastoma or 50,000 GL261 mouse glioma suspended in 4 µL of serum-free DMEM were injected into anesthetized mice through a burr hole placed 1 mM caudal and 2 mM lateral to the bregma. Treatment for 8-9 mice per group began 6-7 days post-tumor implantation via oral gavage and continued daily. Magnetic resonance images were taken at 3 weeks post-tumor implantation to assess tumor volume, and volumes were calculated as previously described. See Kefas et al., 2013. Mice were euthanized at 20% weight loss or with the first sign of neurological impairment.

For subcutaneous tumors, 250,000 VMM39 human melanoma cells were injected subcutaneously into the left flank. After two weeks, tumors were measured daily using electronic calipers and tumor volume calculated. Mice were euthanized when tumors were greater than 15 mM in any dimension or greater than 1000 $mm^3$ in volume.

Statistics:

Statistical analyses were performed using GraphPad Prism 6 (GraphPad Software, Inc., La Jolla, Calif., United States of America) and CompuSyn (ComboSyn, Inc., Paramus, N.J., United States of America). One-way ANOVA with multiple comparisons to generate p-values was used to analyze single-drug in vitro experiments of more than two doses. Two-way ANOVA and Chou-Talalay model combination index was used to determine statistically likely drug synergies in combination experiments. For Chou-Talalay, percent inhibition (0.01 to 0.99) of alamarBlue signal was used to calculate average dose-responses (Fa) from three or more technical replicates per treatment group. Chou-Talalay combination indices (CI) less than 1 were considered to be synergistic, and less than 0.2 were an indication of strong synergy. See Chou, 2010. In vivo experiments were analyzed with the Kaplan-Meier survival function to determine p-values. Refutation of the null hypothesis was accepted for $p<0.05$.

Example 1

Inhibition of DGKα

DGKα activity was tested in vitro against increasing concentrations of both R59022 and ritanserin using liposomes and the purified enzyme.

The IC$_{50}$ values were 20 μM for R59022 and 9 μM for ritanserin. See FIGS. 1B and 1C. The IC$_{50}$ of R59022 obtained was similar to that found by others in assays using cellular homogenates. See Sato et al., 2013. Ritanserin is a known serotonin receptor inhibitor at very low nanomolar doses, but the presently disclosed data shows that it can be repurposed as an inhibitor of DGKα in the low micromolar range, as well.

Example 2

Ritanserin Cytotoxicity in Glioblastoma and Melanoma Cell Lines

Figure 2A:
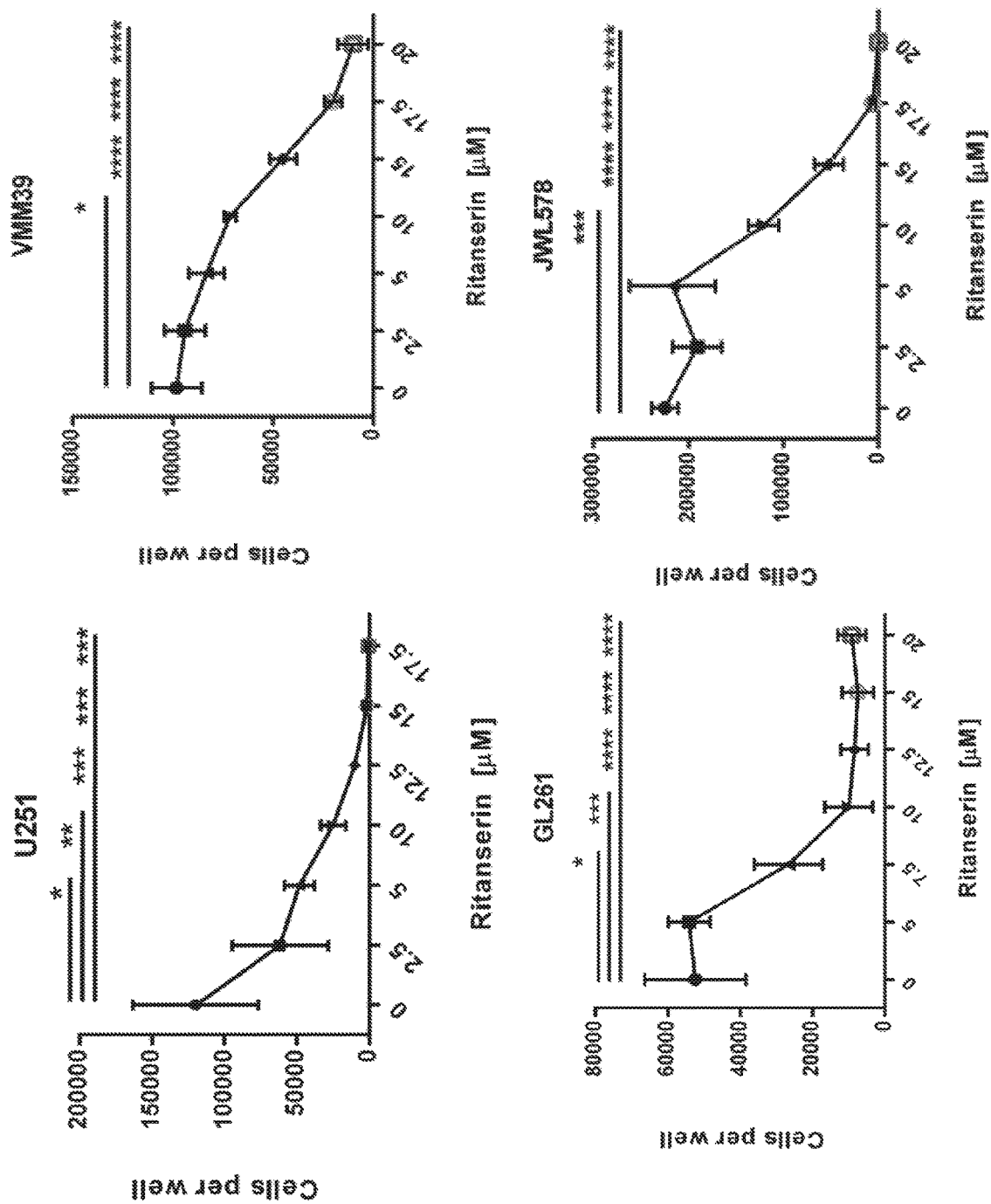
FIG. 2A is a series of graphs showing the cytotoxic effect of ritanserin on different cancer cell lines: U251 human glioblastoma cells (upper left), VMM39 human melanoma cells (upper right), GL261 murine glioma cells (lower left) and JWL578 human glioblastoma stem cells (lower right). The number of live cells was assessed four days post-treatment with ritanserin at concentrations between 0 micromolar (μM) and 17.5 or 20 μM. Error bars represent standard deviation. P values shown were generated from one-way analysis of variance (ANOVA) with Tukey's post-test for multiple comparisons ($p<0.05$, *, $p<0.01$, , $p<0.001$, *, $p<0.0001$, ****).
Figure 2E:
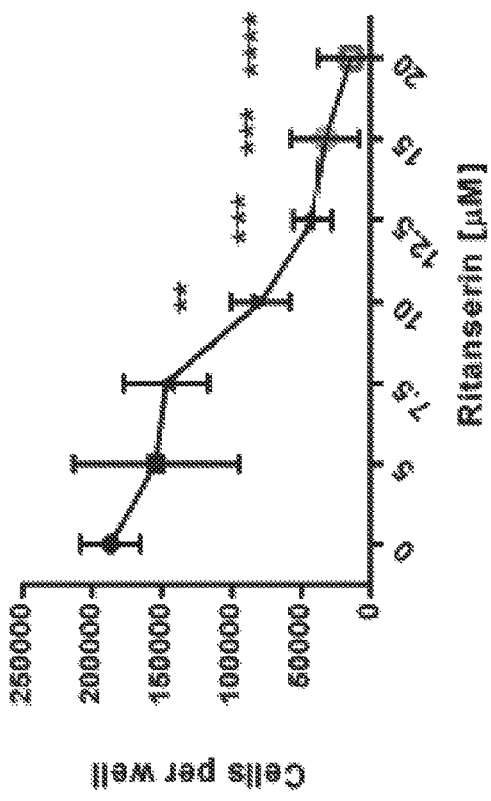
FIG. 2E is a graph showing the cytotoxic effects of ritanserin on murine B16 melanoma cells. The number of live cells was assessed four days post-treatment with ritanserin at concentrations between 0 micromolar (μM) and 20 μM. Error bars represent standard deviation. P values shown were generated from one-way analysis of variance (ANOVA) with Tukey's post-test for multiple comparisons ($p<0.05$, *, $p<0.01$, , $p<0.001$, *, $p<0.0001$, ****).

Several cancer cell lines were tested in vitro to determine whether ritanserin was cytotoxic. A single dose of ritanserin was sufficient to suppress cell growth in GBM lines U251 (human), GL261 (mouse), and JWL578 (human GBM stem cell line) with IC$_{50}$s 5-10 μM, very similar to previous results with R59022. See FIG. 2A. See also, Dominguez et al., 2013. Melanoma lines VMM39 (human) (see FIG. 2A) and B16 (mouse) (see FIG. 2E) were also affected, with IC$_{50}$s of 10-15 μM. See FIG. 2A. Data from alamarBlue assays, a measure of cellular viability, provided similar IC$_{50}$s. Immortalized astrocytes were viable above 20 μM ritanserin. These low-micromolar IC$_{50}$s are comparable to the concentrations at which ritanserin inhibits DGKα. See FIG. 1C.

Figure 2F:
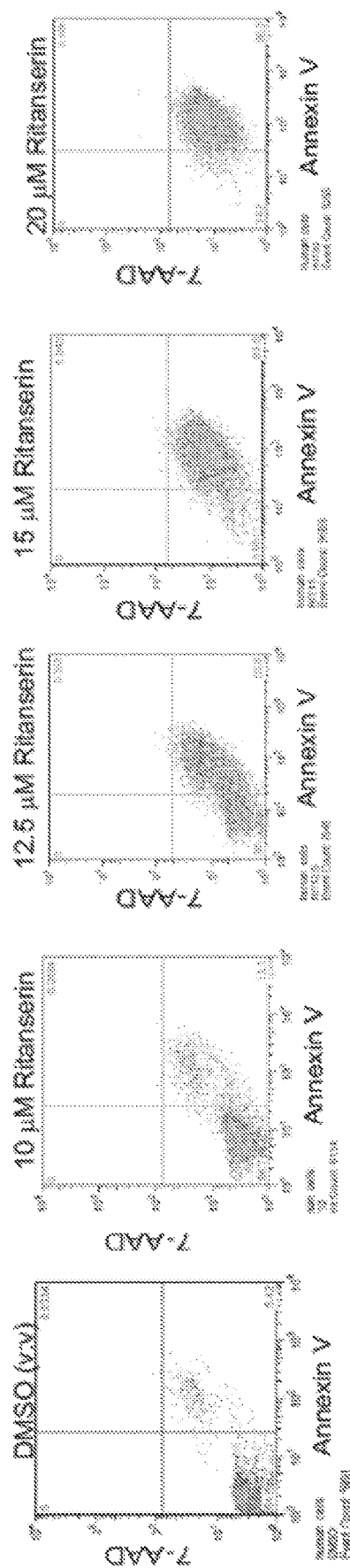
FIG. 2F is a series of plots of Annexin V positive VMM39 human melanoma cells after treatment with 10 micromolar (μM) ritanserin (second from left), 12.5 μM ritanserin (center), 15 μM ritanserin (second from right) or 20 μM ritanserin (right). For comparison, a plot of positive cells from a control sample treated only with vehicle (dimethylsulfoxide, DMSO) is also shown (left). The plots represent gating on live cells and 10,000 events were counted in three replicates per treatment.

To determine the mechanism of ritanserin cytotoxicity, ritanserin-treated cells were assayed for Annexin V-positivity as well as cellular permeability (with DNA dye 7-AAD). Both U251 GBM and VMM39 melanoma cell lines demonstrated increased Annexin V after ritanserin treatment compared to controls. See FIG. 2B and FIG. 2F. However, pre-treatment of cells with apoptosis inhibitor ZVAD-FMK did not rescue cell viability with ritanserin treatment. See FIG. 2G. These results indicated that ritanserin is directly cytotoxic to GBM, but that the mechanism might be inducing cell death upstream of caspase activation.

Given these data, chloroquine, an anti-autophagic reagent, and necrostatin-1, an anti-necroptotic agent, were tested in combination with ritanserin to determine whether either would rescue cell viability. Interestingly, ritanserin and chloroquine were synergistically cytotoxic. See FIG. 2C. LC3-II accumulated with ritanserin treatment or a combination of ritanserin and chloroquine treatment, suggesting autophagy induction. See FIG. 2C and FIG. 2H. Chloroquine is being investigated as a therapeutic adjunct in many cancers. See Kimura et al., 2013. The observed autophagy induction by ritanserin appears to be protective, given that chloroquine enhanced cancer cell killing by ritanserin. Necrostatin-1 did not show any rescue of ritanserin toxicity, suggesting that necroptosis is not a major mechanism of ritanserin cell death. See FIG. 2G. In U251 GBM, cleaved Poly-ADP ribose Polymerase (PARP) was observed in ritanserin-treated cells via western blot (see FIG. 2D), suggesting some degree of apoptosis.

Example 3

Rescue with Phosphatidic Acid and Suppression of DGKα Targets

Figure 3C:
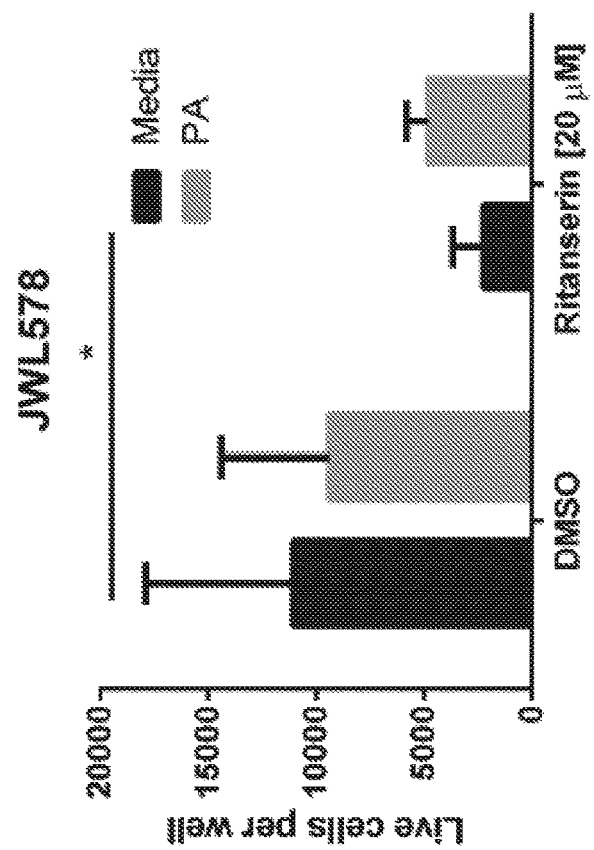
FIG. 3C a pair of graphs showing the effects of phosphatidic acid (PA) on ritanserin cytotoxicity in U251 human glioblastoma cells (left) and JWL578 human glioblastoma stem cells (right). U251 and JWL cells were incubated with 10 micromolar (μM) ritanserin or dimethylsulfoxide (DMSO) and either vehicle (media, black bars) or 100 μM PA (grey bars). Live cells were collected and counted 48 hours later. Student's T-test or one-way analysis of variance (ANOVA) with Tukey's post-test was used for analysis (p<0.1, *, p<0.01, , p<0.001, *).
Figure 3C:
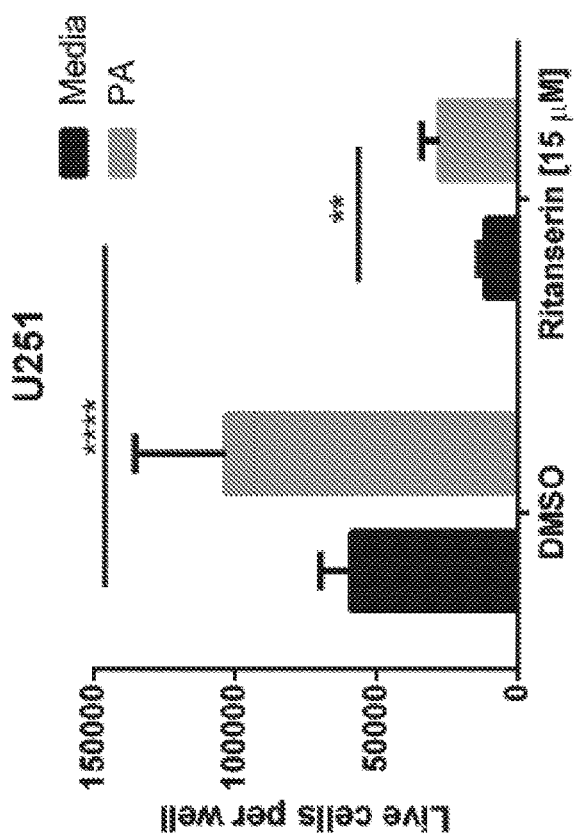

Given that ritanserin can inhibit DGKα in a kinase assay, rescue of ritanserin cytotoxicity in vitro was attempted with phosphatidic acid, the immediate downstream product of DGKα's ATP-dependent catalytic addition of a phosphate to diacylglycerol (DAG). The addition of phosphatidic acid (PA) to the culture medium substantially rescued ritanserin treatment in U251 and JWL578 GBM cells. See FIG. 3A and FIG. 3C.

To compare to previous findings that DGKα inhibition affects mTOR transcription, U251 and VMM39 were transfected with an mTOR promoter reporter and treated with ritanserin or vehicle. See FIG. 3B. Ritanserin treatment strongly decreased mTOR promoter activity. U251 treatment with ritanserin also resulted in a loss of HIF-1α reporter activity. See FIG. 3B. Ritanserin therefore appears to mimic R59022's effects on known DGKα targets in the mTOR and HIF-1α signaling pathways. See Dominguez et al., 2013.

Example 4

Sensitization to DNA-damaging Agents with Ritanserin

Figure 4A:
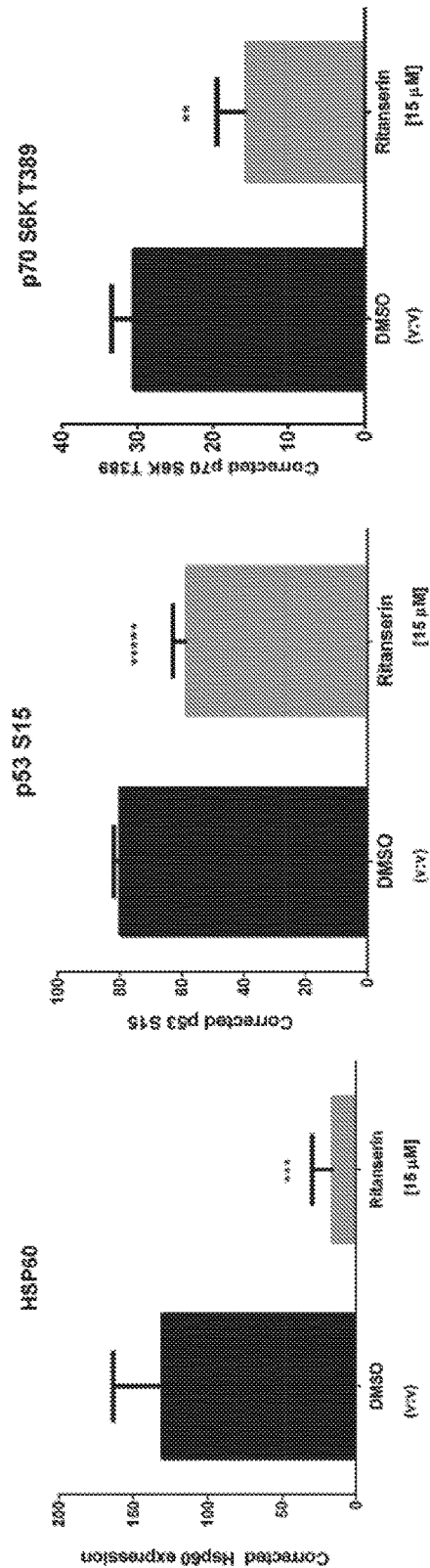
FIG. 4A is a series of graphs of expression of HSP60 (left), p53 S15 (center) or p70 S6K T389 (right) in U251 human glioblastoma cells treated with 15 micromolar (μM) ritanserin (grey bars) or dimethylsulfoxide (DMSO) (black bars). Cells were treated with ritanserin or DMSO and 24 hour lysates were used in a human phospho-proteomics assay. Data represents corrected average spot densities. Student's T-test was used for analysis, 2 replicates per group (p<0.01, , p<0.001, *, p<0.0001, ****).

A dot-blot proteomics assay was used to investigate ritanserin downstream targets. U251 treated with 15 μM ritanserin were lysed at 24 hours. See FIG. 4A. Several target proteins were substantially changed with ritanserin treatment. HSP60 decreased to 10% of baseline. Heat shock proteins are molecular targets in glioblastoma, and their loss prevents the unfolded protein response. See Ampie et al., 2015. HIF-1a and possibly mTOR up-regulate HSP60. P70 S6K phosphorylation at T389/T421 was decreased, as expected given DGKα activation of mTOR. See FIG. 4A.

Figure 4B:
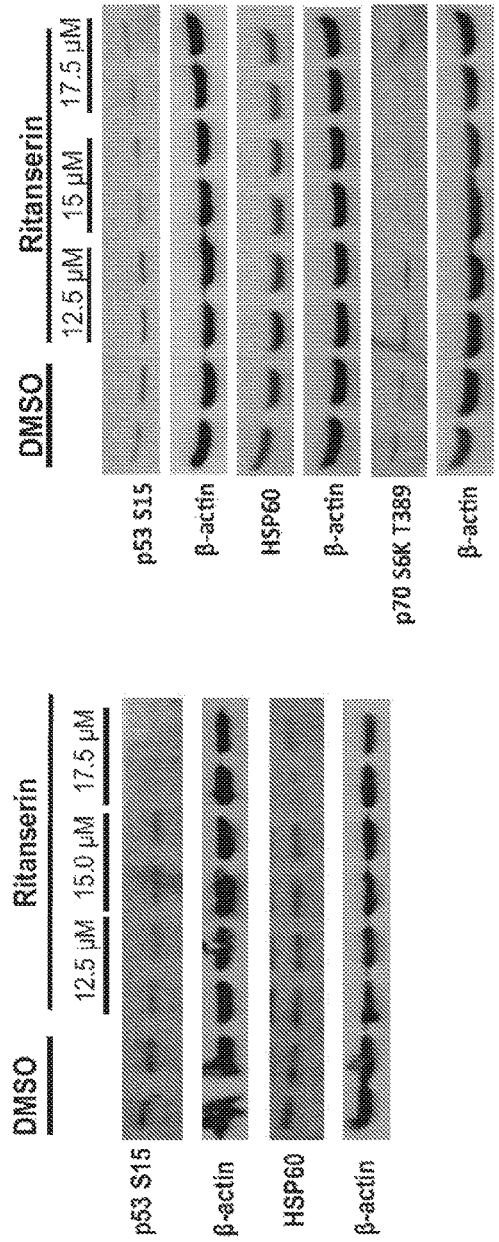
FIG. 4B is a group of radiographs of immunoblots confirming the protein targets for the data described for FIG. 4A using U251 human glioblastoma cells (left) and VMM39 human melanoma cells (right).

Decreased p53 S15 can cause chemosensitization to other cytotoxic reagents. p53 is hyper-phosphorylated after serine 15 phosphorylation in DNA-damaged cells as an anti-apoptotic, pro-transcriptional pathway, and antagonism of S15 phosphorylation is associated with increasing sensitivity to DNA-damaging agents. See Loughery et al., 2014; and Wittlinger et al., 2007. Immunoblots of extracts from both U251 and VMM39 cell lines confirmed that ritanserin decreases S15 phosphorylation. See FIG. 4B.

Example 5

In Vivo Anti-Cancer Activity

Figure 5C:
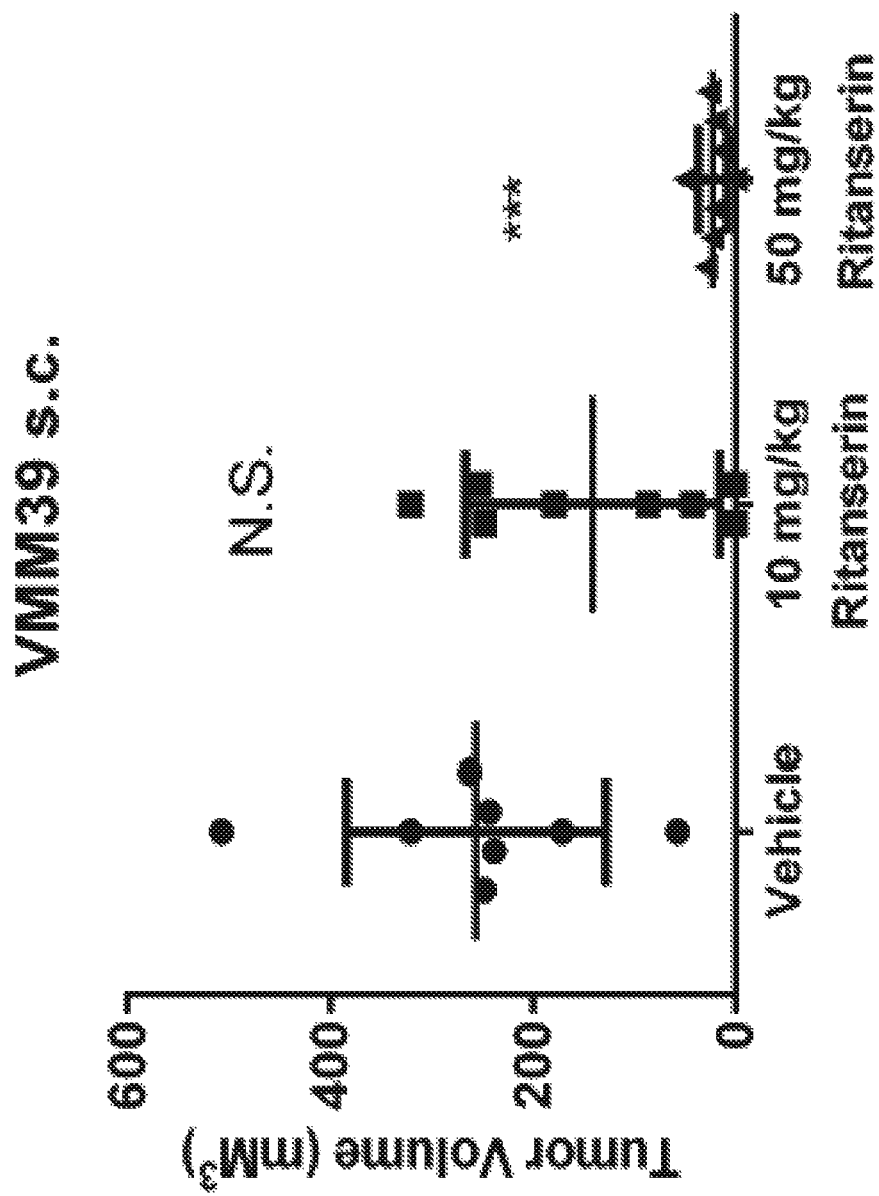
FIG. 5C is a graph showing tumor volume in athymic nu/nu mice implanted subcutaneously with VMM39 human melanoma cells and treated daily with 10 milligrams per kilogram (mg/kg) ritanserin (squares), 50 mg/kg ritanserin (triangles) or vehicle (corn oil, circles) after one week. Tumor volume was assayed using electronic calipers three weeks post implantation. Significance was calculated using Student's t-test (p<0.001, ***).

Since ritanserin is known to cross the blood-brain barrier and is orally bioavailable, glioblastoma survival experiments were undertaken in both orthotopic xenograft and syngeneic tumor models to determine the effect of oral ritanserin in vivo. Athymic nu/nu mice were injected with U251 cells and one week later began daily oral gavage treatment. 50 mg/kg daily dosing of ritanserin increased survival significantly. See FIG. 5A.

Figure 5D:
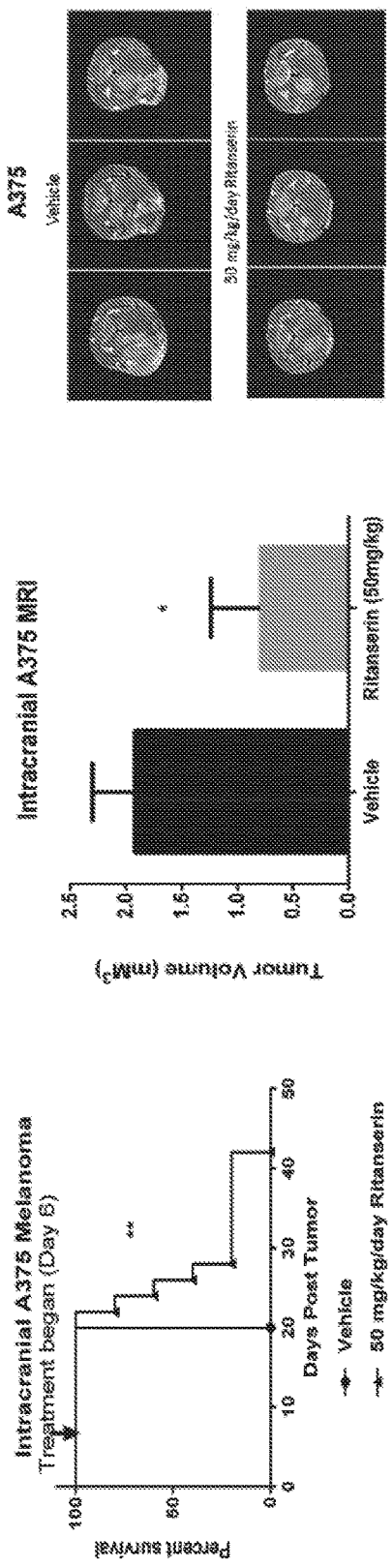
FIG. 5D is (left) a graph showing the survival curves of athymic nu/nu mice implanted intracranially with A375 human melanoma cells and treated with 50 milligrams per kilogram (mg/kg) ritanserin (triangles) or vehicle (corn oil) (circles) daily starting six days after implantation; (center) a graph showing the average tumor volumes three weeks post implantation in the same mice (vehicle treated mouse data shown in black bars and ritanserin treated mouse data shown in grey bars); and (right) the magnetic resonance imaging images of the mice performed three weeks post implantation.
Figure 5E:
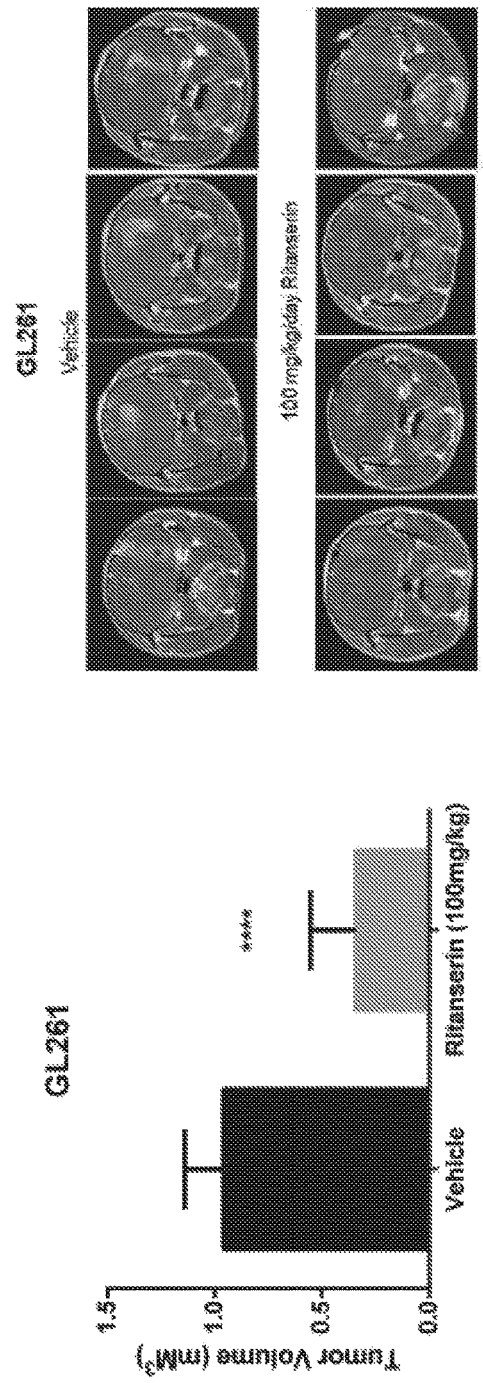
FIG. 5E is a graph showing tumor volumes of wild type C57BL/6 mice implanted intracranially with GL261 murine glioma cells and treated daily after six days with 100 milligrams per kilogram (mg/kg) ritanserin (grey bars) or vehicle (corn oil) (black bars). Magnetic resonance imaging (MRI) images of the mice are shown to the right of the graph.

DGKα inhibition decreases T-cell anergy. Thus, it is believed that a syngeneic, immunocompetent tumor model could show a stronger survival benefit. GL261 mouse glioma cells were implanted intracranially and treatment begun six days later. Ritanserin improved median survival to 64 days versus 36 days with vehicle. See FIG. 5B. Magnetic resonance imaging showed decreased tumor size compared to vehicle. See FIG. 5B. A subcutaneous melanoma tumor model delayed tumor formation in 50 mg/kg ritanserin-treated mice compared to vehicle and 10 mg/kg ritanserin-treated mice. See FIG. 5C. Ritanserin treatment also yielded decreases in tumor size and prolonged survival in other cell lines and xenograft models. See FIGS. 5D and 5E.

Example 6

Ritanserin Synergy with Temozolomide and/or Chloroquine

Figure 6E:
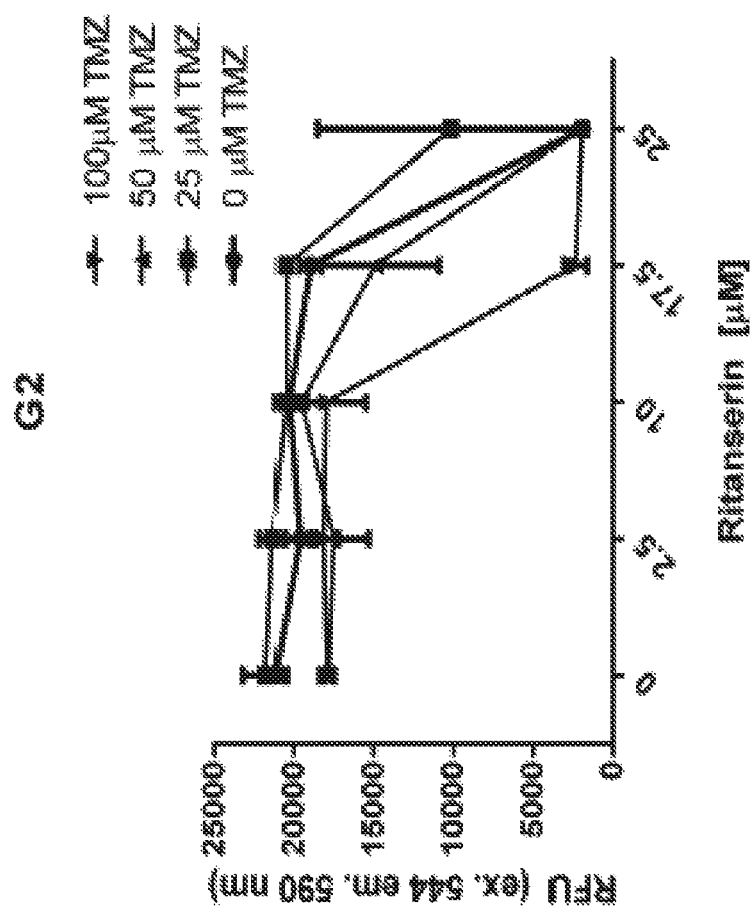
FIG. 6E is a graph of cell survival (as measured by relative fluorescence units (RFU)) in G2 mesenchymal glioblastoma stem cells treated with 0 to 25 micromolar (μM) ritanserin and 0 μM temozolomide (TMZ) (circles), 25 μM TMZ (squares), 50 μM TMZ (upward-pointing triangles), or 100 μM TMZ (downward-pointing triangles). Fluorescence data was taken from an alamarBlue assay performed after 4 days of incubation of the cells with the ritanserin and TMZ combinations.
Figure 7A:
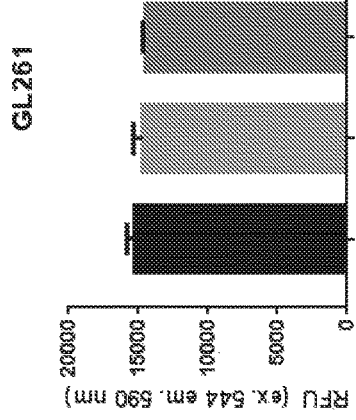
FIG. 7A is a graph showing the synergistic cytotoxic effects of chloroquine (CQ) and ritanserin (Rit) on U251 human glioblastoma cells. Cells were treated with 20 micromolar (μM) CQ and/or 10 μM Rit and then cell survival was analyzed 72-96 hours later by cell counting. For comparison, data (provided in cells per well) is also provided for cells treated with vehicle.
Figure 7B:
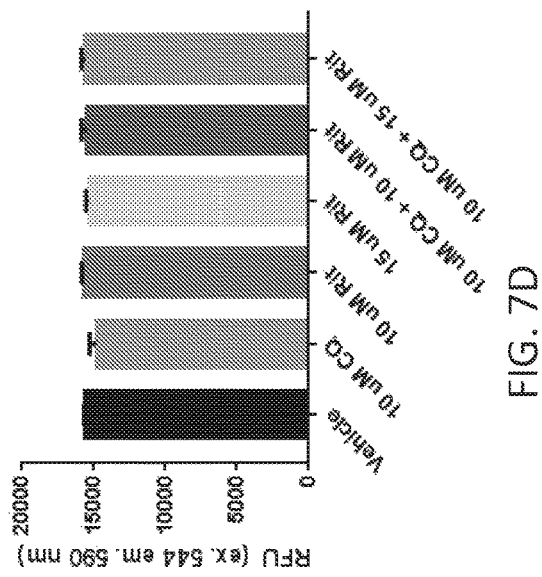
FIG. 7B is a graph showing the synergistic cytotoxic effects of chloroquine (CQ) and ritanserin (Rit) on GL261 mouse glioma cells. Cells were treated with 10 micromolar (μM) CQ and/or 10 μM Rit and then cell survival was analyzed 72-96 hours later via alamarBlue assay. For comparison, data (provided in relative fluorescence units (RFU)) is also provided for cells treated with vehicle.
Figure 7C:
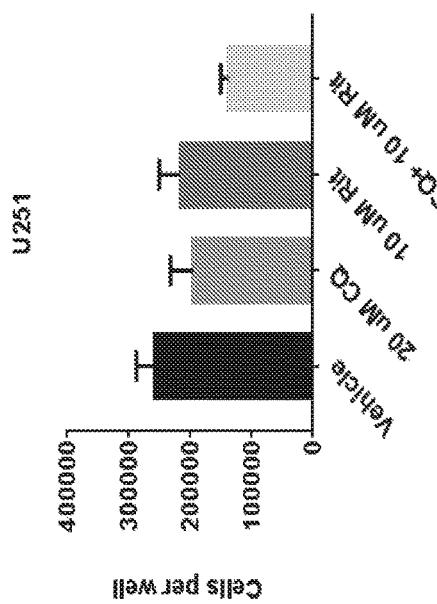
FIG. 7C is a graph showing the synergistic cytotoxic effects of chloroquine (CQ) and ritanserin (Rit) on GL261 mouse glioma cells. Cells were treated with 10 micromolar (μM) CQ and/or 10 μM Rit and then cell survival was analyzed 72-96 hours later by cell counting. For comparison, data (provided in cells per well) is also provided for cells treated with vehicle.
Figure 7D:
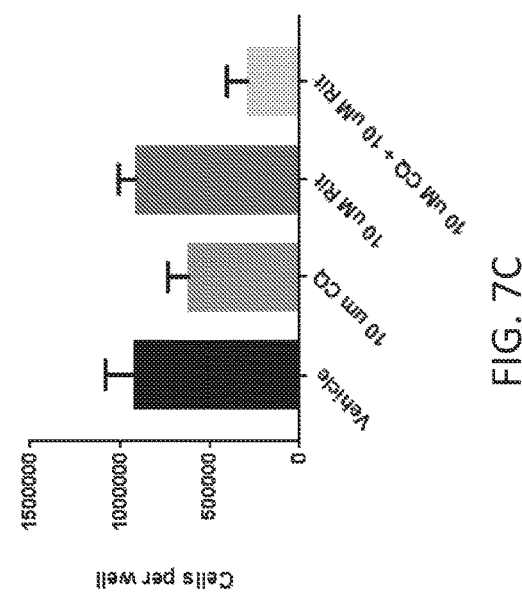
FIG. 7D is a graph showing the effects of chloroquine (CQ) and ritanserin (Rit) on immortalized astrocytes. Cells were treated with 10 micromolar (μM) CQ and/or 10 μM or 15 μM Rit and then cell survival was analyzed 72-96 hours later via alamarBlue assay. For comparison, data (provided in relative fluorescence units (RFU)) is also provided for cells treated with vehicle.

The presently disclosed data related to downstream targets of ritanserin suggest that ritanserin could synergize with known cytotoxic chemotherapies. Combination therapy experiments were performed using ritanserin and temozolomide, the standard-of-care chemotherapy for glioblastoma. Notably, ritanserin and temozolomide strongly synergized against U251 and VMM39 using alamarBlue assay. See FIGS. 6A and 6B. Concentrations of ritanserin as low as 7.5 µM with temozolomide at 50 µM decreased cellular viability by up to 90%, whereas single drug treatment at these concentrations did not impact cell viability significantly. Chou-Talalay analysis indicated synergy. See FIG. 6C. Similar results were also demonstrated in a G2 mesenchymal GBM stem cell line. See FIG. 6E. A ritanserin, temozolomide, and chloroquine combination experiment showed strong synergy as well in U251 cells. See FIG. 6D. This assay was developed over 24 hours to yield a very broad range of dose-effects (Fa). Temozolomide and chloroquine have previously been found to synergize against glioblastoma. See Hori et al., 2015; and Lee et al., 2015. Such synergy was also observed here at higher doses of chloroquine (50 µM).

As described in Example 2, ritanserin is also synergistically cytotoxic when used with chloroquine alone. See FIG. 2C. FIGS. 7A-7H provide additional data showing that ritanserin and chloroquine have cytotoxic synergy in glioblastoma and melanoma cells, but not astrocytes. Overall, the present results suggest ritanserin as a novel DGKα inhibitor, with promising activity alone or in combination against glioblastoma and melanoma cells, and could speed the translation of DGKα inhibition to the clinic.

Example 7

Toxicity for Mesenchymal Glioblastoma Subtype

Figure 8A:
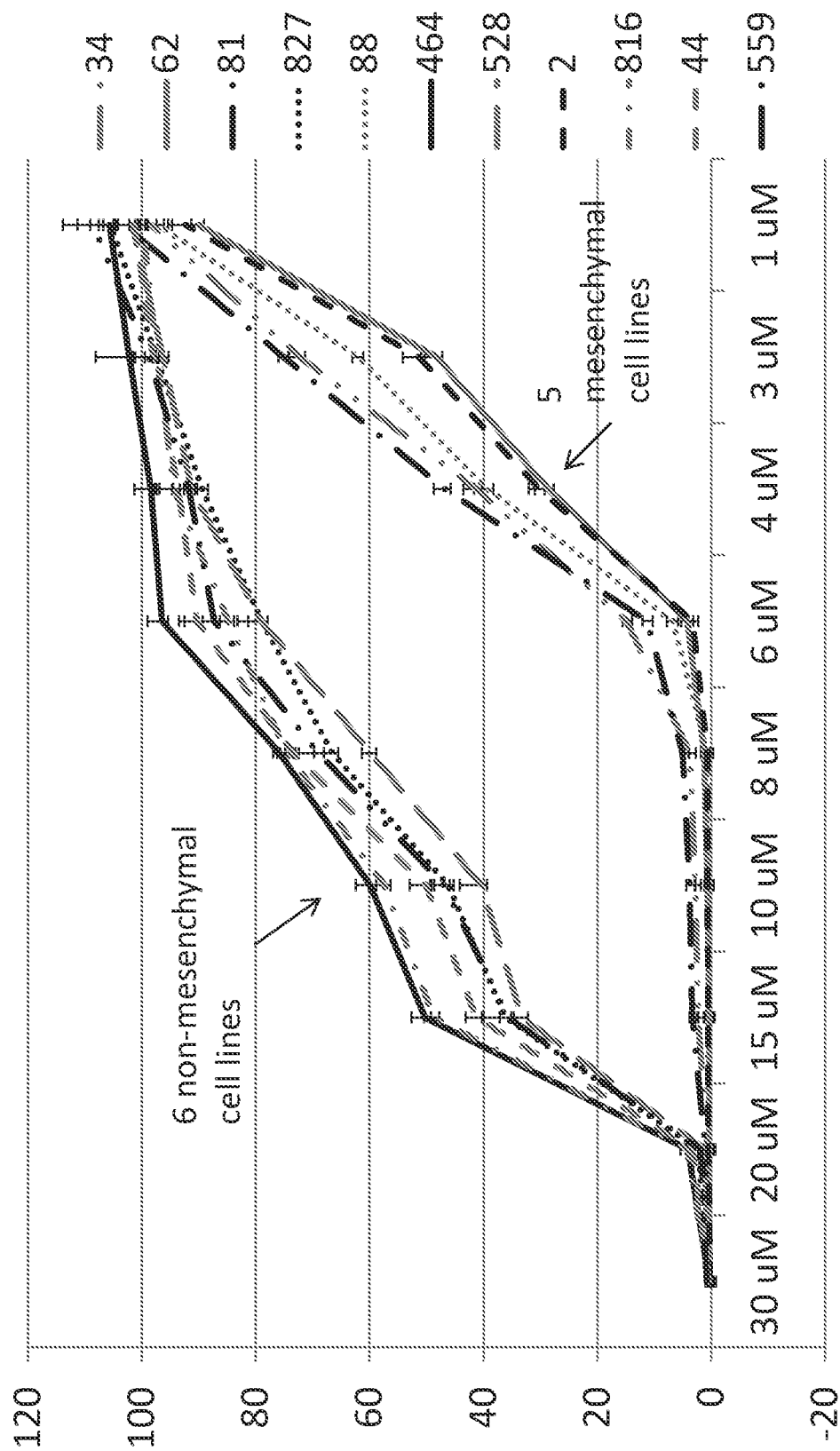
FIG. 8A is a graph showing the effects of treatment with varying concentrations of ritanserin on 5 different mesenchymal glioblastoma cell lines (81, 62, 2, 88, and 34) and 6 non-mesenchymal glioblastoma cell lines (464, 816, 44, 559, 528, and 827).
Figure 8B:
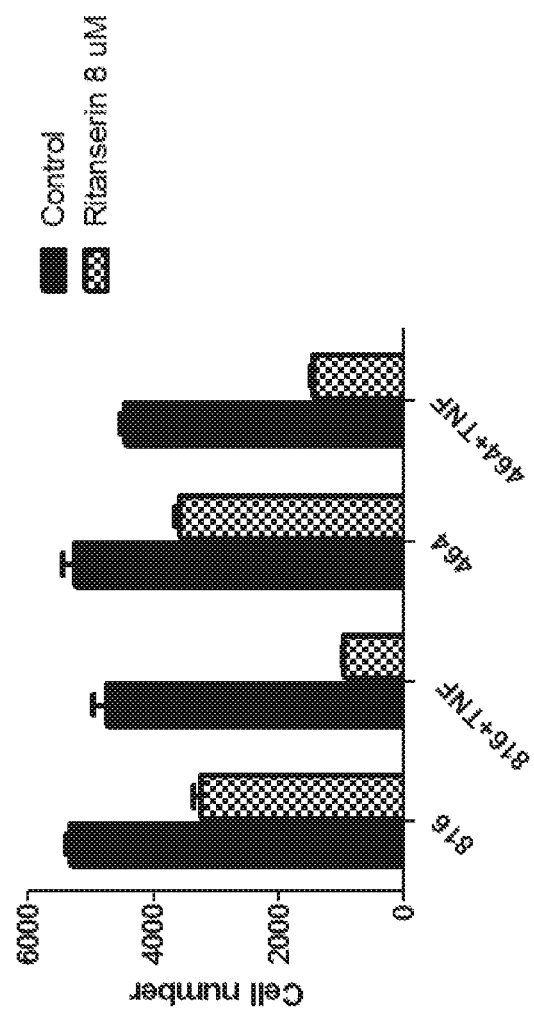
FIG. 8B is a graph showing the effects of ritanserin (checked bars) on two different proneural subtype glioblastoma cell lines (816 and 464) and on the same cell lines following TNF alpha induced proneural-to-mesenchymal transition (816+THF and 464+TNF). Data for cells treated with vehicle (control) are shown in the black bars.
Figure 8C:
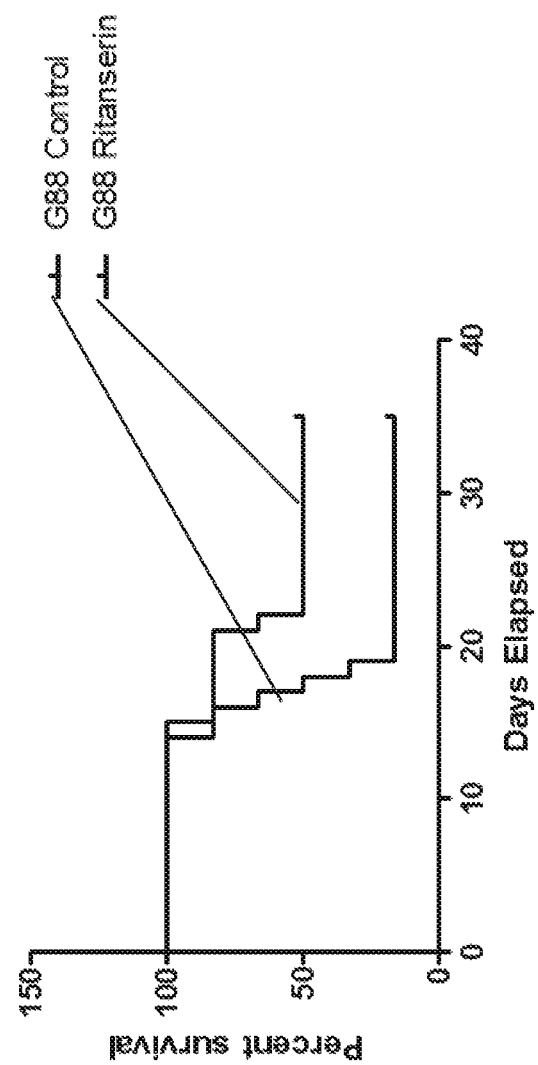
FIG. 8C is a graph of survival curves of mice implanted intracranially with G88 mesenchymal glioblastoma stem cells and treated with 50 milligrams per kilogram (mg/kg) ritanserin or vehicle (corn oil) daily starting six days after implantation.
Figure 8D:
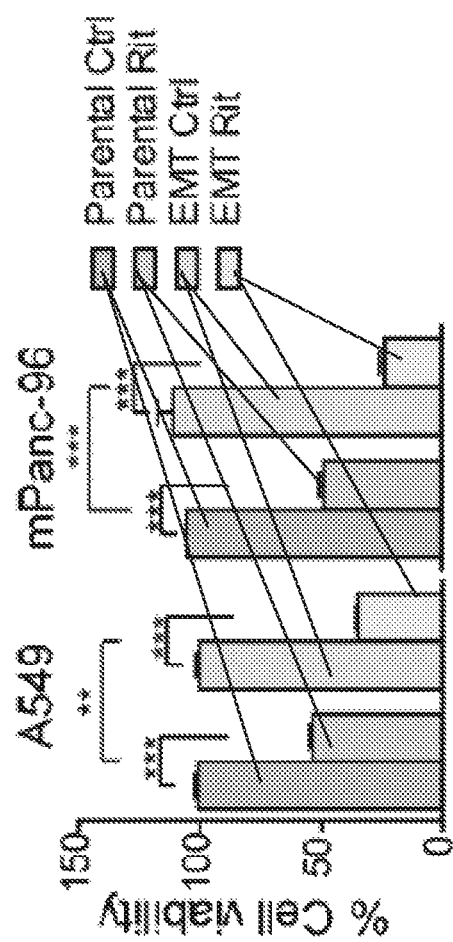
FIG. 8D is a graph showing that lung and pancreatic carcinoma cells become more sensitive to ritanserin treatment (15 micromolar (μM) and 10 μM, respectively) after epithelial-mesenchymal transition (EMT) induced with TNF-alpha and TGF-beta. "Parental Ctrl" indicates data for cells prior to EMT and without ritanserin treatment; "Parental Rit" indicates data for cells prior to EMT and with ritanserin treatment; "EMT Ctrl" indicates data for cells after EMT and without ritanserin treatment; and "EMT Rit" indicates data for cells after EMT and with ritanserin treatment. Two-way analysis of variance (ANOVA) with Bonferroni correction was used for analysis ($P<0.01$, *$P<0.0001$). All values are mean±SEM of triplicates.
Figure 8F:
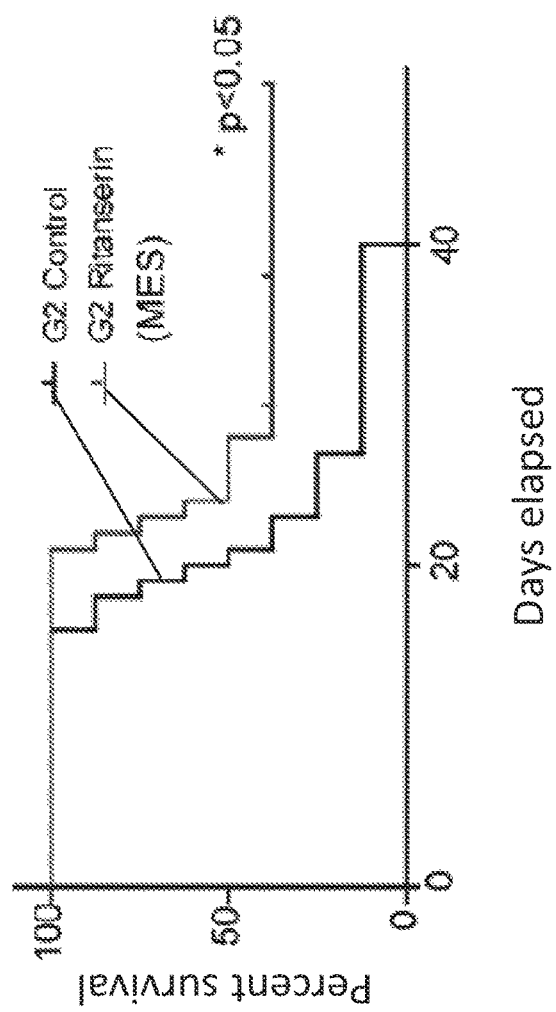
FIG. 8F is a graph of the survival curves of mice implanted intercranially with G2 mesenchymal (MES) glioblastoma stem cells and treated with 50 milligrams per kilogram (mg/kg) ritanserin or vehicle (corn oil) via oral gavage daily starting six days after implantation.
Figure 8E:
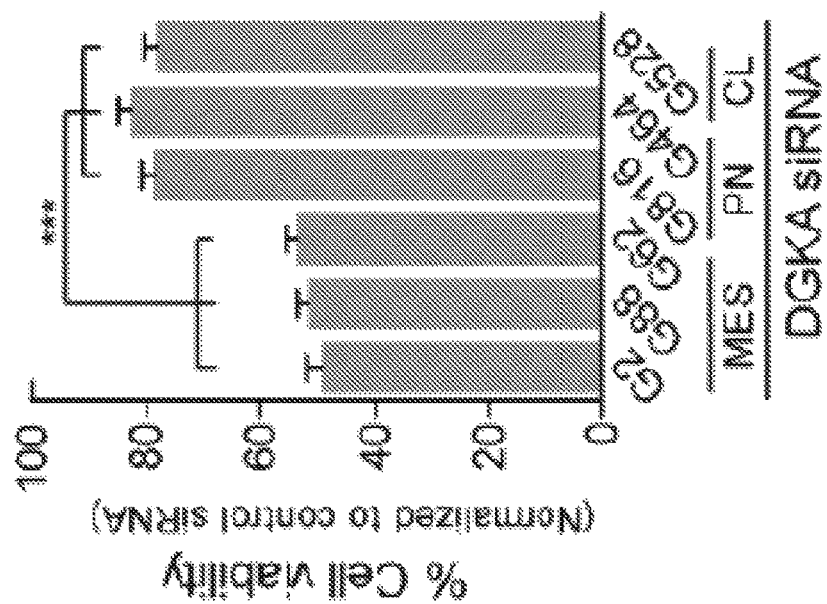
FIG. 8E is a graph showing that small interfering ribonucleic acid (siRNA) for inhibiting diacylglycerol kinase alpha (DGKα) exhibits greater cytotoxicity in mesenchymal (MES) glioblastoma cell lines (GSC) versus non-mesenchymal lines (e.g., proneural (PN) or classical (CL) lines). One-way analysis of variance (ANOVA) with post-hoc Tukey was used for analysis (***$P<0.0001$).

Glioblastomas can be categorized into four different sub-types based on gene expression patterns and clinical characterization. In vitro ritanserin treatment of 11 different GBM cell lines of various sub-types indicated that meschenchymal GBM cell lines are three to four times more sensitive to ritanserin treatment than other subtypes. See FIG. 8A. Mesenchymal GBM cells were also more sensitive to knock down of DGKα expression with small interfering RNAs (siRNAs). See FIG. 8E. In vivo studies also showed that there was increased median survival with ritanserin treatment in a mesenchymal GBM model. In particular, median survival increased from 17.5 days to 28.5 days in mice with xenografts from a G88 mesenchymal GBM stem cell line. See FIG. 8C. Median survival was also increased with oral ritanserin treatment in mice with xenografts from a G2 mesenchymal GBM stem cell line. See FIG. 8F.

Ritanserin was also more effective in proneural cell lines following conversion to a mesenchymal phenotype induced by TNF-alpha treatment. See FIG. 8B. In addition, using established epithelial-mesenchymal transition (EMT) models, both lung (A549) and pancreatic (MPanc-96) carcinoma cells became more sensitive to ritanserin post-EMP. See FIG. 8D. Thus it appears that the mesenchymal cancer phenotype can be preferentially targeted with ritanserin in GBM and in other cancers, as well.

Example 8

Radiosensitization with Ritanserin

Figures 9A, 9B:
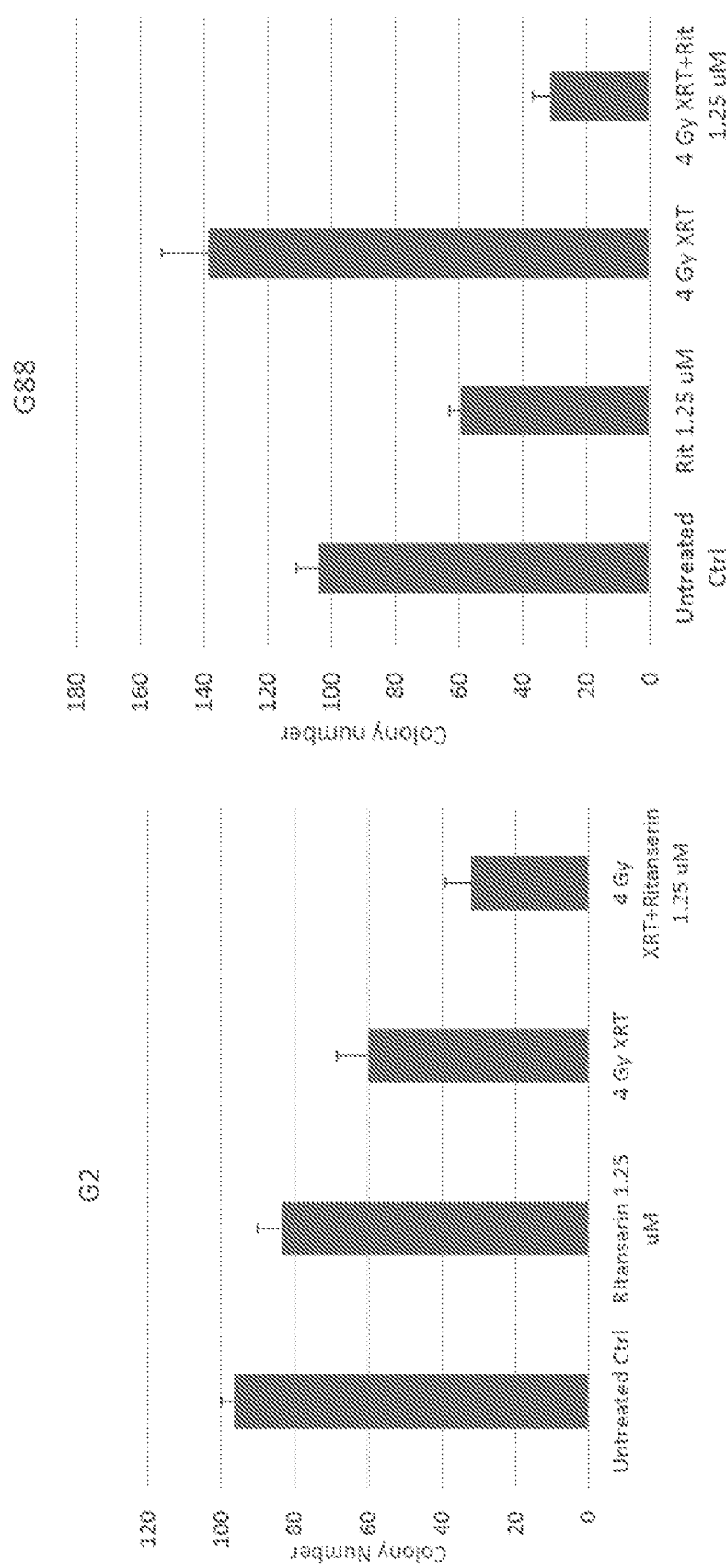
FIG. 9A is a graph showing the effects of radiation and ritanserin treatment on G2 mesenchymal glioblastoma stem cells. The stem cells were treated with 1.25 micromolar (μM) ritanserin or an equal volume:volume amount of vehicle and then treated with or without 4 gray (Gy) radiation prior to plating in soft agar colonies. After two weeks, colony numbers were counted. For comparison, data is also provided for untreated control cells.
FIG. 9B is a graph showing the effects of radiation and ritanserin treatment on radioresistant G88 mesenchymal glioblastoma stem cells. The stem cells were treated with 1.25 micromolar (μM) ritanserin or an equal volume:volume amount of vehicle and then treated with or without 4 gray (Gy) radiation prior to plating in soft agar colonies. After two weeks, colony numbers were counted. For comparison, data is also provided for untreated control cells.
Figure 9C:
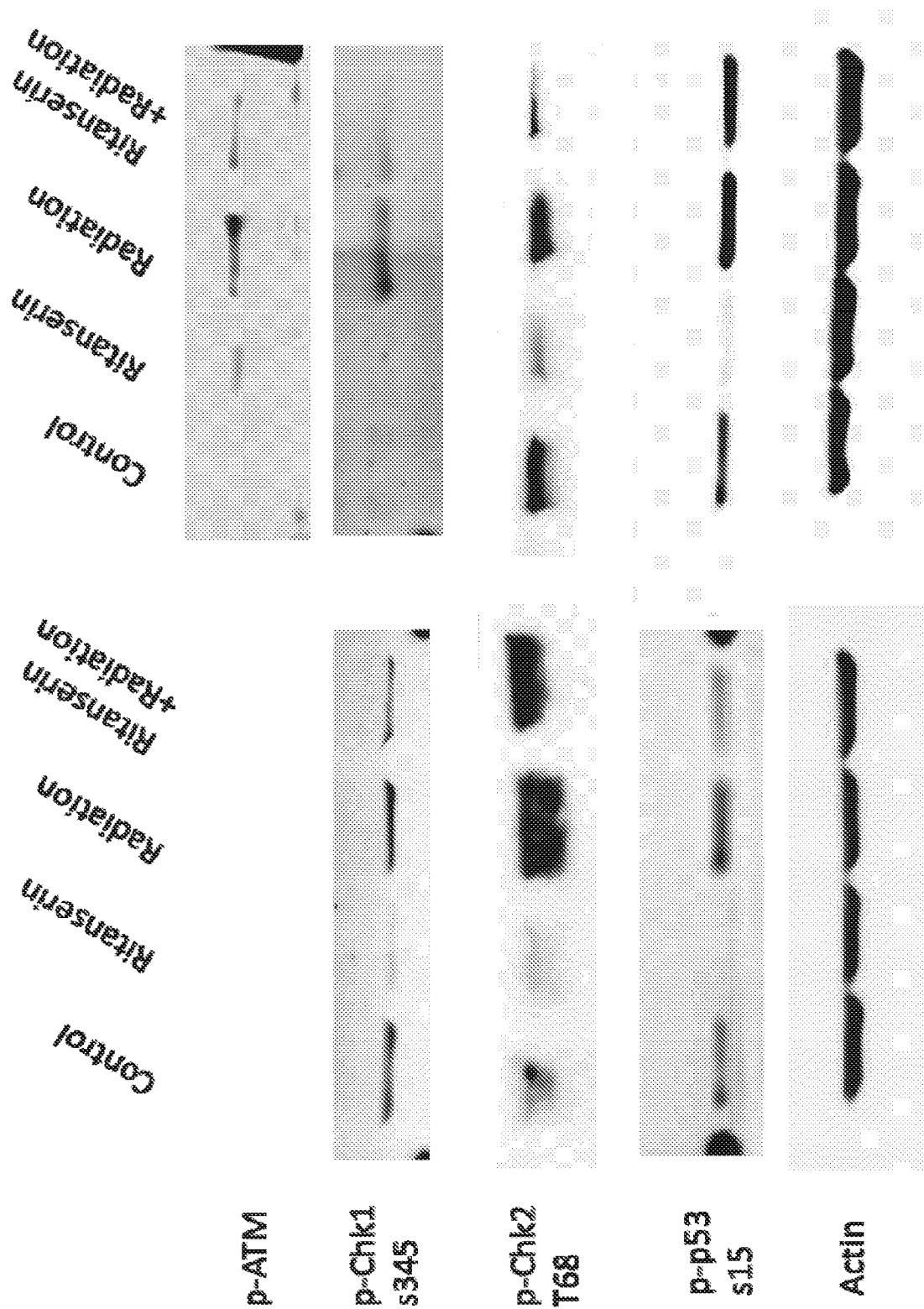
FIG. 9C are autoradiographs from an immunoblot assay of cells treated with ritanserin, radiation, or a combination of ritanserin and radiation, showing the effects of ritanserin on downstream effectors of radiation response, i.e., p-ATM, p-Chk1 s345, p-Chk2 T68, and p-p53 s15.
Figure 9E:
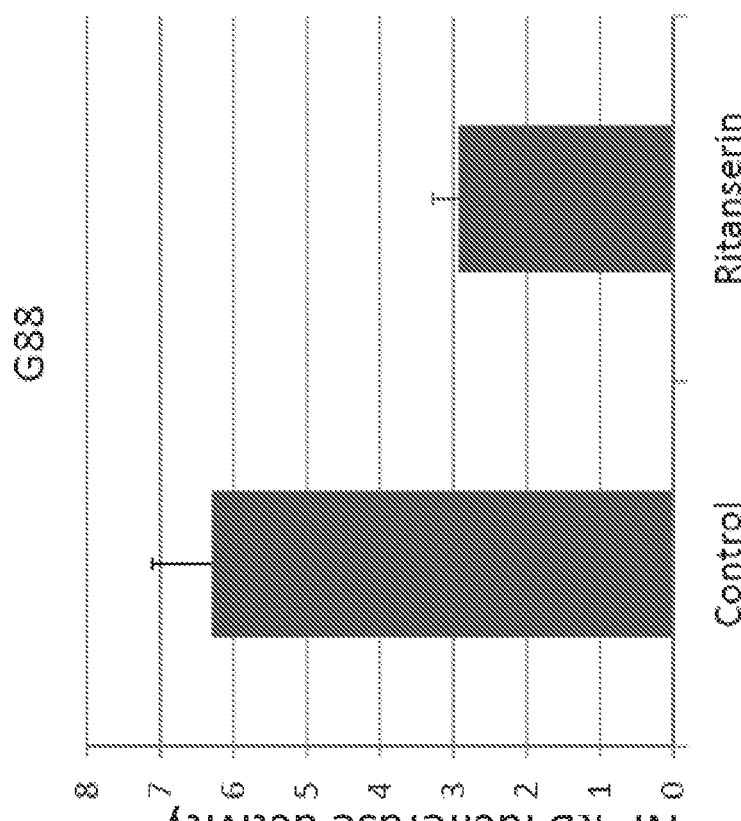
FIG. 9E is a graph showing the effect of ritanserin treatment on NF-κB expression in G88 mesenchymal glioblastoma cells. NF-κB expression was measured using a luciferase assay.
Figure 9D:
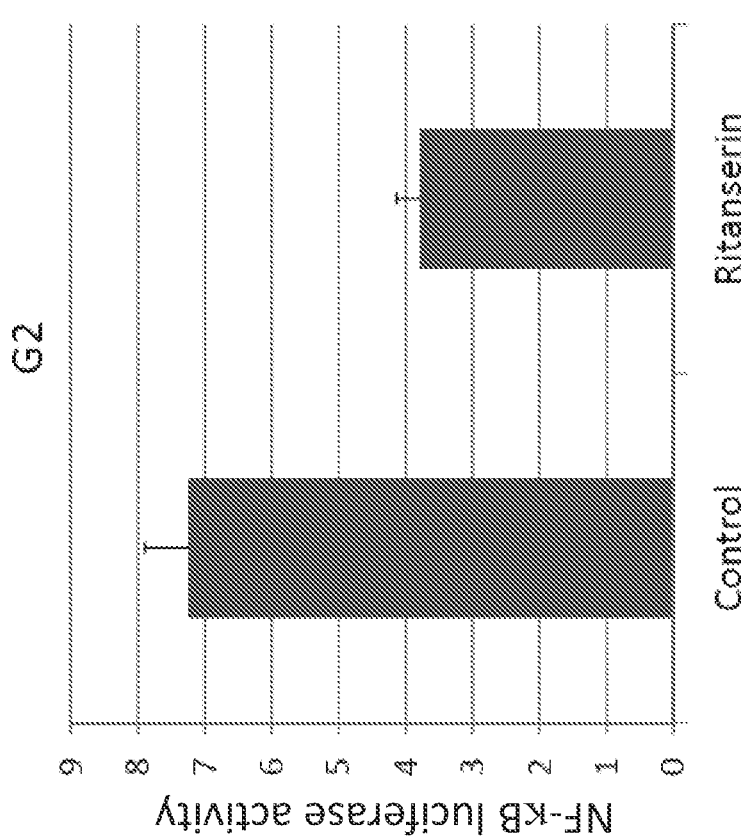
FIG. 9D is a graph showing the effect of ritanserin treatment on NF-κB expression in G2 mesenchymal glioblastoma cells. NF-κB expression was measured using a luciferase assay.

Since radiation is a frontline treatment for GBM, the combination of ritanserin treatment and radiotherapy was tested. The radiosensitization of two different mesenchymal GBM stem cells, including a radioresistant cell type (i.e., G88 cells) is shown in FIGS. 9A and 9B. In particular, while the radio-resistant cell type showed more colonies post-radiation when radiation was used alone, ritanserin had a clear radiosensitization effect. See FIG. 9A. Chou-Talalay analysis indicated synergy. Ritanserin treatment also appears to affect downstream regulators of the radiation response. See FIG. 9C. NF-κB has been indicated as a factor in radioresistance. Thus, the effect of ritanserin on NF-κB expression was also measured in two mesenchymal GBM cell lines using a NF-κB luciferase assay. Results showed that ritanserin treatment decreased NF-κB expression. See FIGS. 9D and 9E.

Example 9

Effect on Additional Downstream Mediators

Figures 10A, 10B:
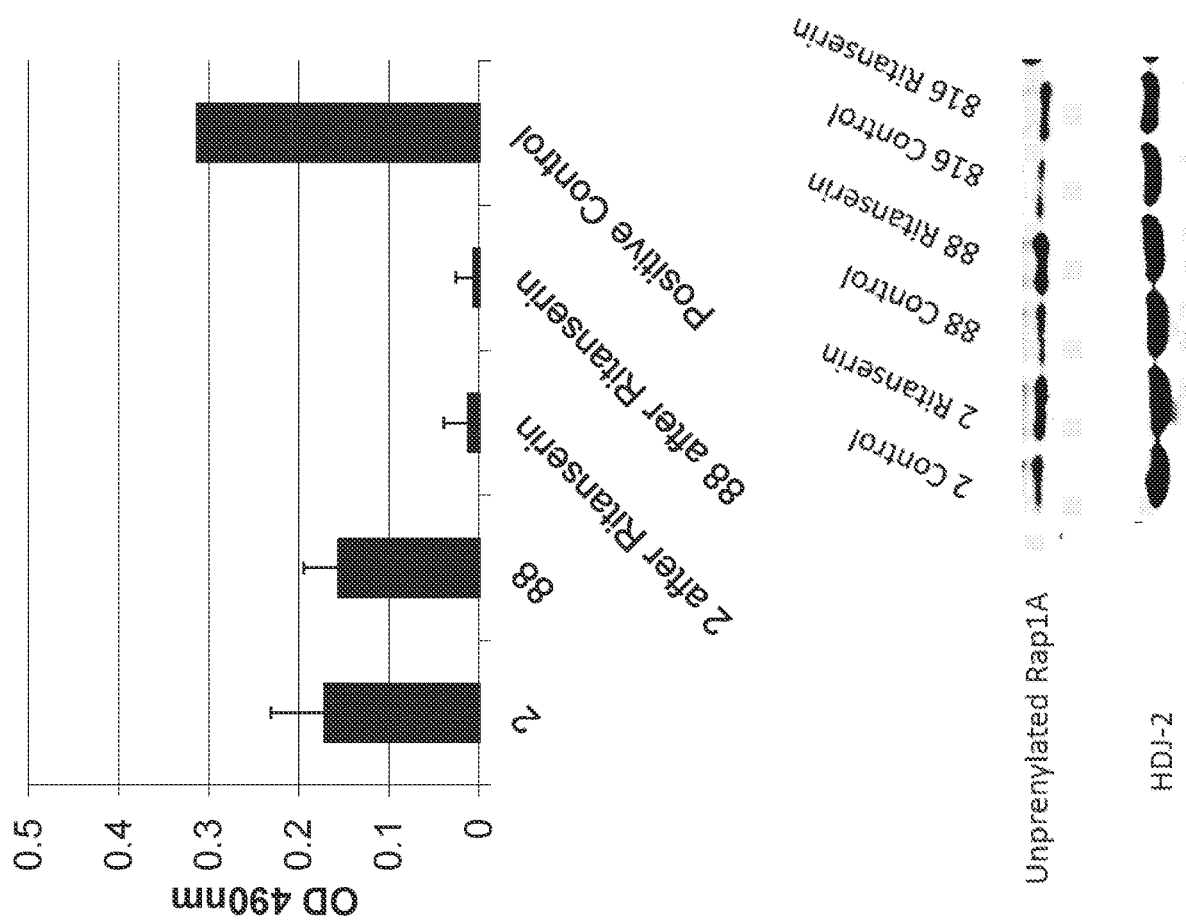
FIG. 10A is a graph showing ritanserin inhibition of RhoA measured via an enzyme-linked immunosorbent assay (ELISA) for RhoA in G2 mesenchymal glioblastoma and G88 mesenchymal glioblastoma cells.
FIG. 10B is a radiograph of the effects of ritanserin on levels of unprenylated ras-related protein Rap1A in G2 and G88 mesenchymal glioblastoma cells and in 816 non-mesenchymal glioblastoma cells.

Ritanserin also appears to inhibit RhoA expression in G2 and G88 mesenchymal GBM cells based on RhoA ELISA. See FIG. 10A. Further, based on increases in unprenylated ras-related protein Rap1A in various GBM cells, it appears that ritanserin inhibits geranylgeranyltransferase type 1 (GGTase I). See FIG. 10B.

Example 10

Synergy with Drugs with Anti-Proneural Activity

Figure 11B:
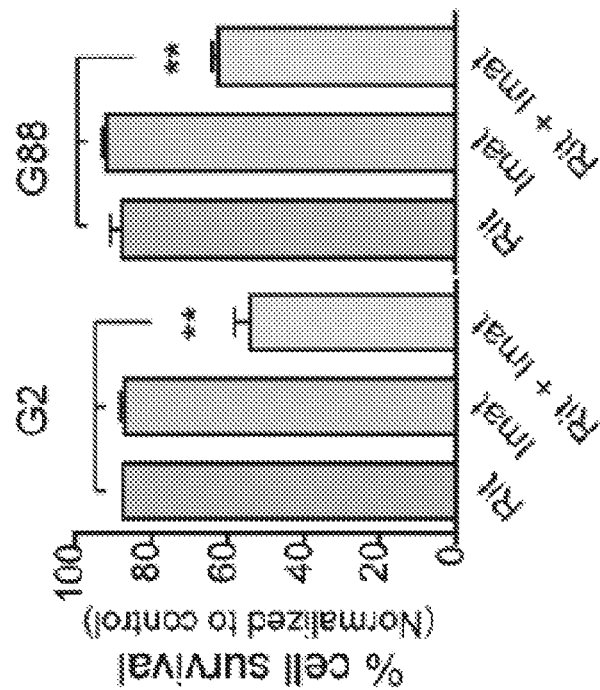
FIG. 11B is a graph showing the cytotoxic synergy between ritanserin (2 micromolar (μM)) and imatinib (0.75 μM) in G2 and G88 mesenchymal glioblastoma stem cells following five days of treatment. Significance was calculated using One-way analysis of variance (ANOVA) with post-hoc Tukey analysis (**P<0.005). All values are mean±SEM of triplicates.
Figure 11A:
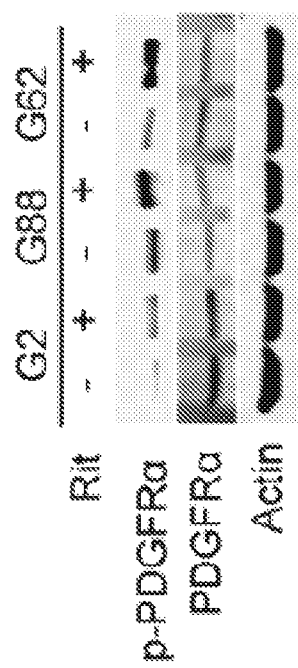
FIG. 11A is a radiograph of an immunoblot of three mesenchymal glioblastoma stem cell lines showing the activation of platelet-derived growth factor receptor alpha (PDGFRα) following three days of 3 micromolar (3 μM) ritanserin treatment.

Recent reports have indicated that shifts between GBM subtypes can be a mechanism of treatment resistance. See Mao et al., 2013; and Bhat et al., 2013. Mesenchymal GBM stem cells (GSCs) showed increased expression of key proneural markers OLIG2 and SOX2, suggesting potential mesenchymal-proneural transition (MPT) as a drug resistance mechanism. Activation of the PDGFRα pathway is another hallmark of the proneural GBM subtype. See Verhaak et al., 2010; and Phillips et al., 2006. Greater PDGFRα activation was observed with ritanserin treatment. See FIG. 11A. Combination of ritanserin with imatinib, an inhibitor of PDGFRα and other receptor tyrosine kinases found to have preferential activity against proneural GBM, showed significant synergy against mesenchymal GSCs in vitro (see FIG. 11B) and in vivo. CI values for G2 and G88 cells were 0.24 and 0.25, respectively.

REFERENCES

All references listed in the instant disclosure, including but not limited to all patents, patent applications and publications thereof, and scientific journal articles are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

Ampie L, Choy W, Lamano J B, Fakurnejad S, Bloch O, Parsa A T. Heat shock protein vaccines against glioblastoma: from bench to bedside. *J Neurooncol.* 2015; 123 (3):441-448.

Bhat K P, Balasubramaniyan V., Vaillant B., et al. Mesenchymal differentiation mediated by NF-kappaB promotes radiation resistance in glioblastoma. *Cancer Cell.* 2013; 24(3): 331-346.

Bullock T N, Mullins D W, Colella T A, Engelhard V H. Manipulation of avidity to improve effectiveness of adoptively transferred CD8(+) T cells for melanoma immunotherapy in human MHC class 1-transgenic mice. *J Immunol.* 2001; 167(10): 5824-5831.

de Chaffoy de Courcelles D C, Roevens P, Van Belle H. R 59 022, a diacylglycerol kinase inhibitor. Its effect on diacylglycerol and thrombin-induced C kinase activation in the intact platelet. *J Biol Chem.* 1985; 260(29):15762-15770.

Chou T C. Drug combination studies and their synergy quantification using the Chou-Talalay method. *Cancer Res.* 2010; 70(2):440-446.

Domingo-Musibay E, Galanis E. What next for newly diagnosed glioblastoma? *Future Oncol.* 2015.

Dominguez C L, Floyd D H, Xiao A, et al. Diacylglycerol kinase alpha is a critical signaling node and novel therapeutic target in glioblastoma and other cancers. *Cancer Discov.* 2013; 3(7):782-797.

Hori Y S, Hosoda R, Akiyama Y, et al. Chloroquine potentiates temozolomide cytotoxicity by inhibiting mitochondrial autophagy in glioma cells. *J Neurooncol.* 2015; 122(1):11-20.

Hussey et al., *J. Am. Chem. Soc.* 2003; 125:3692-3693.

Kefas B, Floyd D H, Comeau L, et al. A miR-297/hypoxia/DGK-alpha axis regulating glioblastoma survival. *Neuro Oncol.* 2013; 15(12):1652-1663.

Kim Y, Kim K H, Lee J, et al. Wnt activation is implicated in glioblastoma radioresistance. *Lab Invest.* 2012; 92(3): 466-473.

Kimura T, Takabatake Y, Takahashi A, Isaka Y. Chloroquine in cancer therapy: a double-edged sword of autophagy. *Cancer Res.* 2013; 73(1):3-7.

Klok et al., *Macromolecules* 2002; 35:746-759.

Lee S W, Kim H K, Lee N H, et al. The synergistic effect of combination temozolomide and chloroquine treatment is dependent on autophagy formation and p53 status in glioma cells. *Cancer Lett.* 2015; 360(2):195-204.

Leysen J E, Gommeren W, Van Gompel P, Wynants J, Janssen P F, Laduron P M. Receptor-binding properties in vitro and in vivo of ritanserin: A very potent and long acting serotonin-S2 antagonist. *Mol Pharmacol.* 1985; 27(6):600-611.

Loughery J, Cox M, Smith L M, Meek D W. Critical role for p53-serine 15 phosphorylation in stimulating transactivation at p53-responsive promoters. *Nucleic Acids Res.* 2014; 42(12):7666-7680.

Mao P, Joshi K, Li J, et al. Mesenchymal glioma stem cells are maintained by activated glycolytic metabolism involving aldehyde dehydrogenase 1A3. *Proc Natl Acad Sci USA.* 2013; 110(21): 8644-8649.

Nobe K, Ohata H, Momose K. Effect of diacylglycerol kinase inhibitor, R59022 on cytosolic free calcium level and force development in guinea pig *taenia coli*. *Res Commun Chem Pathol Pharmacol.* 1993; 81(3):331-343.

Olenchock B A, Guo R, Carpenter J H, et al. Disruption of diacylglycerol metabolism impairs the induction of T cell anergy. *Nat Immunol.* 2006; 7(11):1174-1181.\

Olin M R, Andersen B M, Zellmer D M, et al. Superior efficacy of tumor cell vaccines grown in physiologic oxygen. *Clin Cancer Res.* 2010; 16(19):4800-4808.

Ostrom Q T, Gittleman H, Fulop J, et al. CBTRUS Statistical Report: Primary Brain and Central Nervous System Tumors Diagnosed in the United States in 2008-2012. *Neuro Oncol.* 2015; 17 Suppl 4:iv1-iv62.

Paar et al., *J. Immunol.* 2002; 169:856-864.

Phillips H S, Kharbanda S, Chen R, et al. Molecular subclasses of high-grade glioma predict prognosis, delineate a pattern of disease progression, and resemble stages in neurogenesis. *Cancer Cell.* 2006; 9(3):157-173.

Portoghese et al., *Life Sci.* 1982; 31:1283-1286.

Portoghese et al., *J. Med. Chem.* 1986; 29:1855-1861.

Roller D G, Axelrod M, Capaldo B J, et al. Synthetic lethal screening with small-molecule inhibitors provides a pathway to rational combination therapies for melanoma. *Mol Cancer Ther.* 2012; 11(11):2505-2515.

Sato M, Liu K, Sasaki S, et al. Evaluations of the selectivities of the diacylglycerol kinase inhibitors R59022 and R59949 among diacylglycerol kinase isozymes using a new non-radioactive assay method. *Pharmacology.* 2013; 92(1-2):99-107.

Stepinski et al., *Internat. J. of Peptide & Protein Res.* 1991; 38:588-92.

Tamiz et al., *J. Med. Chem.* 2001; 44:1615-1622.

Timmerman P, Woestenborghs R, Lenoir H, Heykants J. Deuterated ritanserin analysis by gas chromatography/mass spectrometry: a sensitive technique to study human ritanserin pharmacokinetics. *Biomed Environ Mass Spectrom.* 1989; 18(7):498-502.

U.S. Pat. No. 4,160,452.

U.S. Pat. No. 4,256,108.

U.S. Pat. No. 4,265,874.

Verhaak R G, Hoadley K A, Purdom E, et al., Integrated genomic analysis identifies clinically relevant subtypes of glioblastoma characterized by abnormalities in PDGFRA, IDH1, EGFR, and NF1. *Cancer Cell.* 2010; 17(1):98-110.

Wittlinger M, Grabenbauer G G, Sprung C N, Sauer R, Distel L V. Time and dose-dependent activation of p53 serine 15 phosphorylation among cell lines with different radiation sensitivity. *Int J Radiat Biol.* 2007; 83(4):245-257.

WO 00/16750.

WO 00/57858.

Zha Y, Marks R, Ho A W, et al. T cell anergy is reversed by active Ras and is regulated by diacylglycerol kinase-alpha. *Nat Immunol.* 2006; 7(11):1166-1173.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for treating a cancer in a subject in need thereof, wherein the method comprises administering to the subject a therapeutically effective amount of ritanserin, wherein the cancer is selected from the group consisting of mesenchymal cancer, melanoma and glioblastoma.

2. The method of claim 1, wherein the method further comprises administering at least one second treatment to the subject.

3. The method of claim 2, wherein the at least one second treatment is selected from the group consisting of a surgical resection of a tumor, radiotherapy, immunotherapy, alternating electric field therapy, and chemotherapy.

4. The method of claim 2, wherein the method comprises administering to the subject at least one second treatment selected from the group consisting of temozolomide (TMZ), chloroquine, bevacizumab, imatinib, radiation, and an immunotherapeutic agent.

5. The method of claim 2, wherein the method comprises administering to the subject at least two second treatments, wherein the at least two second treatments have synergistic activity with each other.

6. The method of claim 5, wherein the at least two second treatments are TMZ and chloroquine.

7. The method of claim 1, wherein the ritanserin is administered orally to the subject.

8. The method of claim 1, wherein the subject is human.

9. A method of inducing chemo- or radiosensitivity in a subject undergoing or scheduled to undergo treatment with a chemotherapeutic agent or radiation to treat a disease or disorder treatable thereby, the method comprising administering ritanserin to the subject, wherein the disease or disorder is selected from the group consisting of mesenchymal cancer.

10. The method of claim 9, wherein administering the ritanserin is performed prior to and/or concurrently with the administration of a chemotherapeutic agent.

11. The method of claim 9, wherein administering the ritanserin is performed prior to and/or concurrently with the administration of radiation.

12. A method for inhibiting a cancer in a subject in need thereof, wherein the method comprises administering to the subject a therapeutically effective amount of ritanserin, wherein the cancer is a melanoma or a glioblastoma.

* * * * *

SEQUENCE LISTING

<160> NUMBER OF SEQ ID NOS: 1

<210> SEQ ID NO 1
<211> LENGTH: 19

```
<212> TYPE: RNA
<213> ORGANISM: Artificial Sequence
<220> FEATURE:
<223> OTHER INFORMATION: synthetic sequence

<400> SEQUENCE: 1
ggauugaccc uguuccuaa                                                   19
```